United States Patent
Chang et al.

(10) Patent No.: US 9,994,638 B2
(45) Date of Patent: *Jun. 12, 2018

(54) PEPTIDE CORE-BASED MULTI-ARM LINKERS FOR TREATING INFECTIOUS DISEASES

(71) Applicant: Immunwork Inc., Taipei City (TW)

(72) Inventors: Tse-Wen Chang, Taipei (TW);
Hsing-Mao Chu, Taipei (TW);
Chien-Jen Lin, Taipei (TW); Chun-Yu Lin, Taipei (TW)

(*) Notice: Subject to any disclaimer, the term of this patent is extended or adjusted under 35 U.S.C. 154(b) by 4 days.

This patent is subject to a terminal disclaimer.

(21) Appl. No.: 15/159,831

(22) Filed: May 20, 2016

(65) Prior Publication Data

US 2016/0339111 A1 Nov. 24, 2016

Related U.S. Application Data

(63) Continuation-in-part of application No. 14/997,764, filed on Jan. 18, 2016, and a continuation-in-part of application No. 14/997,827, filed on Jan. 18, 2016, and a continuation-in-part of application No. 14/997,849, filed on Jan. 18, 2016, now abandoned, and a continuation-in-part of application No. 14/997,874, filed on Jan. 18, 2016.

(60) Provisional application No. 62/308,349, filed on Mar. 15, 2016, provisional application No. 62/213,012, filed on Sep. 1, 2015, provisional application No. 62/164,400, filed on May 20, 2015.

(51) Int. Cl.

| | |
|---|---|
| *A61K 47/48* | (2006.01) |
| *C07K 16/10* | (2006.01) |
| *C07K 17/02* | (2006.01) |
| *C07K 16/18* | (2006.01) |
| *C07K 16/12* | (2006.01) |
| *A61K 31/137* | (2006.01) |
| *C07K 16/28* | (2006.01) |
| *C07K 14/565* | (2006.01) |
| *C07K 7/08* | (2006.01) |
| *C07K 14/00* | (2006.01) |
| *C07K 17/06* | (2006.01) |
| *A61K 47/65* | (2017.01) |
| *A61K 47/60* | (2017.01) |
| *A61K 47/64* | (2017.01) |
| *A61K 47/68* | (2017.01) |

(52) U.S. Cl.
CPC .......... *C07K 16/283* (2013.01); *A61K 31/137* (2013.01); *A61K 47/60* (2017.08); *A61K 47/64* (2017.08); *A61K 47/65* (2017.08); *A61K 47/6849* (2017.08); *A61K 47/6883* (2017.08); *C07K 7/08* (2013.01); *C07K 14/001* (2013.01); *C07K 14/565* (2013.01); *C07K 16/1027* (2013.01); *C07K 16/1203* (2013.01); *C07K 16/18* (2013.01); *C07K 16/2839* (2013.01); *C07K 16/2881* (2013.01); *C07K 17/02* (2013.01); *C07K 17/06* (2013.01); *C07K 2317/31* (2013.01); *C07K 2317/35* (2013.01); *C07K 2317/55* (2013.01); *C07K 2317/622* (2013.01); *C07K 2317/64* (2013.01); *C07K 2317/76* (2013.01); *C07K 2319/33* (2013.01); *C07K 2319/70* (2013.01); *C07K 2319/74* (2013.01)

(58) Field of Classification Search
None
See application file for complete search history.

(56) References Cited

FOREIGN PATENT DOCUMENTS

WO WO2015/117711 * 8/2015

OTHER PUBLICATIONS

Irani et al, Molecular Immunology, 2015, vol. 67, pp. 171-182.*
Horn (Quarterly Journal of Medicine, 1998, vol. 91, pp. 265-277).*
Salyers and Whitt ("Bacterial Pathogenesis", 1994, pp. 55-56).*
Both et al, Vaccine, 2013, vol. 31, pp. 1553-1559.*

* cited by examiner

*Primary Examiner* — Karen A. Canella

(57) ABSTRACT

The present disclosure provides various molecular constructs having a targeting element and an effector element. Methods for treating various diseases using such molecular constructs are also disclosed.

18 Claims, 22 Drawing Sheets

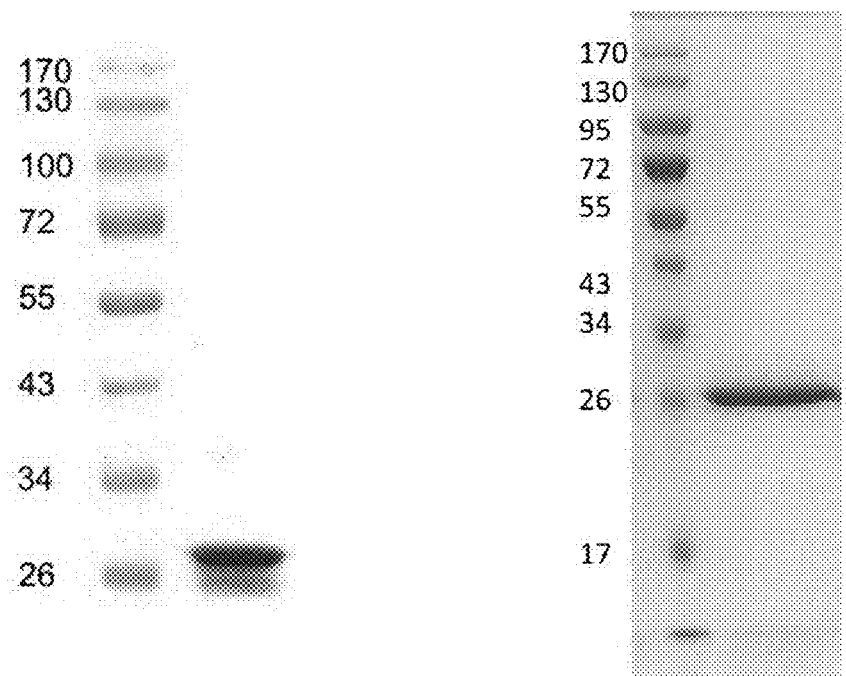
FIG. 9A
FIG. 9C
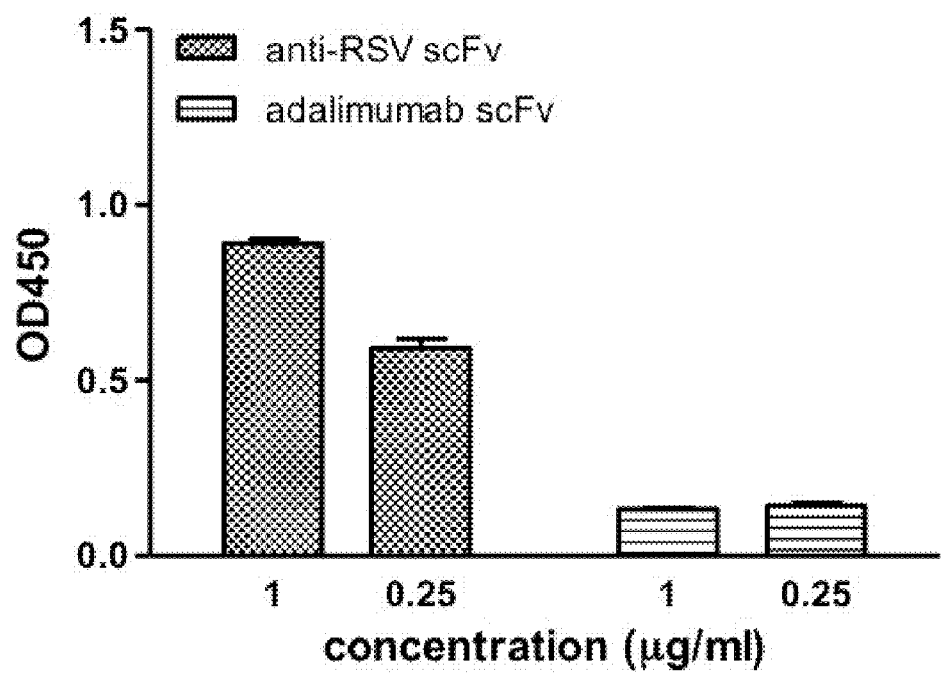
FIG. 9B

PEPTIDE CORE-BASED MULTI-ARM LINKERS FOR TREATING INFECTIOUS DISEASES

BACKGROUND OF THE INVENTION

1. Field of the Invention

The present disclosure relates to the field of pharmaceuticals; more particularly, to multi-functional molecular constructs, e.g., those having targeting and effector elements for delivering the effector (e.g., therapeutic drug) to targeted sites.

2. Description of the Related Art

The continual advancement of a broad array of methodologies for screening and selecting monoclonal antibodies (mAbs) for targeted antigens has helped the development of a good number of therapeutic antibodies for many diseases that were regarded as untreatable just a few years ago. According to Therapeutic Antibody Database, approximately 2,800 antibodies have been studied or are being planned for studies in human clinical trials, and approximately 80 antibodies have been approved by governmental drug regulatory agencies for clinical uses. The large amount of data on the therapeutic effects of antibodies has provided information concerning the pharmacological mechanisms how antibodies act as therapeutics.

One major pharmacologic mechanism for antibodies acting as therapeutics is that, antibodies can neutralize or trap disease-causing mediators, which may be cytokines or immune components present in the blood circulation, interstitial space, or in the lymph nodes. The neutralizing activity inhibits the interaction of the disease-causing mediators with their receptors. It should be noted that fusion proteins of the soluble receptors or the extracellular portions of receptors of cytokines and the Fc portion of IgG, which act by neutralizing the cytokines or immune factors in a similar fashion as neutralizing antibodies, have also been developed as therapeutic agents.

Several therapeutic antibodies that have been approved for clinical applications or subjected to clinical developments mediate their pharmacologic effects by binding to receptors, thereby blocking the interaction of the receptors with their ligands. For those antibody drugs, Fc-mediated mechanisms, such as antibody-dependent cellular cytotoxicity (ADCC) and complement-mediated cytolysis (CMC), are not the intended mechanisms for the antibodies.

Some therapeutic antibodies bind to certain surface antigens on target cells and render Fc-mediated functions and other mechanisms on the target cells. The most important Fc-mediated mechanisms are antibody-dependent cellular cytotoxicity (ADCC) and complement-mediated cytolysis (CMC), which both will cause the lysis of the antibody-bound target cells. Some antibodies binding to certain cell surface antigens can induce apoptosis of the bound target cells.

The concept and methodology for preparing antibodies with dual specificities germinated more than three decades ago. In recent year, the advancement in recombinant antibody engineering methodologies and the drive to develop improved medicine has stimulated the development bi-specific antibodies adopting a large variety of structural configurations.

For example, the bi-valent or multivalent antibodies may contain two or more antigen-binding sites. A number of methods have been reported for preparing multivalent antibodies by covalently linking three or four Fab fragments via a connecting structure. For example, antibodies have been engineered to express tandem three or four Fab repeats.

Several methods for producing multivalent antibodies by employing synthetic crosslinkers to associate, chemically, different antibodies or binding fragments have been disclosed. One approach involves chemically cross-linking three, four, and more separately Fab fragments using different linkers. Another method to produce a construct with multiple Fabs that are assembled to one-dimensional DNA scaffold was provided. Those various multivalent Ab constructs designed for binding to target molecules differ among one another in size, half-lives, flexibility in conformation, and ability to modulate the immune system. In view of the foregoing, several reports have been made for preparing molecular constructs with a fixed number of effector elements or with two or more different kinds of functional elements (e.g., at least one targeting element and at least one effector element). However, it is often difficult to build a molecular construct with a particular combination of the targeting and effector elements either using chemical synthesis or recombinant technology. Accordingly, there exists a need in the related art to provide novel molecular platforms to build a more versatile molecule suitable for covering applications in a wide range of diseases.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

<I> Peptide Core-Based Multi-Arm Linkers

In the first aspect, the present disclosure is directed to a linker unit that has at least two different functional elements linked thereto. For example, the linker unit may have linked thereto two different effector elements, one targeting element and one effector element, or one effector element and a polyethylene glycol (PEG) chain for prolonging the circulation time of the linker unit. The present linker unit is designed to have at least two different functional groups such that the functional elements can be linked thereto by reacting with the respective functional groups. Accordingly, the present linker unit can serve as a platform for preparing a molecular construct with two or more functional elements.

According to various embodiments of the present disclosure, the linker unit comprises a center core and a plurality of linking arms. The center core is a polypeptide core comprising (1) a plurality of lysine (K) resides, in which each K residue and a next K residue are separated by a filler sequence comprising glycine (G) and serine (5) residues, and the number of K residues ranges from 2 to 15; or (2) the sequence of $(X_{aa}—K)_n$, where $X_{aa}$ is a PEGylated amino acid having 2 to 12 repeats of ethylene glycol (EG) unit, and n is an integral from 2 to 15. Optionally, the filler sequence consists of 2 to 20 amino acid residues. In various embodiments, the filler sequence may have the sequence of GS, GGS, GSG, or SEQ ID NOs: 1-16. According to some embodiments of the present disclosure, the center core comprises 2-15 units of the sequence of $G_{1-5}SK$; preferably, the center core comprises the sequence of $(GSK)_{2-15}$. Each of the linking arms is linked to the K residues of the center core via forming an amide linkage between the K residue and the linking arm. The linking arm linked to the center core has a maleimide, a N-hydroxysuccinimidyl (NHS) group, an azide group, an alkyne group, a tetrazine group, a cyclooctene group, or a cyclooctyne group at its free-terminus. Also, the amino acid residue at the N- or C-terminus of the center core has an azide group or an alkyne group; alternatively or additionally, the amino acid residue at the N- or C-terminus of the center core is a cysteine (C) residue, in which the thiol group of the amino acid residue is linked with a coupling arm having an azide group, an alkyne group, a tetrazine group, a cyclooctene group, or a cyclooctyne group at the free terminus of the coupling arm.

According to some embodiments of the present disclosure, when the free terminus of the linking arm is the azide, the alkyne, or the cyclooctyne group, then the amino acid residue at the N- or C-terminus of the center core is a cysteine residue, and the free terminus of the coupling arm is the tetrazine or the cyclooctene group. According to other embodiments of the present disclosure, when the free terminus of the linking arm is the tetrazine group or cyclooctene group, then the amino acid residue at the N- or C-terminus of the center core has the azide or the alkyne group, or the amino acid residue at the N- or C-terminus of the center core is a cysteine residue, and the free terminus of the coupling arm is the azide, the alkyne, or the cyclooctyne group.

In some embodiments, the linking arm is a PEG chain, preferably having 2 to 20 repeats of EG units. Alternatively, the linking arm is a PEG chain having 2 to 20 repeats of EG units with a disulfide linkage at the free terminus thereof (i.e., the terminus that is not linked with the K residue of the center core). In some embodiments, the coupling linking arm is a PEG chain, preferably having 2 to 12 repeats of EG units.

Regarding amino acid residues having the azide group, non-limiting examples of said amino acid residues include L-azidohomoalanine (AHA), 4-azido-L-phenylalanine, 4-azido-D-phenylalanine, 3-azido-L-alanine, 3-azido-D-alanine, 4-azido-L-homoalanine, 4-azido-D-homoalanine, 5-azido-L-ornithine, 5-azido-d-ornithine, 6-azido-L-lysine, and 6-azido-D-lysine. As to the amino acid residues having the alkyne group, illustrative examples thereof include L-homopropargylglycine (L-HPG), D-homopropargylglycine (D-HPG), and beta-homopropargylglycine (β-HPG).

When the amino acid residues at the N- or C-terminus of the center core is the cysteine residue, the cyclooctene group at the free terminus of the coupling arm may be, a trans-cyclooctene (TCO) group, while the cyclooctyne group at the free terminus of the coupling arm may be a dibenzocyclooctyne (DBCO), difluorinated cyclooctyne (DIFO), bicyclononyne (BCN), or dibenzocyclooctyne (DICO) group. Alternatively, the tetrazine group at the free terminus of the coupling arm includes, but is not limited to, 1,2,3,4-tetrazine, 1,2,3,5-tetrazine, and 1,2,4,5-tetrazine, and derivatives thereof, such as, 6-methyl tetrazine.

According to various embodiments of the present disclosure, the linker unit further comprises a plurality of first elements. In some embodiments, each of the first elements is linked to one of the linking arms via forming an amide bound between the linking arm and the first element. In other embodiments, each of the first elements is linked to one of the linking arms via copper catalyzed azide-alkyne cycloaddition (CuAAC) reaction, strained-promoted azide-alkyne click chemistry (SPAAC) reaction, or inverse electron demand Diels-Alder (iEDDA) reaction occurred between the linking arm and the first element.

Optionally, the present linker unit further comprises a plurality of connecting arms that are respectively linked to the plurality of linking arms via CuAAC reaction, SPAAC reaction, or iEDDA reaction. According to the embodiments of the present disclosure, each of the plurality of connecting arms has a maleimide or the NHS group at the element-linking terminus thereof (i.e., the terminus that is not linked with the linking arm). Accordingly, each of the first elements is linked to one of the connecting arms via the thiol-maleimide reaction occurred between the connecting arm and the first element; or each of the first elements is linked to one of the connecting arms via forming an amide bound between the connecting arm and the first element. In some embodiments, each of the connecting arms is a PEG chain, preferably having 2-20 repeats of EG units. In other embodiments, each of the connecting arms is a PEG chain having 2-20 repeats of EG units with a disulfide linkage at the element-linking terminus.

According to various optional embodiments of the present disclosure, the first element is an effector element suitable for eliciting an intended effect (e.g., a therapeutic effect) in a subject. Alternatively, the first element may be a targeting element for directing the linker unit to the site of interest. According to the embodiments of the present disclosure, the first element is fingolimod, fingolimod phosphate, interferon-β, or a single-chain variable fragment (scFv) specific for integrin-α4, β-amyloid, a viral protein, a bacterial protein.

Still optionally, the linker unit further comprises a second element that is different from the first elements. In some embodiments, the second element has an azide or alkyne group, so that it is linked to the center core or the coupling arm by coupling with the corresponding alkyne or azide group of the center core or the coupling arm via CuAAC reaction. Alternatively, in some embodiments, the second element having an azide or cyclooctyne group is linked to the center core or the coupling arm by coupling with the corresponding cyclooctyne or azide group of the center core or the coupling arm via SPAAC reaction. Still alternatively, in certain embodiments, the second element having a tetrazine or cyclooctene group is linked to the center core or the coupling arm by coupling with the corresponding cyclooctene or tetrazine group of the center core or the coupling arm via iEDDA) reaction. According to some embodiments, the linker unit comprises the connecting arm, which is linked to the linking arm via CuAAC reaction or SPAAC reaction; in these embodiments, the N- or C-terminus of the center core or the free terminus of the coupling arm has a tetrazine or cyclooctene group so that the second element having the corresponding cyclooctene or tetrazine group is linked to the center core or the coupling arm via iEDDA reaction. According to other embodiments, the linker unit comprises the connecting arm, which is linked to the linking arm via iEDDA reaction; in these conditions, the N- or C-terminus of the center core or the free terminus of the coupling arm has an azide, alkyne, or cyclooctyne group so that the second element having the corresponding chemical groups is linked to the center core or the coupling arm via CuAAC reaction or SPAAC reaction.

In optional embodiments of the present disclosure, when the first element is an effector element, then the second element may be another effector element, which works additively or synergistically with or independently of the first element; alternatively, the second element may be a targeting element or an element for improving the pharmacokinetic property of the linker unit, such as solubility, clearance, half-life, and bioavailability. In some other optional embodiments, when the first element is the targeting element, then the second element is preferably an effector element or an element for improving the pharmacokinetic property of the linker unit.

In certain embodiments, the linker unit further comprises an optional third element that is different from the first and second elements. In the case where the second element is directly linked to the center core, the other terminus (i.e., the free terminus that is not linked with the second element) of the center core is optionally a cysteine residue, which can be used to introduce an optional third element. Specifically, the thiol group of the cysteine residue is reacted with a maleimide group of a PEG chain; and the thus-linked PEG chain is designated as the coupling arm, which has a tetrazine group or a cyclooctene group at its free terminus. Accordingly, the third element is then linked to the coupling arm via iEDDA reaction. In the case where the linker unit comprises both the second and third elements, it is preferable that at least one of the first and second elements is an effector as described above, while the third element may be the element for improving the pharmacokinetic property of the linker unit. One example of the element for improving the pharmacokinetic property is a long PEG chain having a molecular weight of about 20,000 to 50,000 daltons.

<II> Uses of Peptide Core-Based Multi-Arm Linkers

The linker unit according to the first aspect of the present disclosure may find its utility in clinical medicine for the treatment of various diseases. Hence, the second aspect of the present disclosure is directed to a method for treating these diseases. According to various embodiments of the present disclosure, the method for treating a particular disease includes the step of administering to the subject in need thereof a therapeutically effective amount of the linker unit according to the above-mentioned aspect and embodiments of the present disclosure. As could be appreciated, said linker unit may be administered in a pharmaceutical formulation, which comprises a pharmaceutically-acceptable excipient suitable for the intended or desired administration route, in addition to the present linker unit.

Various illustrative combinations of the first and second elements of the present linker unit for treating some particular diseases are disclosed below for facilitating the understanding of some embodiments of the present disclosure.

According to some embodiments of the present disclosure, the present linker unit is useful in treating a central nervous system (CNS) disease, for example, multiple sclerosis and Alzheimer's disease. For the treatment of multiple sclerosis, the first element can be fingolimod, fingolimod phosphate, interferon-β, or an scFv specific for integrin-α4. For the purpose of treating Alzheimer's disease, the element is an scFv specific for β-amyloid.

According to other embodiments of the present disclosure, the linker units suitable for treating an infectious disease comprise an scFv specific for a viral protein or a bacterial protein as the first element. In one preferred embodiment, the viral protein is F protein of respiratory syncytia virus (RSV), gp120 protein of human deficiency virus type 1 (HIV-1), hemagglutinin A (HA) protein of influenza A virus, or glycoprotein of cytomegalovirus; and the bacterial protein is endotoxin of Gram(−) bacteria, surface antigen of *Clostridium difficile*, lipoteichoic acid of *Staphylococcus aureus*, anthrax toxin of *Bacillus anthracis*, or Shiga-like toxin type I or II of *Escherichia coli*.

BRIEF DESCRIPTION OF THE DRAWINGS

The present description will be better understood from the following detailed description read in light of the accompanying drawings briefly discussed below.

FIG. 7 shows the SDS-PAGE analysis result of the purified ectodomain of human CD32a.

FIG. 9A shows the SDS-PAGE analysis result of the purified scFv specific for Protein F of RSV; FIG. 9B shows the ELISA analysis result of the purified scFv specific for Protein F of RSV; FIG. 9C shows the SDS-PAGE analysis result of the purified scFv specific for endotoxin; FIG. 9E shows the SDS-PAGE analysis result of the purified scFv specific for the ectodomain of CD32a; and FIG. 9F shows the ELISA analysis of the purified scFv specific for the ectodomain of CD32a.

FIG. 11A shows the data of the titers of the phages bearing scFvs specific for ectodomain of human CD32a; and FIG. 11B shows the single colony ELISA analysis result of phage-displayed scFvs specific for the ectodomain of human CD32a.

FIG. 13A and FIG. 13B respectively show the results of ELISA analysis and mass spectrometric analysis of TCO-conjugated scFv specific for CD32a.

Figure 1A:
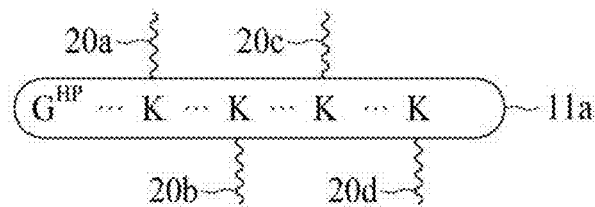
FIG. 1A to FIG. 1N are schematic diagrams illustrating linker units according to certain embodiments of the present disclosure.

In accordance with common practice, the various described features/elements are not drawn to scale but instead are drawn to best illustrate specific features/elements relevant to the present invention. Also, like reference numerals and designations in the various drawings are used to indicate like elements/parts, where possible.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art.

Unless otherwise required by context, it will be understood that singular terms shall include plural forms of the same and plural terms shall include the singular. Specifically, as used herein and in the claims, the singular forms "a" and "an" include the plural reference unless the context clearly indicated otherwise. Also, as used herein and in the claims, the terms "at least one" and "one or more" have the same meaning and include one, two, three, or more. Furthermore, the phrases "at least one of A, B, and C", "at least one of A, B, or C" and "at least one of A, B and/or C," as use throughout this specification and the appended claims, are intended to cover A alone, B alone, C alone, A and B together, B and C together, A and C together, as well as A, B, and C together.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

This present disclosure pertains generally to molecular constructs, in which each molecular construct comprises a targeting element (T) and an effector element (E), and these molecular constructs are sometimes referred to as "T-E molecules", "T-E pharmaceuticals" or "T-E drugs" in this document.

As used herein, the term "targeting element" refers to the portion of a molecular construct that directly or indirectly binds to a target of interest (e.g., a receptor on a cell surface or a protein in a tissue) thereby facilitates the transportation of the present molecular construct into the interested target. In some example, the targeting element may direct the molecular construct to the proximity of the target cell. In other cases, the targeting element specifically binds to a molecule present on the target cell surface or to a second molecule that specifically binds a molecule present on the cell surface. In some cases, the targeting element may be internalized along with the present molecular construct once it is bound to the interested target, hence is relocated into the cytosol of the target cell. A targeting element may be an antibody or a ligand for a cell surface receptor, or it may be a molecule that binds such antibody or ligand, thereby indirectly targeting the present molecular construct to the target site (e.g., the surface of the cell of choice). The localization of the effector (therapeutic agent) in the diseased site will be enhanced or favored with the present molecular constructs as compared to the therapeutic without a targeting function. The localization is a matter of degree or relative proportion; it is not meant for absolute or total localization of the effector to the diseased site.

According to the present invention, the term "effector element" refers to the portion of a molecular construct that elicits a biological activity (e.g., inducing immune responses, exerting cytotoxic effects and the like) or other functional activity (e.g., recruiting other hapten tagged therapeutic molecules), once the molecular construct is directed to its target site. The "effect" can be therapeutic or diagnostic. The effector elements encompass those that bind to cells and/or extracellular immunoregulatory factors. The effector element comprises agents such as proteins, nucleic acids, lipids, carbohydrates, glycopeptides, drug moieties (both small molecule drug and biologics), compounds, elements, and isotopes, and fragments thereof.

Although the terms, first, second, third, etc., may be used herein to describe various elements, components, regions, and/or sections, these elements (as well as components, regions, and/or sections) are not to be limited by these terms.

Also, the use of such ordinal numbers does not imply a sequence or order unless clearly indicated by the context. Rather, these terms are simply used to distinguish one element from another. Thus, a first element, discussed below, could be termed a second element without departing from the teachings of the exemplary embodiments.

Here, the terms "link," "couple," and "conjugates" are used interchangeably to refer to any means of connecting two components either via direct linkage or via indirect linkage between two components.

The term "polypeptide" as used herein refers to a polymer having at least two amino acid residues. Typically, the polypeptide comprises amino acid residues ranging in length from 2 to about 200 residues; preferably, 2 to 50 residues. Where an amino acid sequence is provided herein, L-, D-, or beta amino acid versions of the sequence are also contemplated. Polypeptides also include amino acid polymers in which one or more amino acid residues are an artificial chemical analogue of a corresponding naturally occurring amino acid, as well as to naturally occurring amino acid polymers. In addition, the term applies to amino acids joined by a peptide linkage or by other, "modified linkages," e.g., where the peptide bond is replaced by an α-ester, a β-ester, a thioamide, phosphoramide, carbomate, hydroxylate, and the like.

In certain embodiments, conservative substitutions of the amino acids comprising any of the sequences described herein are contemplated. In various embodiments, one, two, three, four, or five different residues are substituted. The term "conservative substitution" is used to reflect amino acid substitutions that do not substantially alter the activity (e.g., biological or functional activity and/or specificity) of the molecule. Typically, conservative amino acid substitutions involve substitution one amino acid for another amino acid with similar chemical properties (e.g., charge or hydrophobicity). Certain conservative substitutions include "analog substitutions" where a standard amino acid is replaced by a non-standard (e.g., rare, synthetic, etc.) amino acid differing minimally from the parental residue. Amino acid analogs are considered to be derived synthetically from the standard amino acids without sufficient change to the structure of the parent, are isomers, or are metabolite precursors.

In certain embodiments, polypeptides comprising at least 80%, preferably at least 85% or 90%, and more preferably at least 95% or 98% sequence identity with any of the sequences described herein are also contemplated.

"Percentage (%) amino acid sequence identity" with respect to the polypeptide sequences identified herein is defined as the percentage of polypeptide residues in a candidate sequence that are identical with the amino acid residues in the specific polypeptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two polypeptide sequences was carried out by computer program Blastp (protein-protein BLAST) provided online by Nation Center for Biotechnology Information (NCBI). The percentage amino acid sequence identity of a given polypeptide sequence A to a given polypeptide sequence B (which can alternatively be phrased as a given polypeptide sequence A that has a certain % amino acid sequence identity to a given polypeptide sequence B) is calculated by the formula as follows:

$$\frac{X}{Y} \times 100\%$$

where X is the number of amino acid residues scored as identical matches by the sequence alignment program BLAST in that program's alignment of A and B, and where Y is the total number of amino acid residues in A or B, whichever is shorter.

The term "PEGylated amino acid" as used herein refers to a polyethylene glycol (PEG) chain with one amino group and one carboxyl group. Generally, the PEGylated amino acid has the formula of $NH_2$—$(CH_2CH_2O)_n$—COOH. In the present disclosure, the value of n ranges from 1 to 20; preferably, ranging from 2 to 12.

As used herein, the term "terminus" with respect to a polypeptide refers to an amino acid residue at the N- or C-end of the polypeptide. With regard to a polymer, the term "terminus" refers to a constitutional unit of the polymer (e.g., the polyethylene glycol of the present disclosure) that is positioned at the end of the polymeric backbone. In the present specification and claims, the term "free terminus" is used to mean the terminal amino acid residue or constitutional unit is not chemically bound to any other molecular.

The term "antigen" or "Ag" as used herein is defined as a molecule that elicits an immune response. This immune response may involve a secretory, humoral and/or cellular antigen-specific response. In the present disclosure, the term "antigen" can be any of a protein, a polypeptide (including mutants or biologically active fragments thereof), a polysaccharide, a glycoprotein, a glycolipid, a nucleic acid, or a combination thereof.

In the present specification and claims, the term "antibody" is used in the broadest sense and covers fully assembled antibodies, antibody fragments that bind with antigens, such as antigen-binding fragment (Fab/Fab'), F(ab')$_2$ fragment (having two antigen-binding Fab portions linked together by disulfide bonds), variable fragment (Fv), single chain variable fragment (scFv), bi-specific single-chain variable fragment (bi-scFv), nanobodies, unibodies and diabodies. "Antibody fragments" comprise a portion of an intact antibody, preferably the antigen-binding region or variable region of the intact antibody. Typically, an "antibody" refers to a protein consisting of one or more polypeptides substantially encoded by immunoglobulin genes or fragments of immunoglobulin genes. The well-known immunoglobulin genes include the kappa, lambda, alpha, gamma, delta, epsilon, and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. A typical immunoglobulin (antibody) structural unit is known to comprise a tetramer. Each tetramer is composed of two identical pairs of polypeptide chains, with each pair having one "light" chain (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively. According to embodiments of the present disclosure, the antibody fragment can be produced by modifying the nature antibody or by de novo synthesis using recombinant DNA methodologies. In certain embodiments of the present disclosure, the antibody and/or antibody fragment can be bispecific, and can be in various configurations. For example, bispecific antibodies may comprise two different antigen binding sites (variable regions). In various embodiments, bispecific antibodies can be produced by hybridoma technique or recombinant DNA technique. In certain embodiments, bispecific antibodies have binding specificities for at least two different epitopes.

The term "specifically binds" as used herein, refers to the ability of an antibody or an antigen-binding fragment thereof, to bind to an antigen with a dissociation constant (Kd) of no more than about $1\times10^{-6}$ M, $1\times10^{-7}$ M, $1\times10^{-8}$ M, $1\times10^{-9}$ M, $1\times10^{-10}$ M, $1\times10^{-11}$ M, $1\times10^{-12}$ M, and/or to bind to an antigen with an affinity that is at least two-folds greater than its affinity to a nonspecific antigen.

The term "treatment" as used herein includes preventative (e.g., prophylactic), curative or palliative treatment; and "treating" as used herein also includes preventative (e.g., prophylactic), curative or palliative treatment. In particular, the term "treating" as used herein refers to the application or administration of the present molecular construct or a pharmaceutical composition comprising the same to a subject, who has a medical condition a symptom associated with the medical condition, a disease or disorder secondary to the medical condition, or a predisposition toward the medical condition, with the purpose to partially or completely alleviate, ameliorate, relieve, delay onset of, inhibit progression of, reduce severity of, and/or reduce incidence of one or more symptoms or features of said particular disease, disorder, and/or condition. Treatment may be administered to a subject who does not exhibit signs of a disease, disorder, and/or condition, and/or to a subject who exhibits only early signs of a disease, disorder and/or condition, for the purpose of decreasing the risk of developing pathology associated with the disease, disorder and/or condition.

The term "effective amount" as used herein refers to the quantity of the present molecular construct that is sufficient to yield a desired therapeutic response. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as particular condition being treated, the physical condition of the patient (e.g., the patient's body mass, age, or gender), the type of subject being treated, the duration of the treatment, the nature of concurrent therapy (if any), and the specific formulations employed and the structure of the compounds or its derivatives. Effective amount may be expressed, for example, as the total mass of active component (e.g., in grams, milligrams or micrograms) or a ratio of mass of active component to body mass, e.g., as milligrams per kilogram (mg/kg).

The terms "application" and "administration" are used interchangeably herein to mean the application of a molecular construct or a pharmaceutical composition of the present invention to a subject in need of a treatment thereof.

The terms "subject" and "patient" are used interchangeably herein and are intended to mean an animal including the human species that is treatable by the molecular construct, pharmaceutical composition, and/or method of the present invention. The term "subject" or "patient" intended to refer to both the male and female gender unless one gender is specifically indicated. Accordingly, the term "subject" or "patient" comprises any mammal, which may benefit from the treatment method of the present disclosure. Examples of a "subject" or "patient" include, but are not limited to, a human, rat, mouse, guinea pig, monkey, pig, goat, cow, horse, dog, cat, bird and fowl. In an exemplary embodiment, the patient is a human. The term "mammal" refers to all members of the class Mammalia, including humans, primates, domestic and farm animals, such as rabbit, pig, sheep, and cattle; as well as zoo, sports or pet animals; and rodents, such as mouse and rat. The term "non-human mammal" refers to all members of the class Mammalis except human.

The present disclosure is based, at least on the construction of the T-E pharmaceuticals that can be delivered to target cells, target tissues or organs at increased proportions relative to the blood circulation, lymphoid system, and other cells, tissues or organs. When this is achieved, the therapeutic effect of the pharmaceuticals is increased, while the scope and severity of the side effects and toxicity is decreased. It is also possible that a therapeutic effector is administered at a lower dosage in the form of a T-E molecule, than in a form without a targeting component. Therefore, the therapeutic effector can be administered at lower dosages without losing potency, while lowering side effects and toxicity.

Diseases that can Benefit from Better Drug Targeting

Drugs used for many diseases can be improved for better efficacy and safety, if they can be targeted to the disease sites, i.e., if they can be localized or partitioned to the disease sites more favorably than the normal tissues or organs. Certain antibody drugs, which target infectious microorganisms or their toxic products, can be improved, if they are empowered with the ability to recruit immunocytes, which phagocytose and clear the antibody-bound particles. Following are primary examples of diseases, in which drugs can be improved if they can be preferentially distributed to the disease sites or cells or if they can recruit phagocytic immunocytes.

I Central Nervous System Diseases

For treating diseases of the central nervous system (CNS), the therapeutic agents are often required to pass through the blood-brain barrier (BBB) to get into the CNS. Some therapeutic agents do not get into the CNS; they regulate certain activities, such as immune activities, in the peripheral, which then modulates the diseased conditions in the CNS. The BBB is formed by the endothelial cells lining the capillaries of blood vessels in the CNS. Unlike the capillaries in the peripheral tissues and organs, the capillary endothelial cells in the BBB are connected by tight junctions formed by occludin, claudins, and junctional adhesion molecules.

At least six antibodies, namely, aducanumab, bapineromab, crenezumab, gantenerumab, ponezumab, and solanezumab, specific for β-amyloid, which is responsible for causing Alzheimer's disease, have been developed and placed in clinical development. These antibodies generally fall short of satisfactory therapeutic efficacy in improving Alzheimer's disease. A general belief is that if those antibodies are to achieve therapeutic efficacy, a significant portion must get across the BBB to enter the injured sites in the CNS. However, only very minute portions of those antibodies get across the BBB.

Interferon-β-1a (IFN-β-1a) and interferon-β-1b (IFN-β-1b) have been used for the treatment of multiple sclerosis (MS). The pharmaceuticals, IFN-β-1a produced by mammalian cells and IFN-β-1b produced in E. coli, are one-chain protein of 166 amino acid residues containing one disulfide bond. It has been claimed that those therapeutic agents reduce relapse of MS in 18-38% of treated patients. The mechanisms of action of IFN-β-1a and IFN-β-1b are very complex and not completely understood, involving the increased generation of anti-inflammatory immune cells and factors and the down-regulation of pro-inflammatory cells and factors. IFN-β treatment in MS patients also reduces the trafficking of pro-inflammatory T cells across the BBB. It is yet unanswered whether IFN-β-1a and IFN-β-1b mediate their pharmacologic effects in part by getting into the injured sites in the CNS.

When an antibody or protein therapeutic is administered in the body's peripheral, only a very minute amount (about 0.1%) reaches to the CNS, because only a very minute portion of the protein therapeutic gets across the BBB. However, it has also been found that in many diseases of the CNS, including Alzheimer's disease and multiple sclerosis, the inflammation at the diseased sites renders the BBB to breakdown, leading to increased permeability. Therefore, we rationalize that if a larger proportion of an administered antibody specific for β-amyloid or IFN-β-1a and IFN-β-1b is channeled to the BBB, a higher percentage of the therapeutic agents can pass through the BBB and better therapeutic effects can be achieved.

Furthermore, some therapeutic agents have been developed to inhibit the entry of inflammatory immunocytes to across the BBB. A notable example is natalizumab specific for the cell adhesion molecule integrin α4. The antibody functions by inhibiting inflammatory immune cells to attach to and pass through the epithelial layer lining the BBB. While natalizumab has been shown to be therapeutic efficacious, it has serious immunosuppressive side effect. In particular, it causes progressive multifocal leukoencephalopathy, an opportunistic infection caused by John Cunningham virus (JC virus). We therefor rationalize that if a larger proportion of an antibody specific for integrin α4 is recruited to the BBB, a smaller dose will be required, better therapeutic effects can be achieved, and fewer side effects will occur.

The endothelial cells in the capillaries forming the BBB express transferrin receptors and insulin receptors, which mediate the transcytosis of transferrin and insulin molecules, respectively, to the cerebral parenchyma. For using the transferrin receptor as a ferry, only a small proportion gets through while the reaming bulk are trapped or degraded. Because the endothelial cells lining the capillaries in other parts of the vasculature do not express transferrin receptors, the transferrin receptors on the endothelial cells in the BBB can serve as site-specific antigen for recruiting administered therapeutics. Once the therapeutic is concentrated in the BBB, an increased proportion of it will pass through the capillaries.

We also rationalize that when the mechanisms for channeling pharmaceuticals to the BBB is established, anti-inflammatory drugs, such as anti-TNF-α, anti-IL12/IL-23, anti-IL17, and anti-CD3, should be investigated for their therapeutic effects on many types of diseases of the CNS.

For the antibody therapeutic specific for integrin α4, the transferrin receptor is used as a target site recruiter. For Alzheimer disease, the effector moiety can be a few copies of scFv specific for α-amyloid; for treating multiple sclerosis, the effector moiety can be a few copies of IFN-β-1a or IFN-β-1b, or a few copies of scFv specific for integrin α4.

Embodiments of the present disclosure disclose several T-E molecules respectively exist in single multi-arm linker-units or joint-linker configurations, each contains scFv specific for transferrin receptor as the targeting element and IFN-β-1a or IFN-β-1b or scFv specific for integrin α-4 as the effector element. Alternative embodiments disclose T-E molecules respectively exist in single linker-units or joint-linker configurations, each contains scFv specific for transferrin receptor as the targeting element and scFv specific for β-amyloid as the effector element.

Fingolimod is an immunosuppressive drug that is derived from a natural product myriocin originally isolated from certain fungi. Fingolimod has been approved for reducing the relapse of relapsing-remitting multiple sclerosis. Fingolimod is phosphorylated in vivo to form fingolimod-phosphate, which resembles naturally occurring sphingosine-1-phosphate (S1P), an extracellular lipid mediator, and can bind to 4 of the 5 S1P receptors. The S1P receptors are expressed on lymphocytes and involved in lymphocyte migration. A generally pharmacologic mechanism of fingolimod is that it inhibits lymphocytes egress from the lymphoid tissues to the circulation and hence to the CNS. Fingolimod can cross BBB to enter CNS and many cell types in the CNS express S1P receptors, which play roles in cell proliferation, morphology, and migration. It is believed that fingolimod can have direct on the CNS. The administration of fingolimod causes common side effects of headache and fatigue, and severe side effects of skin cancer, macular edema, and fatal infections, such as hemorrhaging focal encephalitis.

A fingolimod molecule has an NH2 group and thus provides a functional group to couple with a bi-functional linker with an NHS group. One preferred embodiment of the present invention is to prepare a T-E construct, which contains a targeting element for delivery to the BBB and a drug bundle of fingolimod as an effector element. For a bundle of fingolimod, 5-10 molecules are incorporated to a linker unit, using either a cleavable linker or non-cleavable linker to conjugate fingolimod molecules to the linking arms of a linker unit. Since fingolimod, after uptake in a patient, is modified to fingolimod phosphate to resemble sphingosine1-phosphate and become active, the drug bundle is alternatively prepared with fingolimod phosphate. A linker unit with fingolimod or fingolimod phosphate bundle is conjugated with 1 or 2 scFv specific for a transferrin receptor I. Upon administration of the molecular construct, a portion of it is carried to the BBB. The fingolimod molecules released from the cleavable linkers pass through the BBB and enter the CNS. Or, a portion of the entire construct enters the CNS. Cleavable linkers can be designed by employing a number of cleaving mechanisms. An installment of S—S bond is often used, since S—S disulfide bond can be cleaved by a reduction reaction at the target tissue site. A peptide bond between amino acids, which is sensitive to proteases, such as matrix metalloproteinases in many tissues and cathepsins in endosomes in target cells, is also commonly used as a cleavable bond in many linker designs.

Some illustrative T-E molecules respectively exist in single linker-units or joint-linker configurations, each contains one or two scFv specific for transferrin receptor as the targeting element and fingolimod as the effector element. In all these molecular constructs, the linkage between the linking arms and the effector elements may be non-cleavable or cleavable bonds. In applying the molecular construct platforms of this invention for the various applications in treating CNS diseases, the targeting moiety can be installed with one or two copies of scFv specific for transferrin receptor or insulin receptor. One or two scFvs specific for transferrin receptor or insulin receptor are used. If the scFv has a relatively high affinity ($Kd<1\times10^{-9}$), 1 scFv is used; if the scFv has modest affinity ($Kd<5\times10^{-8}$ and $>1\times10^{-9}$), 2 scFv are used. It is preferred that no more than 2 copies of scFv specific for transferrin receptor or insulin receptor are used to avoid receptor cross-linking and the endocytosis of the bound drug.

II Infectious Disease

Although large numbers of monoclonal antibodies have been made against components of a various viruses, bacteria, and fungi, which cause serious infectious in humans and animals, few monoclonal antibodies have been developed into preventive treatments or therapeutic agents to counter infections. These shortcomings can be attributed to a few major factors. One major factor is the infectious microorganisms and their products have different serotypes and variable reactivity toward a particular antibody. Another reason is that the targeted microorganisms undergo mutations and escape the targeting of a particular antibody.

The T-E molecular design of the present invention can also be applied for the prevention and treatment of infectious diseases. The plurality of the linking arms can enhance the avidity and specificity of binding to target infectious microorganisms or their products and elicit immune functions to facilitate the clearance of the microorganisms and their products. We reason that the avidity enhancement and the recruitment of immune clearance function can somehow overcome the serotypic difference and mutational problems. Such improvements should increase the efficacy of the candidate antibodies for the prevention and therapy of infectious diseases. Many antibodies, which have failed to meet expectation in clinical trials, may be configured with the present invention and re-investigated.

A preferred set of embodiment of the present invention is to employ joint-linkers configuration with one linker-unit for targeting and one linker-unit for recruiting effector function. An alternative set of preferred embodiment is to employ single linker-units with multiple linking arms for targeting elements and a coupling arm for an effector element. The targeting elements may be one of the two categories: (1) scFv or sdAb specific for a surface component of a microorganism or its product, e.g., envelope protein gp120 of human immunodeficiency virus type 1 (HIV-1), F protein of respiratory syncytia virus (RSV), a surface antigen of *Clostridium difficile* or *Staphylococcus aureus*, or endotoxin of Gram-negative bacteria or Shiga-like toxin of *Escherichia coli*, or (2) the extracellular portions of cell surface receptors of viruses, such as the HIV-1 gp120-binding CD4 domain.

The effector elements are 1 or 2 scFv or sdAb specific for one Fc receptor of IgG, e.g. FcγRIIA (CD32), FcγRIIIB (CD16b), or FcγRI (CD64). Those receptors are expressed on neutrophils, macrophages, and eosinophils and are the key molecules mediating phagocytosis of antibody-bound microorganisms. FcγRIIA and FcγRIIIB bind to IgG with low affinity (Kd in the range of $10^{-6}$ to $10^{-7}$), and FcγRI binds to IgG1 and IgG3 with high affinity (Kd $10^{-9}$). It is advantageous to employ scFv or sdAb specific for FcγRIIA or FcγRIIIB, because they can compete favorably with IgG in binding to the receptors.

The antibodies specific for carbohydrate antigens on bacterial surface are usually weak in binding affinity and are expressed in IgM rather than IgG. An IgM molecule has 10 Fv's (antigen-binding sites). However, an IgM molecule, which has a molecular weight of about 1000 kd, cannot cross capillaries and reach to extravascular space. With the configuration of the present invention, a molecular construct carrying 6 scFv or 10 sdAb will have a molecular weight of about 150 kd.

In employing antibody-based therapeutics for clearing viruses, it is important that the therapeutic does not lead to FcR-mediated enhancement of viral infection. In those cases, the bound viral particles are not phagocytosed and digested. Some viruses, such as Dengue virus can multiply in phagocytes. Thus, if the viral particles gain access to a cell and enter the bound cells without being destroyed, the virus can multiply in the infected cells. Therefore, a set of preferred embodiments of this invention is that the molecular construct contains 2 or more scFv specific for an Fcγ receptor and can bind to multiple Fcγ receptor molecules on phagocyte cell surface, so that the bound viral particles are destined to phagocytosis pathway.

Among the many antibodies specific for viruses, bacteria, or their products, which have been in clinical trials, only antibodies specific for RSV have been approved for clinical uses. Even for antibodies against RSV, they are only approved for prevention, and not for treatment of on-going infection. It is desirable that an anti-RSV antibody can be developed for treating already-infected subjects. The other antibodies are still in clinical development or have failed in clinical trials. With the molecular construct platforms of this invention, all of these antibodies can be employed for improved efficacy. A partial list of those antibodies are:

(1) Palivizumab and felvizumab specific for RSV F protein
(2) Suvizumab specific for HIV-1 gp120
(3) Libivirumab, exbivirumab, tuvirumab specific for hepatitis B surface antigen (HBsAg) of HBV
(4) CR6261 mAb, diridavumab, and firivumab specific for hemagglutinin A of influenza A virus
(5) Regavirumab and sevirumab specific for glycoprotein of cytomegalovirus
(6) Rafivirumab specific for glycoprotein of rabies virus
(7) Actoxumab and bezlotoxumab specific for surface antigen of *Clostridium difficile*
(8) Obiltoxaximab and raxibacumab specific for *Bacillus anthracis* anthrax
(9) Panobacumab (human IgM monoclonal antibody) specific for *Pseudomonas aeruginosa* serotype IATS O11
(10) Tefibazumab and tosatoxumab specific for clumping factor A of *Staphylococcus aureus*
(11) Edobacomab specific for endotoxin of Gram-negative bacteria for treating sepsis
(12) Pagibaximab specific for lipoteichoic acid of *staphylococcus areus* for treating staphylococcal sepsis
(13) Raxibacumab (human monoclonal antibody) specific anthrax toxin
(14) Pritoxaximab, setoxaximab, and urtoxazumab specific for Shiga-like toxin type I or II of *Escherichia coli*.

According to several embodiments of the present disclosure, T-E molecules in joint-linker configurations for treating infectious diseases incorporate scFv specific for the F protein of respiratory syncytia virus (RSV) or gp120 of human immunodeficiency virus type 1 (HIV-1) as targeting/capture elements and scFv specific for FcγRIIA (CD32) or FcγRIIIB (CD16b) as effector/clearance elements. According to embodiments of the present disclosure, some T-E molecules in single linker-units or joint linkers configuration incorporate scFv specific for endotoxin of Gram(−) bacteria or lipoteichoic acid of *Staphylococcus* areus as targeting/capture elements and scFv specific for CD32 or CD16b as effector/clearance elements. An accelerated removal of endotoxin during Gram(−) bacterial infection should decrease the amplitude of cytokine release, such as TNF-α, IL-1 etc., (i.e. cytokine storm) in a life-threatening septic condition. In applying the molecular construct platform of this invention for the various applications in treating infectious diseases, the effector moiety can be installed with one or two copies of scFv specific for transferrin receptor. One or two scFvs specific for CD32 (CD32a or CD32b) or CD16b are used. If the scFv has a relatively high affinity (Kd<1×10$^{-9}$), 1 scFv is used; if the scFv has modest affinity (Kd<5×10$^{-8}$ and >1×10$^{-9}$), 2 scFv are used. It is preferred that no more than 2 copies of scFv specific for CD32 or CD16b are used to avoid receptor cross-linking and the endocytosis of the bound drug.

PART I Multi-Arm Linkers for Treating Specific Diseases

I-(i) Peptide Core for Use in Multi-Arm Linker

The first aspect of the present disclosure pertains to a linker unit that comprises, (1) a center core that comprises 2-15 lysine (K) residues, and (2) 2-15 linking arms respectively linked to the K residues of the center core. The present center core is characterized in having or being linked with an azide group, an alkyne group, a tetrazine group, or a strained alkyne group at its N- or C-terminus.

In the preparation of the present linker unit, a PEG chain having a N-hydroxysuccinimidyl (NHS) group at one terminus and a functional group (e.g., an NHS, a maleimide, an azide, an alkyne, a tetrazine, or a strained alkyne group) at the other terminus is linked to the K residue of the center core by forming an amide bond between the NHS group of the PEG chain and the amine group of the K residue. In the present disclosure, the PEG chain linked to the K residue is referred to as a linking arm, which has a functional group at the free-terminus thereof.

According to the embodiments of the present disclosure, the center core is a polypeptide that has 8-120 amino acid residues in length and comprises 2 to 15 lysine (K) residues, in which each K residue and the next K residue are separated by a filler sequence.

According to embodiments of the present disclosure, the filler sequence comprises glycine (G) and serine (S) residues; preferably, the filler sequence consists of 2-15 residues selected from G, S, and a combination thereof. For example, the filler sequence can be,

GS,

GGS,

GSG,

| GGGS, | (SEQ ID NO: 1) |
|---|---|
| GSGS, | (SEQ ID NO: 2) |
| GGSG, | (SEQ ID NO: 3) |
| GSGGS, | (SEQ ID NO: 4) |
| SGGSG, | (SEQ ID NO: 5) |
| GGGGS, | (SEQ ID NO: 6) |
| GGSGGS, | (SEQ ID NO: 7) |
| GGSGGSG, | (SEQ ID NO: 8) |
| SGSGGSGS, | (SEQ ID NO: 9) |
| GSGGSGSGS, | (SEQ ID NO: 10) |
| SGGSGGSGSG, | (SEQ ID NO: 11) |
| GGSGGSGGSGS, | (SEQ ID NO: 12) |
| SGGSGGSGSGGS, | (SEQ ID NO: 13) |
| GGGGSGGSGGGGS, | (SEQ ID NO: 14) |
| GGGSGSGSGSGGGS, or | (SEQ ID NO: 15) |
| SGSGGGGSGGSGSG. | (SEQ ID NO: 16) |

The filler sequence placed between two lysine residues may be variations of glycine and serine residues in somewhat random sequences and/or lengths. Longer fillers may be used for a polypeptide with fewer lysine residues, and shorter fillers for a polypeptide with more lysine residues. Hydrophilic amino acid residues, such as aspartic acid and histidine, may be inserted into the filler sequences together with glycine and serine. As alternatives for filler sequences made up with glycine and serine residues, filler sequences may also be adopted from flexible, soluble loops in common human serum proteins, such as albumin and immunoglobulins.

According to certain preferred embodiments of the present disclosure, the center core comprises 2-15 units of the sequence of $G_{1-5}SK$. Alternatively, the polypeptide comprises the sequence of $(GSK)_{2-15}$; that is, the polypeptide comprises at least two consecutive units of the sequence of GSK. For example, the present center core may comprises the amino acid sequence of the following,

| Ac-CGGSGGSGGSKGSGSK, | (SEQ ID NO: 17) |
|---|---|
| Ac-CGGSGGSGGSKGSGSKGSK, or | (SEQ ID NO: 18) |
| Ac-CGSKGSKGSKGSKGSKGSKGSKGSKGSKGSK, | (SEQ ID NO: 19) | in which Ac represents the acetyl group.

According to certain embodiments of the present disclosure, the center core is a polypeptide that comprises the sequence of $(X_{aa}—K)_n$, in which $X_{aa}$ is a PEGylated amino acid having 2 to 12 repeats of ethylene glycol (EG) unit, and n is an integral from 2 to 15.

As described above, the present center core is characterized in having or being linked with an azide group, an alkyne group, a tetrazine group, or a strained alkyne group at its N- or C-terminus. According to some embodiments of the present disclosure, the present center core comprises, at its N- or C-terminus, an amino acid residue having an azide group or an alkyne group. The amino acid residue having an azide group can be, L-azidohomoalanine (AHA), 4-azido-L-phenylalanine, 4-azido-D-phenylalanine, 3-azido-L-alanine, 3-azido-D-alanine, 4-azido-L-homoalanine, 4-azido-D-homoalanine, 5-azido-L-ornithine, 5-azido-d-ornithine, β-azido-L-lysine, or β-azido-D-lysine. For example, the present center core may have the sequence of, Ac-$(GSK)_{2-7}$-$(G_{2-4}S)_{1-8}$-$A^{AH}$, Ac-$A^{AH}$-$(SG_{2-4})_{1-8}$-$(GSK)_{2-7}$, Ac-$A^{AH}$-$(SG_{2-4})_{0-7}$-$(GSK)_{2-6}$-$(G_{2-4}S)_{1-8}$—C, Ac—C—$(SG_{2-4})_{0-7}$-$(GSK)_{2-6}$-$(G_{2-4}S)_{1-8}$-$A^{AH}$, Ac—K-$(Xaa_{2-12}$-K$)_{2-4}$-$Xaa_{2-12}$-$A^{AH}$, Ac-$A^{AH}$-$Xaa_{2-12}$-K-$(Xaa_{2-12}$-K$)_{2-4}$, Ac-$A^{AH}$-$Xaa_{2-12}$-K-$(Xaa_{2-12}$-K$)_{1-3}$-$Xaa_{2-12}$-C, or Ac—C-$Xaa_{2-12}$-K-$(Xaa_{2-12}$-K$)_{1-3}$-$Xaa_{2-12}$-$A^{AH}$, in which Xaa is a PEGylated amino acid having specified repeats of EG unit, Ac represents the acetyl group, and $A^{AH}$ represents the AHA residue.

Exemplary amino acid having an alkyne group includes, but is not limited to, L-homopropargylglycine (L-HPG), D-homopropargylglycine (D-HPG), or beta-homopropargylglycine (β-HPG). In this case, the present center core may have the sequence of, Ac-(GSK)$_{2-7}$-(G$_{2-4}$S)$_{1-8}$-G$^{HP}$,
Ac-G$^{HP}$-(SG$_{2-4}$)$_{1-8}$-(GSK)$_{2-7}$,
Ac-G$^{HP}$-(SG$_{2-4}$)$_{0-7}$-(GSK)$_{2-6}$-(G$_{2-4}$S)$_{1-8}$—C,
Ac—C—(SG$_{2-4}$)$_{0-7}$-(GSK)$_{2-6}$-(G$_{2-4}$S)$_{1-8}$-G$^{HP}$,
Ac—K-(Xaa$_{2-12}$-K)$_{2-4}$-Xaa$_{2-12}$-G$^{HP}$,
Ac-G$^{HP}$-Xaa$_{2-12}$-K-(Xaa$_{2-12}$-K)$_{2-4}$,
Ac-G$^{HP}$-Xaa$_{2-12}$-K-(Xaa$_{2-12}$-K)$_{1-3}$-Xaa$_{2-12}$-C, or
Ac—C-Xaa$_{2-12}$-K-(Xaa$_{2-12}$-K)$_{1-3}$-Xaa$_{2-12}$-G$^{HP}$, in which Xaa is a PEGylated amino acid having specified repeats of EG unit, Ac represents the acetyl group, and G$^{HP}$ represents the HPG residue.

It is noted that many of the amino acids containing an azide or alkyne group in their side chains and PEGylated amino acids are available commercially in t-boc (tert-butyloxycarbonyl)- or Fmoc (9-fluorenylmethyloxycarbonyl)-protected forms, which are readily applicable in solid-phase peptide synthesis.

According to some working examples of the present disclosure, the center core may comprise the sequence of, Ac-G$^{HP}$GGSGGSGGSKGSGSK, (SEQ ID NO: 21)

Ac-G$^{HP}$GGSGGSGGSKGSGSKGSK, (SEQ ID NO: 22)

Ac-A$^{AH}$GGSGGSGGSKGSGSKGSK, (SEQ ID NO: 23)

Ac-G$^{HP}$GGSGGSGGSKGSGSKGSGSC, (SEQ ID NO: 24)

Ac-C-Xaa$_2$-K-Xaa$_2$-K-Xaa$_2$-K, (SEQ ID NO: 25)
or

Ac-C-Xaa$_6$-K-Xaa$_6$-K-Xaa$_6$-K-Xaa$_6$-K-Xaa$_6$-K, (SEQ ID NO: 26)

in which Xaa is a PEGylated amino acid having specified repeats of EG unit, Ac represents the acetyl group, $A^{AH}$ represents the AHA residue, and G$^{HP}$ represents the HPG residue.

Alternatively, the present center core is linked with a coupling arm, which has a functional group (e.g., an azide group, an alkyne group, a tetrazine group, or a strained alkyne group) at the free-terminus thereof (that is, the terminus that is not linked to the center core). In these cases, the present center core comprises a cysteine residue at its N- or C-terminus. To prepare a linker unit linked with a coupling arm, a PEG chain having a maleimide group at one terminus and a functional group at the other terminus is linked to the cysteine residue of the center core via thiol-maleimide reaction occurred between the maleimide group of the PEG chain and the thiol group of the cysteine residue. In the present disclosure, the PEG chain linked to the cysteine residue of the center core is referred to as the coupling arm, which has a functional group at the free-terminus thereof.

Preferably, the coupling arm has a tetrazine group or a strained alkyne group (e.g., a cyclooctene or cyclooctyne group) at the free-terminus thereof. These coupling arms have 2-12 EG units. According to the embodiments of the present disclosure, the tetrazine group is 1,2,3,4-tetrazine, 1,2,3,5-tetrazine, 1,2,4,5-tetrazine, or derivatives thereof. The strained alkyne group may be a cyclooctene or a cyclooctyne group. According to the working examples of the present disclosure, the cyclooctene group is a trans-cyclooctene (TCO) group; example of cyclooctyne group includes, but is not limited to, dibenzocyclooctyne (DBCO), difluorinated cyclooctyne (DIFO), bicyclononyne (BCN), and dibenzocyclooctyne (DICO). According to some embodiments of the present disclosure, the tetrazine group is β-methyl-tetrazine.

Example of the present center core configured to be linked with the coupling arm includes, but is not limited to, Ac-(GSK)$_{2-7}$-(G$_{2-4}$S)$_{1-8}$—C-Xaa$_{2-12}$-tetrazine,
Ac-(GSK)$_{2-7}$-(G$_{2-4}$S)$_{1-8}$—C-Xaa$_{2-12}$-strained alkyne,
Ac—K-(Xaa$_{2-12}$-K)$_{2-4}$-Xaa$_{2-12}$-C-Xaa$_{2-12}$-tetrazine,
Ac—K-(Xaa$_{2-12}$-K)$_{2-4}$-Xaa$_{2-12}$-C-Xaa$_{2-12}$-strained alkyne,
Tetrazine-Xaa$_{2-12}$-C(Ac)—(SG$_{2-4}$)$_{1-8}$-(GSK)$_{2-7}$,
Strained alkyne-Xaa$_{2-12}$-C(Ac)—(SG$_{2-4}$)$_{1-8}$-(GSK)$_{2-7}$,
Tetrazine-Xaa$_{2-12}$-C(Ac)-Xaa$_{2-12}$-K-(Xaa$_{2-12}$-K)$_{2-4}$, and
Strained alkyne-Xaa$_{2-12}$-C(Ac)-Xaa$_{2-12}$-K-(Xaa$_{2-12}$-K)$_{2-4}$.

Alternatively, the center core has an azide or alkyne group at one terminus and a coupling arm with tetrazine or strained alkyne group at the other terminus. Examples are the following:

Ac-A$^{AH}$-(SG$_{2-4}$)$_{0-7}$-(GSK)$_{2-6}$-(G$_{2-4}$S)$_{1-8}$—C-Xaa$_{2-12}$-tetrazine,
Ac-A$^{AH}$-(SG$_{2-4}$)$_{0-7}$-(GSK)$_{2-6}$-(G$_{2-4}$S)$_{1-8}$—C-Xaa$_{2-12}$-strained alkyne,
Tetrazine-Xaa$_{2-12}$-C(Ac)—(SG$_{2-4}$)$_{0-7}$-(GSK)$_{2-6}$-(G$_{2-4}$S)$_{1-8}$-A$^{AH}$,
Strained alkyne-Xaa$_{2-12}$-C(Ac)—(SG$_{2-4}$)$_{0-7}$-(GSK)$_{2-6}$-(G$_{2-4}$S)$_{1-8}$-A$^{AH}$,
Ac-A$^{AH}$-Xaa$_{2-12}$-K-(Xaa$_{2-12}$-K)$_{1-3}$-Xaa$_{2-12}$-C-Xaa$_{2-12}$-tetrazine,
Ac-A$^{AH}$-Xaa$_{2-12}$-K-(Xaa$_{2-12}$-K)$_{1-3}$-Xaa$_{2-12}$-C-Xaa$_{2-12}$-strained alkyne,
Tetrazine-Xaa$_{2-12}$-C(Ac)-Xaa$_{2-12}$-K-(Xaa$_{2-12}$-K)$_{1-3}$-Xaa$_{2-12}$-A$^{AH}$,
Strained alkyne-Xaa$_{2-12}$-C(Ac)-Xaa$_{2-12}$-K-(Xaa$_{2-12}$-K)$_{1-3}$-Xaa$_{2-12}$-A$^{AH}$,
Ac-G$^{HP}$-(SG$_{2-4}$)$_{0-7}$-(GSK)$_{2-6}$-(G$_{2-4}$S)$_{1-8}$—C-Xaa$_{2-12}$-tetrazine,
Ac-G$^{HP}$-(SG$_{2-4}$)$_{0-7}$-(GSK)$_{2-6}$-(G$_{2-4}$S)$_{1-8}$—C-Xaa$_{2-12}$-strained alkyne,
Tetrazine-Xaa$_{2-12}$-C(Ac)—(SG$_{2-4}$)$_{0-7}$-(GSK)$_{2-6}$-(G$_{2-4}$S)$_{1-8}$-G$^{HP}$,
Strained alkyne-Xaa$_{2-12}$-C(Ac)—(SG$_{2-4}$)$_{0-7}$-(GSK)$_{2-6}$-(G$_{2-4}$S)$_{1-8}$-G$^{HP}$,
Ac-G$^{HP}$-Xaa$_{2-12}$-K-(Xaa$_{2-12}$-K)$_{1-3}$-Xaa$_{2-12}$-C-Xaa$_{2-12}$-tetrazine,
Ac-G$^{HP}$-Xaa$_{2-12}$-K-(Xaa$_{2-12}$-K)$_{1-3}$-Xaa$_{2-12}$-C-Xaa$_{2-12}$-strained alkyne,
Tetrazine-Xaa$_{2-12}$-C(Ac)-Xaa$_{2-12}$-K-(Xaa$_{2-12}$-K)$_{1-3}$-Xaa$_{2-12}$-G$^{HP}$, and
Strained alkyne-Xaa$_{2-12}$-C(Ac)-Xaa$_{2-12}$-K-(Xaa$_{2-12}$-K)$_{1-3}$-Xaa$_{2-12}$-G$^{HP}$.

The polypeptide may also be synthesized using recombinant technology by expressing designed gene segments in bacterial or mammalian host cells. It is preferable to prepare the polypeptide as recombinant proteins if the core has high numbers of lysine residues with considerable lengths. As the length of a polypeptide increases, the number of errors increases, while the purity and/or the yield of the product decrease, if solid-phase synthesis was adopted. To produce a polypeptide in bacterial or mammalian host cells, a filler sequence ranges from a few amino acid residues to 10-20 residues may be placed between two K residues. Further, since AHA and HPG are not natural amino acids encoded by the genetic codes, the N-terminal or C-terminal residue for those recombinant polypeptides is cysteine. After the recombinant proteins are expressed and purified, the terminal cysteine residue is then reacted with short bifunctional cross-linkers, which have maleimide group at one end, which reacts with SH group of cysteine residue, and alkyne, azide, tetrazine, or strained alkyne at the other end.

The synthesis of a polypeptide using PEGylated amino acids involves fewer steps than that with regular amino acids such as glycine and serine resides. In addition, PEGylated amino acids with varying lengths (i.e., numbers of repeated ethylene glycol units) may be employed, offering flexibility for solubility and spacing between adjacent amino groups of lysine residues. In addition to PEGylated amino acids, the center cores may also be constructed to comprise artificial amino acids, such as D-form amino acids, homo-amino acids, N-methyl amino acids, etc. Preferably, the PEGylated amino acids with varying lengths of polyethylene glycol (PEG) are used to construct the center core, because the PEG moieties contained in the amino acid molecules provide conformational flexibility and adequate spacing between conjugating groups, enhance aqueous solubility, and are generally weakly immunogenic. The synthesis of PEGylated amino acid-containing center core is similar to the procedures for the synthesis of regular polypeptides.

Optionally, for stability purpose, the present center core has an acetyl group to block the amino group at its N-terminus.

As could be appreciated, the number of the linking arms linked to the center core is mainly determined by the number of lysine resides comprised in the center core. Since there are at least two lysine residues comprised in the present center core, the present linker unit may comprise a plurality of linking arms.

Reference is now made to FIG. 1A. As illustrated, the linker unit 10A comprises a center core 11a comprising one HPG ($G^{HP}$) residue and four lysine (K) residues respectively separated by filler sequences (denoted by the dots throughout the drawings). The filler sequences between the HPG residue and K residue or between any two K residues may comprise the same or different amino acid sequences. In this example, four linking arms 20a-20d are linked to the lysine residues by forming an amide linkage between the NHS group and the amine group of the lysine residue, respectively. As could be appreciated, certain features discussed above regarding the linker unit 10A or any other following linker units are common to other linker units disclosed herein, and hence some or all of these features are also applicable in the following examples, unless it is contradictory to the context of a specific embodiment. However, for the sake of brevity, these common features may not be explicitly repeated below.

Figure 1B:
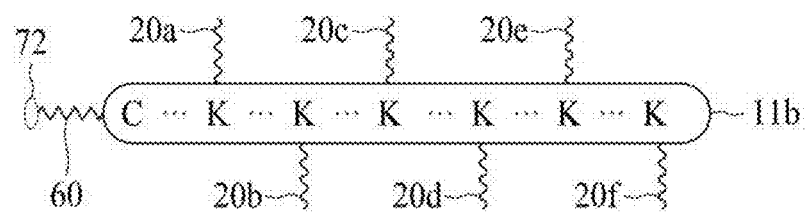

FIG. 1B provides a linker unit 10B according to another embodiment of the present disclosure. The center core 11b comprises one cysteine (C) residue and six lysine (K) residues respectively separated by the filler sequences. In this example, the linker unit 10B comprises six linking arms 20a-20f that are respectively linked to the lysine residues. According to the embodiments of the present disclosure, the linking arm is a PEG chain having 2-20 repeats of EG units.

Unlike the linker unit 10A of FIG. 1A, the linker unit 1B further comprises a coupling arm 60. As discussed above, a PEG chain having a maleimide group at one end and a functional group at the other end is used to form the coupling arm 60. In this way, the coupling arm 60 is linked to the cysteine residue of the center core 11b via thiol-maleimide reaction. In this example, the functional group at the free terminus of the coupling arm 60 is a tetrazine group 72. According to the embodiments of the present disclosure, the coupling arm is a PEG chain having 2-12 repeats of EG units.

Figure 1C:
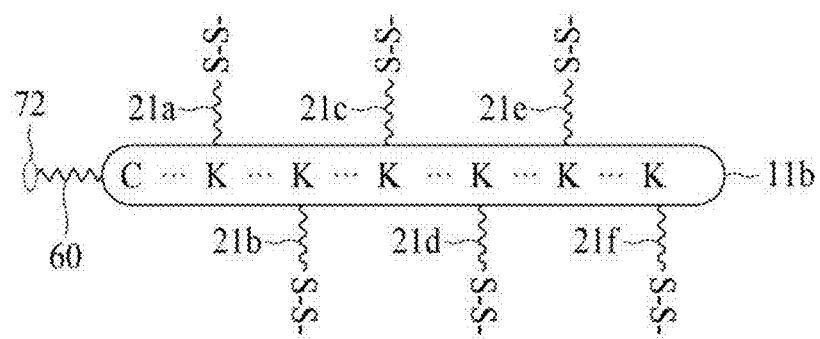

When the release of effector elements at the targeted site is required, a cleavable bond can be installed in the linking arm. Such a bond is cleaved by acid/alkaline hydrolysis, reduction/oxidation, or enzymes. One embodiment of a class of cleavable PEG chains that can be used to form the coupling arm is NHS-$PEG_{2-20}$-S—S-maleimide, where S—S is a disulfide bond that can be slowly reduced, while the NHS group is used for conjugating with the amine group of the center core, thereby linking the PEG chain onto the center core. The maleimide group at the free terminus of the linking arm may be substituted by an azide, alkyne, tetrazine, or strained alkyne group. According to some embodiments of the present disclosure, the linking arm is a PEG chain, which has 2-20 repeats of EG units with a disulfide linkage at the free terminus thereof (i.e., the terminus that is not linked with the center core). Reference is now made to FIG. 1C, in which each of the five linking arms 21a-21f respectively linked to the K resides of the center core 11b is a PEG chain with a disulfide linkage at the free terminus of the linking arm.

According to the embodiments of the present disclosure, the linking arm linked to the K residue of the center core has a functional group (i.e., a maleimide, an NHS, an azide, an alkyne, a tetrazine, or a strained alkyne group) at its free terminus. Preferably, when the free terminus of the linking arm is an azide, alkyne, or cyclooctyne group, then the amino acid residue at the N- or C-terminus of the center core is a cysteine residue, and the free terminus of the coupling arm is a tetrazine or cyclooctene group. Alternatively, when the free terminus of the linking arm is a tetrazine group or cyclooctene group, then the amino acid residue at the N- or C-terminus of the center core has an azide or alkyne group, or the amino acid residue at the N- or C-terminus of the center core is a cysteine residue, and the free terminus of the coupling arm is an azide, the alkyne, or the cyclooctyne group Depending on the functional group (i.e., a maleimide, an NHS, an azide, an alkyne, a tetrazine, or a strained alkyne group) present at the free terminus of the linking arm, it is feasible to design a functional element (such as, a targeting element, an effector element, or an element for improving the pharmacokinetic property) with a corresponding functional group, so that the functional element may linked to the free terminus of the linking arm via any of the following chemical reactions, (1) forming an amide bond therebetween: in this case, the linking arm has an NHS group at the free terminus, and the functional element has an amine group;

(2) the thiol-maleimide reaction: in this case, the linking arm has a maleimide group at the free terminus, and the functional element has an thiol group;

(3) the Copper(I)-catalyzed alkyne-azide cycloaddition reaction (CuAAC reaction, or the "click" reaction for short): one of the free terminus of the linking arm and the functional element has an azide group, while the other has an alkyne group; the CuAAC reaction is exemplified in Scheme 1;

(4) the inverse electron demand Diels-Alder (iEDDA) reaction: one of the free terminus of the linking arm and the functional element has a tetrazine group, while the other has a cyclooctene group; the iEDDA reaction is exemplified in Scheme 2; or (5) the strained-promoted azide-alkyne click chemistry (SPAAC) reaction: one of the free terminus of the linking arm and the functional element has an azide group, while the other has an cyclooctyne group; the SPAAC reaction is exemplified in Scheme 3.

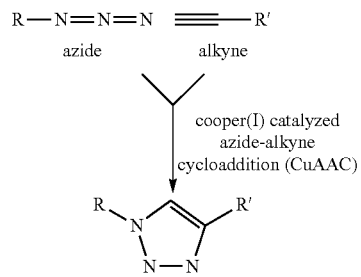

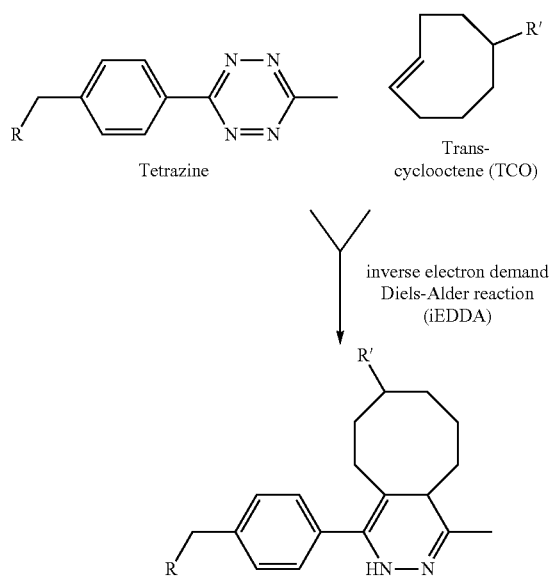

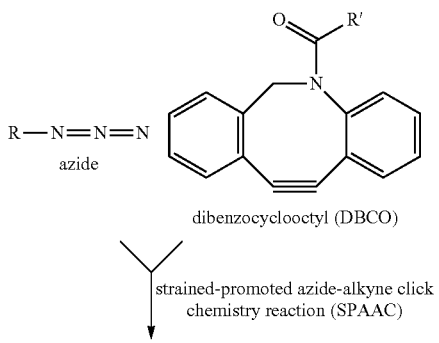

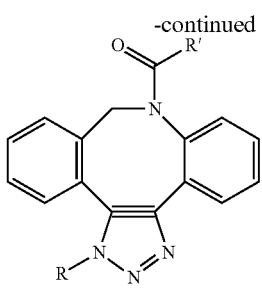

The CuAAC reaction yields 1,5 di-substituted 1,2,3-triazole. The reaction between alkyne and azide is very selective and there are no alkyne and azide groups in natural biomolecules. Furthermore, the reaction is quick and pH-insensitive. It has been suggested that instead of using copper (I), such as cuprous bromide or cuprous iodide, for catalyzing the click reaction, it is better to use a mixture of copper (II) and a reducing agent, such as sodium ascorbate to produce copper (I) in situ in the reaction mixture. Alternatively, the second element can be linked to the N- or C-terminus of the present center core via a copper-free reaction, in which pentamethylcyclopentadienyl ruthenium chloride complex is used as the catalyst to catalyze the azide-alkyne cycloaddition.

For the sake of illustration, the functional elements linked to the linking arms are referred to as the first elements. As could be appreciated, the number of the first elements carried by the present linker unit depends on the number of K residues of the center core (and thus, the number of the linking arms). Accordingly, one of ordinary skill in the art may adjust the number of the first elements of the linker unit as necessary, for example, to achieve the desired targeting or therapeutic effect.

Figure 1D:
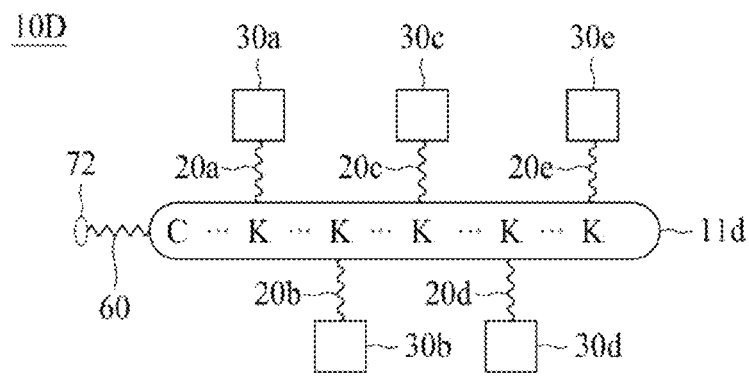

An example of a linker unit 10D having the first elements is illustrated FIG. 1D. Other than the features discussed hereafter, FIG. 1D is quite similar to FIG. 1B. First, there are five K residues in the center core 11*d*, and accordingly, five linking arms 20*a*-20*e* are linked thereto, respectively. Second, the linker unit 10D has five first elements 30*a*-30*e* linked to each of the linking arms 20*a*-20*e*. As discussed below, the optional tetrazine group 72 allows for the conjugation with an additional functional element, another molecular construct (see, Part II or Part III below).

Figure 1E:
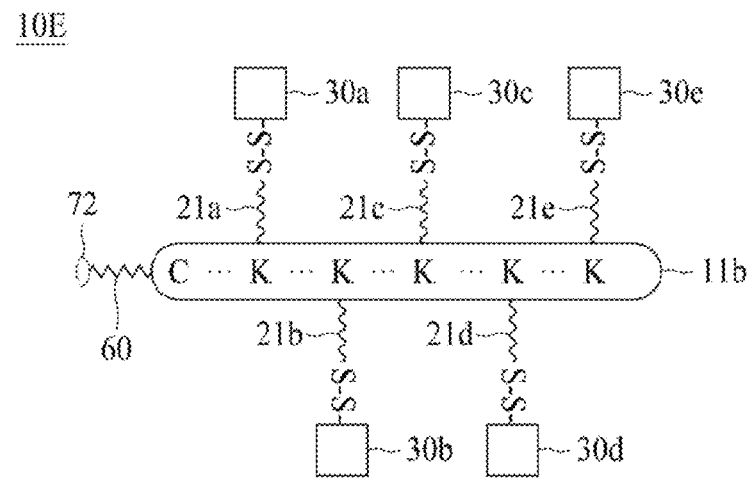

FIG. 1E provides an alternative example, in which the linker unit 10E has a similar structure with the linker unit 1D, except that each of the linker arms 21*a*-21*e* has a disulfide linkage at the element-linking terminus thereof (i.e., the terminus that is linked with each of the first elements 30*a*-30*e*).

Alternatively, the present linker unit further comprises a plurality connecting arms, each of which has a functional group (i.e., a maleimide, an NHS, an azide, an alkyne, a tetrazine, or a strained alkyne group) at one terminus, and an NHS or a maleimide group at the other terminus. Using a reaction that is similar to those occurred between the first element and the linking arm, the connecting arm may be linked to the linking arm with the corresponding functional group either via forming an amide bond therebetween, or via the thiol-maleimide, CuAAC, iEDDA or SPAAC reaction. The connecting arm linked to the linking arm thus has the NHS or the maleimide group at its free terminus (or the element-linking terminus; i.e., the terminus that is not linked with the linking arm); then, the first element is linked to the element-linking terminus of the connecting arm via forming an amide bond therebetween or via the thiol-maleimide reaction.

Figure 1F:
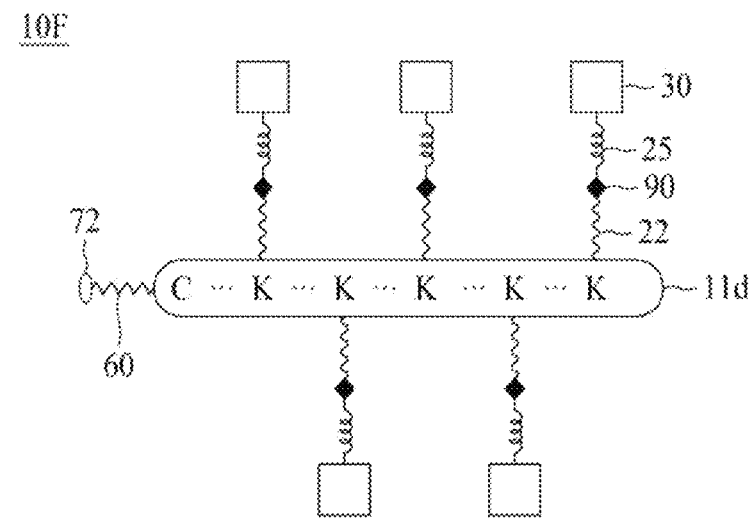

Reference is now made to FIG. 1F, in which the linking arm is linked to the K residue of the center core 11d as described in FIG. 1D. Compared with the linker unit 10D, the linker unit 10F further comprises a connecting arm 25, which is linked to the linking arms 22 via the SPAAC reaction. Then, the first element 30 is linked to the connecting arm 25 either via forming the amide bond therebetween or via the thiol-maleimide reaction. The diamond 90 as depicted in FIG. 1F represents the chemical bond resulted from the SPAAC reaction occurred between the linking arm 22 and the connecting arm 25.

According to some embodiments of the present disclosure, the connecting arm is a PEG chain having 2-20 repeats of EG units. Alternatively, the connecting arm is a PEG chain having 2-20 repeats of EG units with a disulfide linkage at the element-linking terminus thereof (i.e., the free terminus that is not linked with the linking arm).

In one working example, the connecting arm has three repeats of EG units, as well as a disulfide linkage at the free terminus (also referred to as the element-linking terminus) of the connecting arm. In this case, the first element linked to the element-linking terminus of the connecting arm can be efficiently released from the present linker unit by the treatment of a reductant.

According to some preferred embodiments of the present disclosure, the first elements is fingolimod, fingolimod phosphate, interferon-β, or a single-chain variable fragment (scFv) specific for integrin-α4, β-amyloid, a viral protein, a bacterial protein.

Non-limiting viral protein includes F protein of respiratory syncytia virus (RSV), gp120 protein of human immunodeficiency virus type 1 (HIV-1), hemagglutinin A (HA) protein of influenza A virus, and glycoprotein of cytomegalovirus.

Example of the bacterial protein includes, but is not limited to, the endotoxin of Gram(–) bacteria, the surface antigen of *Clostridium difficile*, the lipoteichoic acid of *Saphylococcus aureus*, the anthrax toxin of *Bacillus anthracis*, or the Shiga-like toxin type I or II of *Escherichia coli*.

In order to increase the intended or desired effect (e.g., the therapeutic effect), the present linker unit may further comprise a second element in addition to the first element. For example, the second element can be either a targeting element or an effector element. In optional embodiments of the present disclosure, the first element is an effector element, while the second element may be another effector element, which works additively or synergistically with or independently of the first element. Still optionally, the first and second elements exhibit different properties; for example, the first element is a targeting element, and the second element is an effector element, and vice versa. Alternatively, the first element is an effector element, and the second element is an element capable of improving the pharmacokinetic property of the linker unit, such as solubility, clearance, half-life, and bioavailability. The choice of a particular first element and/or second element depends on the intended application in which the present linker unit (or multi-arm linker) is to be used. Examples of these functional elements are discussed below in Part I-(iii) of this specification.

Structurally, the second element is linked to the azide, alkyne, tetrazine, or strained alkyne group at the N- or C-terminus of the center core. Specifically, the second element may be optionally conjugated with a short PEG chain (preferably having 2-12 repeats of EG units) and then linked to the N- or C-terminal amino acid residue having an azide group or an alkyne group (e.g., AHA residue or HPG residue). Alternatively, the second element may be optionally conjugated with the short PEG chain and then linked to the coupling arm of the center core.

According to some embodiments of the present disclosure, the center core comprises an amino acid having an azide group (e.g., the AHA residue) at its N- or C-terminus; and accordingly, a second element having an alkyne group is linked to the N- or C-terminus of the center core via the CuAAC reaction. According to other embodiments of the present disclosure, the center core comprises an amino acid having an alkyne group (e.g., the HPG residue) at its N- or C-terminus; and a second element having an azide group is thus capable of being linked to the N- or C-terminus of the center core via the CuAAC reaction.

Figure 1G:
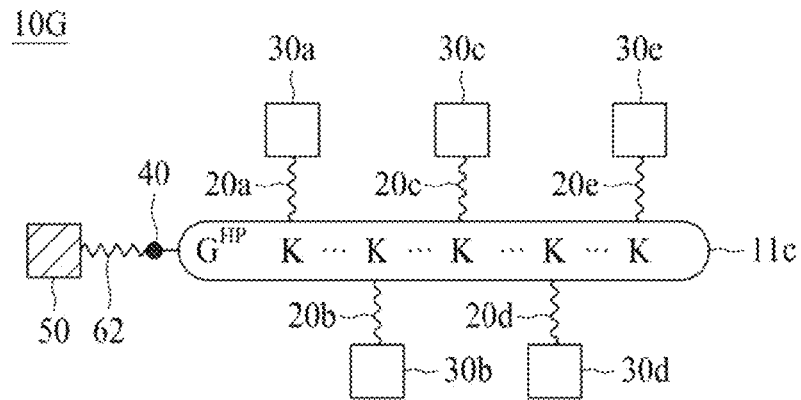

FIG. 1G provides an example of the present linker unit 10G carrying a plurality of first elements and one second element. In this example, the center core 11c comprises one HPG (G$^{HP}$) residue and five lysine (K) residues. Five linking arms 20a-20e are respectively linked to the five K residues of the center core 11c; and five first elements 30a-30e are respectively linked to said five linking arms 20a-20e via the thiol-maleimide reaction. In addition to the first elements, the linker unit 10G further comprises one second element 50 that is linked to one end of a short PEG chain 62. Before being conjugated with the center core 11c, the other end of the short PEG chain 62 has an azide group. In this way, the azide group may reacted with the HPG residue that having an alkyne group via CuAAC reaction, so that the second element 50 is linked to the center core 11c. The solid dot 40 depicted in FIG. 1G represents the chemical bond resulted from the CuAAC reaction occurred between the HPG residue and the azide group.

Alternatively, the second element is linked to the center core via a coupling arm. According to certain embodiments of the present disclosure, the coupling arm has a tetrazine group, which can be efficiently linked to a second element having a TCO group via the iEDDA reaction. According to other embodiments of the present disclosure, the coupling arm has a TCO group, which is capable of being linked to a second element having a tetrazine group via the iEDDA reaction. In the iEDDA reaction, the strained cyclooctenes that possess a remarkably decreased activation energy in contrast to terminal alkynes is employed, and thus eliminate the need of an exogenous catalyst.

Figure 1H:
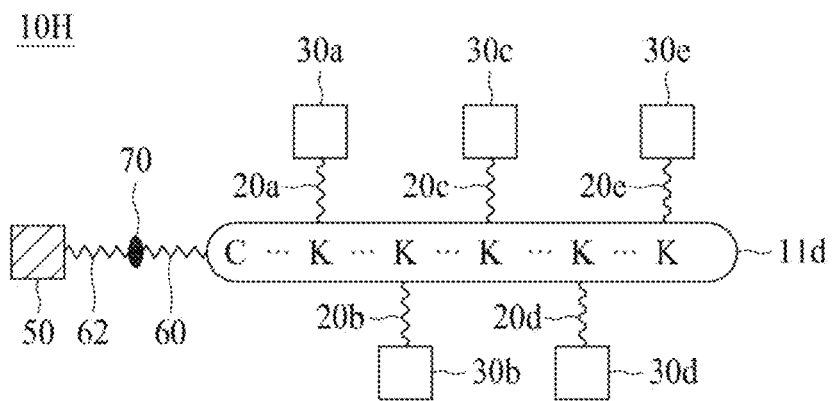

Reference is now made to FIG. 1H, in which the center core 11d of the linker unit 10H comprises a terminal cysteine (C) residue and five lysine (K) residues. As depicted in FIG. 1H, five linking arms 20a-20e are respectively linked to the five K residue of the center core 11d, and then five first elements 30a-30e are respectively linked to the five linking arms 20a-20e via thiol-maleimide reactions. The cysteine residue is linked to the coupling arm 60, which, before being conjugated with the second element, comprises a tetrazine group or a TCO group at its free-terminus. In this example, a second element 50 linked with a short PEG chain 62 having a corresponding TCO or tetrazine group can be linked to the coupling arm 60 via the iEDDA reaction. The ellipse 70 as depicted in FIG. 1H represents the chemical bond resulted from the iEDDA reaction occurred between the coupling arm 60 and the short PEG chain 62.

According to other embodiments of the present disclosure, before the conjugation with a second element, the coupling arm has an azide group. As such, the coupling arm can be linked to the second element having a cyclooctyne group (e.g., the DBCO, DIFO, BCN, or DICO group) at the free-terminus of a short PEG chain via SPAAC reaction, and vice versa.

Figure 1I:
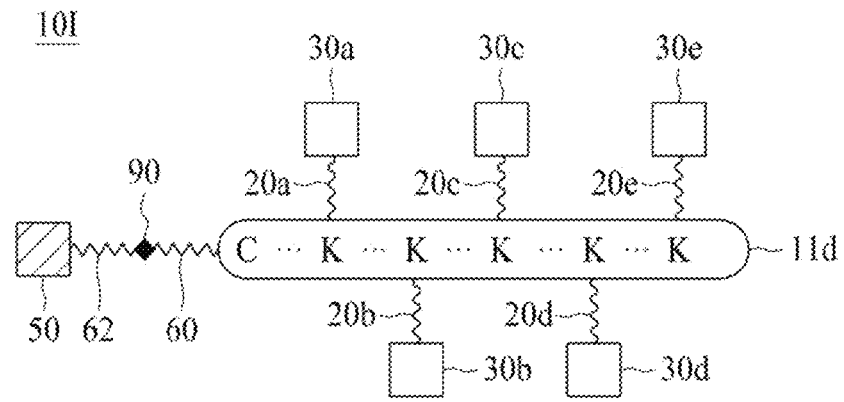

Reference is now made to FIG. 1I, in which the linker unit 10I has a structure similar to the linker unit 10H of FIG. 1H, except that the coupling arm 60 comprises an azide or a cyclooctyne group (e.g., the DBCO, DIFO, BCN, or DICO group), instead of the tetrazine or TCO group. Accordingly, the second element 50 linked with a short PEG chain 62 may have a corresponding cyclooctyne (e.g., DBCO, DIFO, BCN, or DICO) or azide group, so that it can be linked to the coupling arm 60 via the SPAAC reaction. The diamond 90 as depicted in FIG. 1I represents the chemical bond resulted from the SPAAC reaction occurred between the coupling arm 60 and the short PEG chain 62.

Scheme 4 is an exemplary illustration of the process of preparing the present linker unit. In step 1, the center core comprising the amino acid sequence of $(GSK)_3$ and a L-azidohomoalanine (AHA) residue at the C-terminus thereof is prepared. In step 2, three linking arms are respectively linked to the lysine (K) residues of the center core via forming an amide bond between the NHS group and the amine group; the linking arm linked to the center core has a maleimide (Mal) group at the free-terminus thereof. In step 3, three anti-A antigen scFvs (scFv α A) as the first element are respectively linked to the linking arms via the thiol-maleimide reaction. Meanwhile, in step 4, one anti-B antigen scFv (scFv α B) as the second element is linked with a short PEG chain that has 4 repeats of EG units and a DBCO group at the free terminus. Finally, in step 5, the second element is linked to the AHA residue of the center core via the SPAAC reaction.

<<Scheme 4 Preparation of linker unit linked with two different scFvs via linking arm and C-terminal amino acid residue>>

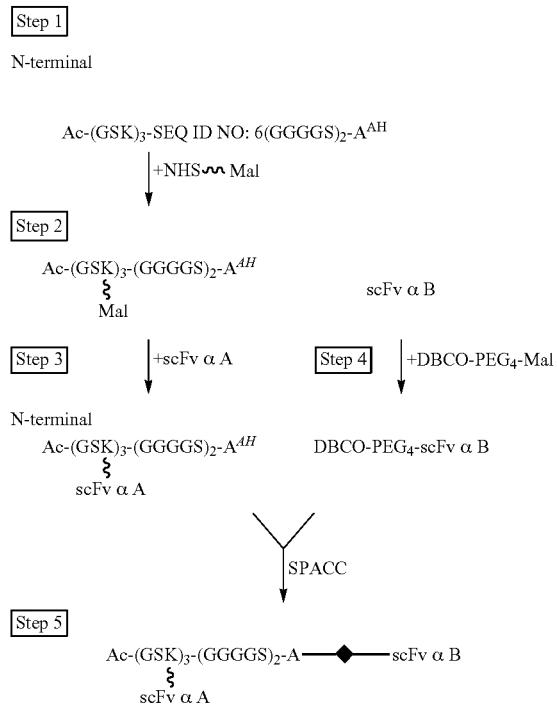

Scheme 5 illustrates another example of the process for preparing the present linker unit. In step 1, the center core comprising the amino acid sequence of $(K-Xaa)_3$ and a cysteine residue at the C-terminus thereof is prepared. In step 2, a PEG chain (as the coupling arm) that has the maleimide (Mal) group at one terminus and a tetrazine group at the other terminus is linked to the cysteine residue via the thiol-maleimide reaction. Then, in step 3, three linking arm are respectively linked to the lysine (K) residues of the center core. Next, three anti-A antigen scFvs (scFv α A) as the first elements are respectively linked to the linking arms via the thiol-maleimide reaction as described in step 4. Meanwhile, in step 5, one anti-B antigen scFv (scFv α B) as the second element is linked with a short PEG chain that has 3 repeats of EG units and a TCO group at the free terminus. Finally, in step 6, the second element is linked to the coupling arm via the iEDDA reaction.

<<Scheme 5 Preparation of linker unit linked with two different scFvs via linking arm and coupling arm>>

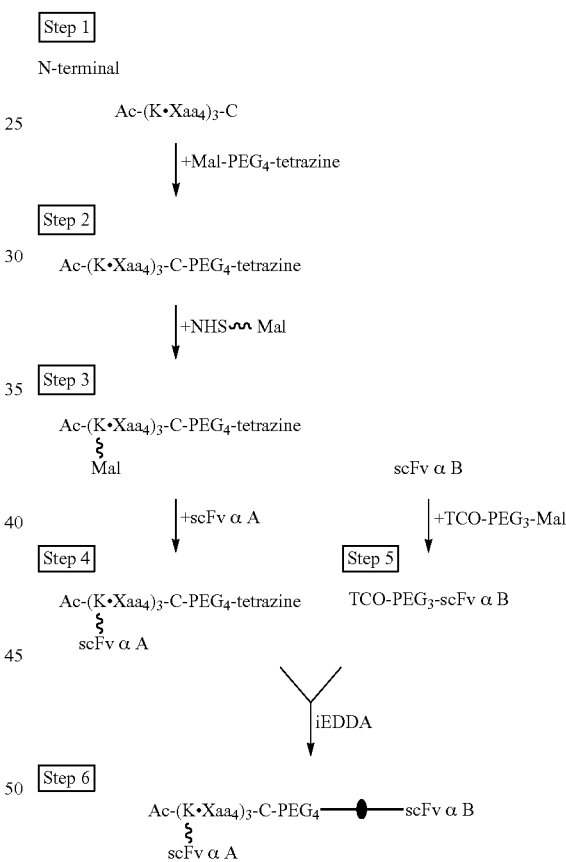

PEGylation is a process, in which a PEG chain is attached or linked to a molecule (e.g., a drug or a protein). It is known that PEGylation imparts several significant pharmacological advantages over the unmodified form, such as improved solubility, increased stability, extended circulating life, and decreased proteolytic degradation. According to one embodiment of the present disclosure, the second element is a PEG chain, which has a molecular weight of about 20,000 to 50,000 daltons.

Figure 1J:
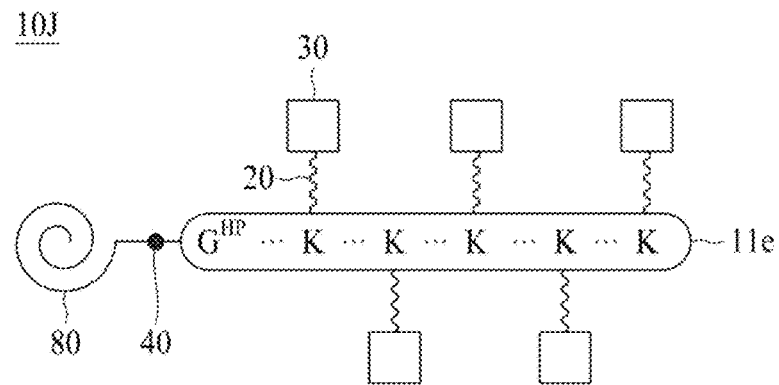

FIG. 1J provides an alternative example of the present linker unit (linker unit 10J), in which five first elements 30 are respectively linked to the lysine residues via the linking arms 20, and the AHA ($A^{AH}$) residue of the center core Ile is linked with a PEG chain 80 via the CuAAC reaction. The solid dot 40 depicted in FIG. 1J represents the chemical bond resulted from the CuAAC reaction occurred between the AHA residue and the PEG chain 80.

Figure 1K:
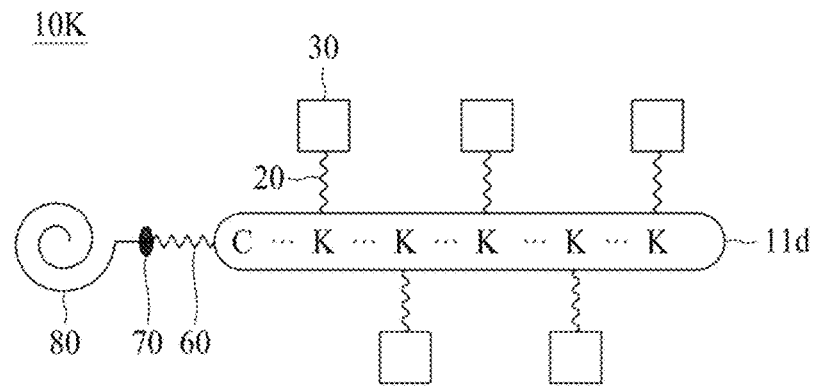

FIG. 1K provides another example of the present disclosure, in which the N-terminus of the center core 11d is a cysteine residue that is linked to a coupling arm 60. A PEG chain 80 can be efficiently linked to the coupling arm 60 via the iEDDA reaction. The ellipse 70 of the linker unit 10K represents the chemical bond resulted from the iEDDA reaction occurred between the coupling arm 60 and the PEG chain 80.

Figure 1L:
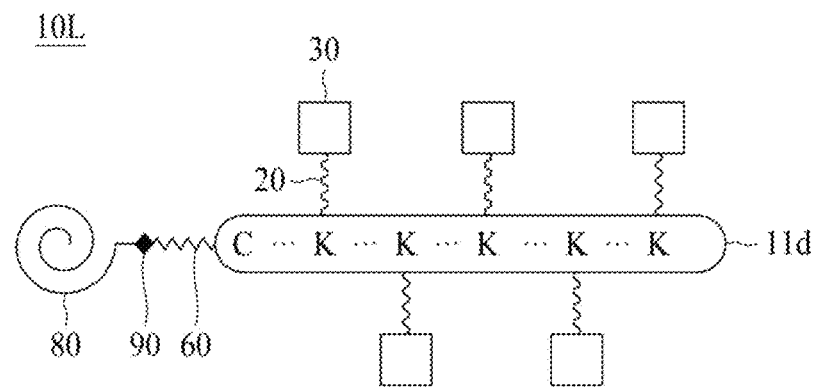

FIG. 1L provides an alternative example of the present linker unit, in which the linker unit 10L has a structure similar to the linker unit 10J of FIG. 1J, except that the PEG chain 80 is linked to the coupling arm 60 via the SPAAC reaction. The diamond 90 depicted in FIG. 1K represents the chemical bond resulted from the SPAAC reaction occurred between the coupling arm 60 and the PEG chain 80.

According to some embodiments of the present disclosure, in addition to the first and second elements, the present linker unit further comprises a third element. In this case, one of the N- and C-terminus of the center core is an amino acid having an azide group or an alkyne group, while the other of the N- and C-terminus of the center core is a cysteine residue. The lysine residues of the center core are respectively linked with the linking arms, each of which has a maleimide group at its free terminus; whereas the cysteine residue of the center core is linked with the coupling arm, which has a tetrazine group or a strained alkyne group at its free terminus. As described above, the first element is therefore linked to the linking arm via the thiol-maleimide reaction, and the second element is linked to the coupling arm via the iEDDA reaction. Further, a third element is linked to the terminal amino acid having an azide group or an alkyne group via the CuAAC reaction or SPAAC reaction.

Figure 1M:
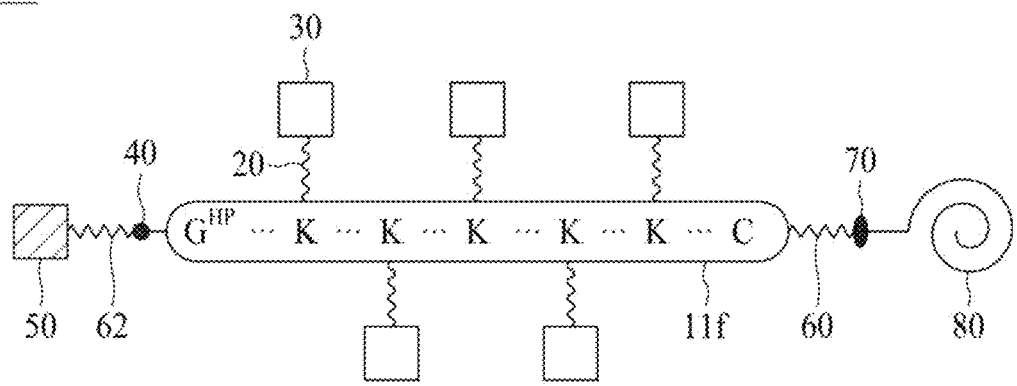

Reference is now made to the linker unit 10M of FIG. 1M, in which the center core 11f has an HPG ($G^{HP}$) residue at the N-terminus thereof and a cysteine residue at the C-terminus thereof. The linking arms 20 and the coupling arm 60 are respectively linked to the lysine (K) residues and the cysteine (C) residue of the center core 11f. Further, five first elements 30 are respectively linked to the five linking arms 20, the second element (i.e., the PEG chain) 80 is linked to the coupling arm 60 via the short PEG chain 62, and the third element 50 is linked to the HPG residue. The solid dot 40 indicated the chemical bond resulted from the CuAAC reaction occurred between the HPG residue and the short PEG chain 62; while the ellipse 70 represents the chemical bond resulted from the iEDDA reaction occurred between the coupling arm 60 and the PEG chain 80.

Figure 1N:
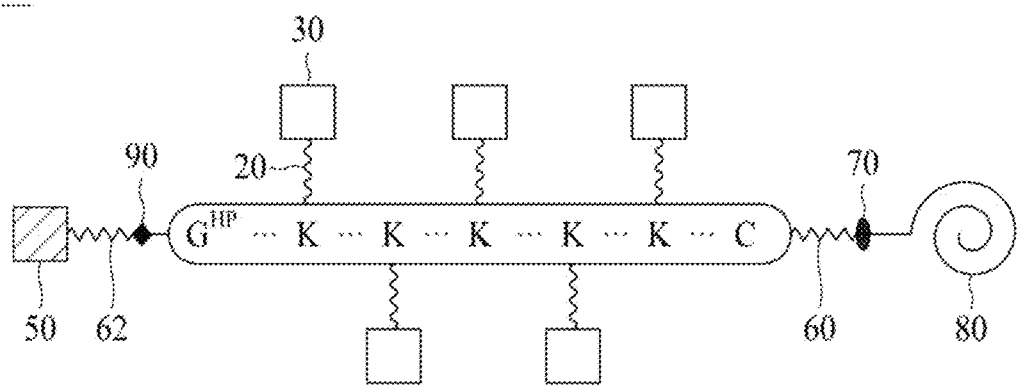

FIG. 1N provides another embodiment of the present disclosure, in which the linker unit 10N has the similar structure with the linker unit 10M of FIG. 1M, except that the short PEG chain 62 is linked with the HPG residue via the SPAAC reaction, instead of the iEDDA reaction. The diamond 90 in FIG. 1N represents the chemical bond resulted from the SPAAC reaction occurred between the short PEG chain 62 and the HPG residue.

In the preferred embodiments of this disclosure, the linking arms have a maleimide group in the free terminus for conjugating with first elements having the sulfhydryl group via the thiol-maleimide reaction. Also, there is one cysteine residue or an amino acid residue with an azide or alkyne group at a terminus of the peptide core for attaching a coupling arm for linking a second element.

It is conceivable for those skilled in the arts that variations may be made. A conjugating group, other than maleimide, such as azide, alkyne, tetrazine, or strained alkyne may be used for the free terminus of the linking arms, for linking with first elements with a CuAAC, iEDDA, or SPAAC reaction. Also the cysteine residue (or an amino acid residue with an azide or alkyne group) of the peptide core needs not to be at the N- or C-terminus. Furthermore, two or more of such residues may be incorporated in the peptide core to attach multiple coupling arms for linking a plural of second elements.

I-(ii) Compound Core for Use in Multi-Arm Linker

In addition to the linker unit described in part I-(i) of the present disclosure, also disclosed herein is another linker unit that employs a compound, instead of the polypeptide, as the center core. Specifically, the compound is benzene-1,3,5-triamine, 2-(aminomethyl)-2-methylpropane-1,3-diamine, tris(2-aminoethyl)amine, benzene-1,2,4,5-tetraamine, 3,3",5,5'-tetraamine-1,1-biphenyl, tetrakis(2-aminoethyl)methane, tetrakis-(ethylamine)hydrazine, N,N,N',N",-tetrakis (aminoethyl)ethylenediamine, benzene-1,2,3,4,5,6-hexaamine, 1-N,1-N,3-N,3-N,5-N,5-N-hexakis (methylamine)-benzene-1,3,5-triamine, 1-N,1-N,2-N,2-N,4-N,4-N,5-N,5-N,-octakis(methylamine)-benzene-1,2,4,5-triamine, benzene-1,2,3,4,5,6-hexaamine, or N,N-bis[(1-amino-3,3-diaminoethyl)pentyl]-methanediamine. Each of these compounds has 3 or more amine groups in identical or symmetrical configuration. Therefore, when one of the amine groups of a compound is conjugated with a coupling arm, all of the molecules of the compound have the same configuration.

Similar to the mechanism of linkage described in Part I-(i) of the present disclosure, each compound listed above comprises a plurality of amine groups, and thus, a plurality of PEG chains having NHS groups can be linked to the compound via forming an amine linkage between the amine group and the NHS group; the thus-linked PEG chain is designated as linking arm, which has a functional group (e.g., an NHS, a maleimide, an azide, an alkyne, a tetrazine, a cyclooctene, or a cyclooctynep group) at the free-terminus thereof. Meanwhile, at least one of the amine groups of the compound core is linked to another PEG chain, which has an NHS group at one end, and a functional group (e.g., an azide, alkyne, tetrazine, a cyclooctene, or a cyclooctynep group) at the other end; the thus-linked PEG chain is designated as coupling arm, which has a functional group at the free-terminus thereof.

Accordingly, a first element can be linked to the linking arm via (1) forming an amide bond therebetween, (2) the thiol-maleimide reaction, (3) the CuAAC reaction, (4) the iEDDA reaction, or (5) SPAAC reaction. Meanwhile, the second element can be linked to the coupling arm via the CuAAC, iEDDA or SPAAC reaction. t.

According to some embodiments of the present disclosure, the linking arm is a PEG chain having 2-20 repeats of EG units; preferably, the linking arm is a PEG chain having 2-20 repeats of EG units with a disulfide linkage at the free terminus thereof (i.e., the terminus that is not with the center core). The coupling arm is a PEG chain having 2-12 repeats of EG unit. In one embodiment, both the linking and coupling arms have 12 repeats of EG unit, in which one terminus of the coupling arm is an NHS group, and the other terminus of the coupling arm is an alkyne group.

According to an alternative embodiment of the present disclosure, the linker unit further comprises a plurality of connecting arms, each of which is linked to each of the linking arm. Then, a plurality of the first elements are respectively linked to the plurality of connecting arms. In one embodiment, the connecting arm is a PEG chain having 2-20 repeats of EG units. In another embodiment, the connecting arm is a PEG chain having 2-20 repeats of EG units with a disulfide linkage at the element-linking terminus that is not linked with the linking arm.

Schemes 6 and 7 respectively depict the linkages between the center compound core and the linking arm, as well as the coupling arm. In schemes 6 and 7, "NHS" represents the NHS ester, "Mal" represents the maleimide group, "azide" represents the azide group, and "alkyne" represents the alkyne group.

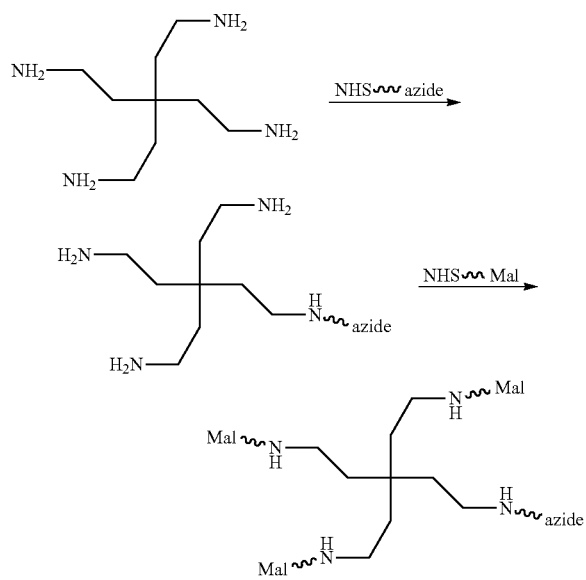

<<Scheme 6 Linkage of linking and coupling arms respectively having maleimide group and azide group to center core>>

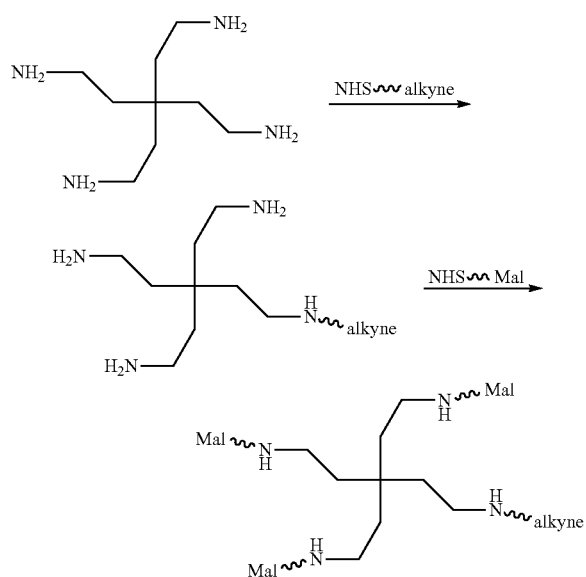

<<Scheme 7 Linkage of linking and coupling arms respectively having maleimide group and alkyne group to center core>>

The requirement of having multiple $NH_2$ groups exist in a symmetrical and identical orientation in the compound serving as the center core is for the following reason: when one of the $NH_2$ group is used for connecting a bifunctional linker arm with N-hydroxysuccinimidyl (NHS) ester group and alkyne, azide, tetrazine, or strained alkyne group, the product, namely, a core with a coupling arm having alkyne, azide, tetrazine or strained alkyne, is homogeneous and may be purified. Such a product can then be used to produce multi-arm linker units with all other $NH_2$ groups connected to linking arms with maleimide or other coupling groups at the other ends. If a compound with multiple $NH_2$ groups in non-symmetrical orientations, the product with one bifunctional linking arm/coupling arms is not homogeneous.

Some of those symmetrical compounds can further be modified to provide center cores with more linking arms/coupling arms. For example, tetrakis(2-aminoethyl)methane, which can be synthesized from common compounds or obtained commercially, may be used as a core for constructing linker units with four linking arms/coupling arms. Tetrakis(2-aminoethyl)methane can react with bis(sulfosuccinimidyl)suberate to yield a condensed product of two tetrakis(2-aminoethyl)methane molecules, which can be used as a core for constructing linker units having six linking arms/coupling arms. The linker units, respectively having 3 linking arms/coupling arms, 4 linking arms/coupling arms and 6 linking arms/coupling arms, can fulfill most of the need for constructing targeting/effector molecules with joint-linker configuration.

As would be appreciated, the numbers of the linking arm and/or the coupling arm and the element linked thereto may vary with the number of amine groups comprised in the center core. In some preferred embodiments, the numbers of the linking arm/coupling arm and the corresponding linking element linked thereto ranges from about 1-7.

Figure 2:
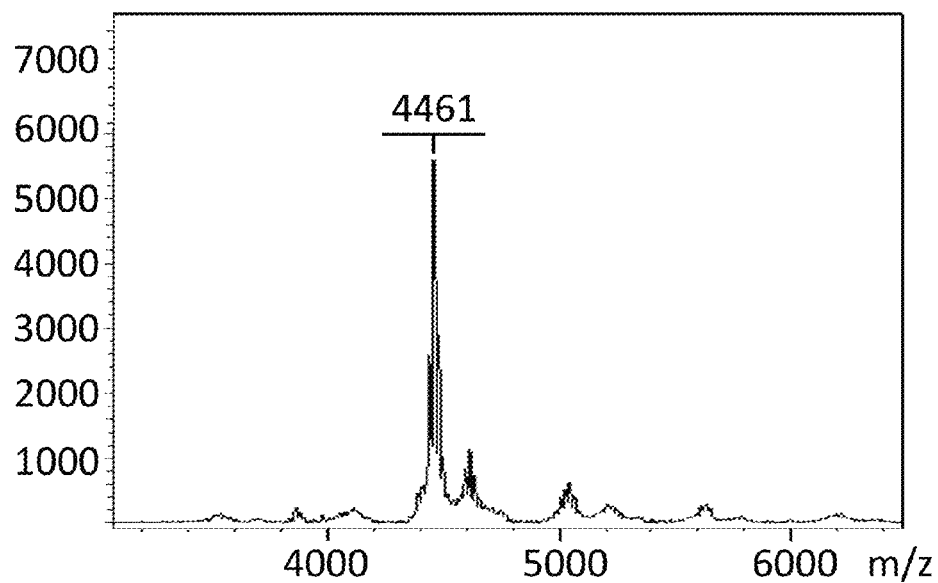
FIG. 2 shows the mass spectrometry MALDI-TOF result of a peptide core-based linker-unit carrying one linking arm with tetrazine group and three PEG linking arms with maleimide groups.

Reference is now made to FIG. 2, in which benzene-1,2,4,5-tetraamine having 4 amine groups is depicted. Three of the amine groups are respectively linked to the linking arms 20, and one of the amine group is linked to the coupling arm 60, which has an azide group at its free-terminus. Three first elements 30 are then respectively linked to the three linking arms 20 via the thiol-maleimide reactions, and one second element 50 is linked to the coupling arm 60 via the CuAAC reaction. The solid dot 40 as depicted in FIG. 2 represents the chemical bond resulted from the CuAAC reaction occurred between the coupling arm 60 and the second element 50.

I-(iii) Functional Elements Suitable for Use in Multi-Arm Linker

In the case where the linker unit (or multi-arm linker) comprises only the first element but not the second and/or third element(s), the first element is an effector element that may elicit a therapeutic effect in a subject. On the other hand, when the present linker unit comprises elements in addition to first element(s), then at least one of the elements is an effector element, while the other may be another effector element, a targeting element, or an element capable of enhancing one or more pharmacokinetic properties of the linker unit (e.g., solubility, clearance, half-life, and bioavailability). For example, the linker unit may have two different kinds of effector element, one effector element and one targeting element or one pharmacokinetic property-enhancing element, two different kinds of targeting elements and one kind of effector element, two different kinds of effector elements and one kind of targeting element, or one kind of targeting element, one kind of effector element and one element capable of improving the pharmacokinetic property of the linker unit.

According to certain embodiments of the present disclosure, the targeting element or the effector element is fingolimod, fingolimod phosphate, interferon-β, or a single-chain variable fragment (scFv) specific for integrin-α4, β-amyloid, a viral protein, or a bacterial protein.

Examples of viral proteins include, but are not limited to, F protein of respiratory syncytia virus (RSV), gp120 protein of human immunodeficiency virus type 1 (HIV-1), hemagglutinin A (HA) protein of influenza A virus, and glycoprotein of cytomegalovirus.

Illustrative examples of bacterial protein include endotoxin of Gram(−) bacteria, surface antigen of *Clostridium difficile*, lipoteichoic acid of Saphylococcus *aureus*, anthrax toxin of *Bacillus anthracis*, and Shiga-like toxin type I or II of *Escherichia coli*.

Elements that enhance one or more pharmacokinetic properties of the linker unit can be a long PEG chain having a molecular weight of about 20,000 to 50,000 daltons.

Specific examples of the functional elements incorporated in the present multi-arm linker for treating a particular disease are discussed below.

To treat a CNS disease, such as multiple sclerosis, one exemplary linker unit may use fingolimod, fingolimod phosphate, interferon-β, or an scFv specific for integrin-α4 as the first element (effector element). To treat Alzheimer's disease, the present linker unit may use an scFv specific for β-amyloid as the first element (effector element). Optionally, the linker unit for treating multiple sclerosis, Alzheimer's disease, or other CNS diseases may further comprise a second element of an scFv specific for transferrin receptor as the targeting element.

Similarly, an scFv specific for a viral or bacterial protein can be used as the targeting element (first element) in order to treat the infection caused by the virus or bacterium. In these cases, the linker unit may comprise an optional second element, such as an scFv specific for CD32 or CD16b, as the effector element.

I-(iv) Use of Multi-Arm Linker

The present disclosure also pertains to method for treating various diseases using the suitable linker unit. Generally, the method comprises the step of administering to a subject in need of such treatment an effective amount of the linker unit according to embodiments of the present disclosure.

Compared with previously known therapeutic constructs, the present linker unit discussed in Part I is advantageous in two points:

(1) The number of the functional elements may be adjusted in accordance with the needs and/or applications. The present linker unit may comprise two elements (i.e., the first and second elements) or three elements (i.e., the first, second, and third elements) in accordance with the requirements of the application (e.g., the disease being treated, the route of administration of the present linker unit, and the binding avidity and/or affinity of the antibody carried by the present linker unit). For example, when the present linker unit is directly delivered into the tissue/organ (e.g., the treatment of eye), one element acting as the effector element may be enough, thus would eliminate the need of a second element acting as the targeting element. However, when the present linker unit is delivered peripherally (e.g., oral, enteral, nasal, topical, transmucosal, intramuscular, intravenous, or intraperitoneal injection), it may be necessary for the present linker unit to simultaneously comprise a targeting element that specifically targets the present linker unit to the lesion site; and an effector element that exhibits a therapeutic effect on the lesion site. For the purpose of increasing the targeting or treatment efficacy or increasing the stability of the present linker unit, a third element (e.g., a second targeting element, a second effector element, or a PEG chain) may be further included in the present linker unit.

(2) The first element is provided in the form of a bundle. As described above, the number of the first element may vary with the number of lysine residue comprised in the center core. If the number of lysine residue in the center core ranges from 2 to 15, then at least two first elements may be comprised in each linker unit. Thus, instead of providing one single molecule (e.g., cytotoxic drug and antibody) as traditional therapeutic construct or method may render, the present linker unit is capable of providing more functional elements (either as targeting elements or as effector elements) at one time, thereby greatly improves the therapeutic effect.

In certain therapeutic applications, it is desirable to have a single copy of a targeting or effector element. For example, a single copy of a targeting element can be used to avoid unwanted effects due to overly tight binding. This consideration is relevant, when the scFv has a relatively high affinity for the targeted antigen and when the targeted antigen is a cell surface antigen on normal cells, which are not targeted diseased cells. As an example, in using scFv specific for CD3 or CD16a to recruit T cells or NK cells to kill targeted cells, such as thyroid gland cells in patients with Graves' disease, a single copy of the scFv specific for CD3 or CD16a is desirable, so that unwanted effects due to cross-linking of the CD3 or CD16a may be avoided. Similarly, in using scFv specific for CD32 or CD16b to recruit phagocytic neutrophils and macrophages to clear antibody-bound viral or bacterial particles or their products, a single copy of scFv may be desirable. Also, in using scFv specific for transferrin receptor to carry effector drug molecules to the BBB for treating CNS diseases, a single copy of scFv specific for transferrin receptor is desirable. In still another example, it is desirable to have only one copy of long-chain PEG for enhancing pharmacokinetic properties. Two or more long PEG chains may cause tangling and affect the binding properties of the targeting or effector elements.

EXPERIMENTAL EXAMPLES

Example 1: Synthesis of Peptide 1 (SEQ ID NO: 18), Peptide 2 (SEQ ID NO: 27) and Peptide 3 (SEQ ID NO: 19) as Peptide Cores, and Conjugation of the SH Group of their Cysteine Residue with Maleimide-PEG$_3$-Transcyclooctene (TCO) as a Coupling Arm The synthesized peptides 1, 2 and 3 (Chinapeptide Inc., Shanghai, China) were processed similarly. Each peptide was dissolved in 100 mM sodium phosphate buffer (pH 7.0) containing 50 mM NaCl and 5 mM EDTA at a final concentration of 2 mM. The dissolved peptide was reduced by 1 mM tris(2-carboxyethyl)phosphine (TCEP) at 25° C. for 2 hours. For conjugating the SH group of the cysteine residue with maleimide-PEG$_3$-TCO (Conju-probe Inc.) to create a functional linking group TCO, the peptide and maleimide-PEG$_3$-TCO were mixed at a 1/7.5 molar ratio and incubated at pH 7 and 25° C. for 18 hours. The TCO-conjugated peptide was purified by reverse phase HPLC on a Supelco C18 column (250 mm×10 mm; 5 μm), using a mobile phase of acetonitrile and 0.1% trifluoroacetic acid, a linear gradient of 0% to 100% acetonitrile over 30 minutes, at a flow rate of 1.0 mL/min and a column temperature of 25° C.

The identification of the synthesized TCO-peptides (illustrated below) was carried out by MALDI-TOF mass spectrometry. Mass spectrometry analyses were performed by the Mass Core Facility at the Institute of Molecular Biology (IMB), Academia Sinica, Taipei, Taiwan. Measurements were performed on a Bruker Autoflex III MALDI-TOF/TOF mass spectrometer (Bruker Daltonics, Bremen, Germany).

The synthesized TCO-peptide 1, as illustrated below, had a molecular weight (m.w.) of 2,078.9 daltons.

(SEQ ID NO: 18)

TCO—PEG$_3$-CGGSGGSGGSKGSGSKGSK

The synthesized TCO-peptide 2, as illustrated below, had a m.w. of 2,020.09 daltons.

(SEQ ID NO: 27)

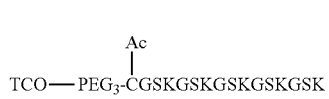

TCO—PEG$_3$-CGSKGSKGSKGSKGSK

The TCO-peptide 3, as illustrated below, had a m.w. of 3,381.85 daltons.

(SEQ ID NO: 19)

TCO—PEG$_3$-CGSKGSKGSKGSKGSKGSKGSKGSKGSKGSK

Example 2: Synthesis of Peptide 1 as a Peptide Core, and Conjugation of the SH Group of its Cysteine Residue with Maleimide-PEG$_4$-Tetrazine as a Coupling Arm The synthesized peptide 1 (Chinapeptide Inc., Shanghai, China) was dissolved in 100 mM sodium phosphate buffer (pH 7.0) containing 50 mM NaCl and 5 mM EDTA at a final concentration of 2 mM. The dissolved peptide was reduced by 1 mM tris(2-carboxyethyl)phosphine (TCEP) at 25° C. for 2 hours. For conjugating the SH group of the cysteine residue with maleimide-PEG$_4$-tetrazine (Conju-probe Inc., San Diego, USA) to create a functional linking group tetrazine, the peptide and maleimide-PEG$_4$-tetrazine were mixed at a 1/5 ratio and incubated at pH 7 and 4° C. for 18 hours. The tetrazine-conjugated peptide was purified by reverse phase HPLC on a Supelco C18 column (250 mm×10 mm; 5 μm), using a mobile phase of acetonitrile and 0.1% trifluoroacetic acid, a linear gradient of 0% to 100% acetonitrile over 30 minutes, at a flow rate of 1.0 mL/min and a column temperature of 25° C.

The synthesized tetrazine-peptide 1, as illustrated below, had a m.w. of 2,185.2 daltons.

(SEQ ID NO: 18)

Tetrazine—PEG$_4$-CGGSGGSGGSKGSGSKGSK

Example 3: Synthesis of a Linker Unit by Conjugating NHS-PEG$_{12}$-Mal to NH$_2$ Groups of TCO-Peptide 1 as Linking Arms Three linking arms of PEG$_{12}$-maleimide were attached to the peptide core, TCO-peptide 1. The crosslinker, NHS-PEG$_{12}$-maleimide (succinimidyl-[(N-maleimido-propionamido)-dodecaethyleneglycol] ester, was purchased from Thermo Fisher Scientific Inc. (Waltham, USA). The conjugation procedure was performed per the manufacturer's instruction. Briefly, the peptide with lysine residues was dissolved in the conjugation buffer, phosphate buffered saline (pH 7.5) at 100 mM. NHS-PEG$_{12}$-maleimide crosslinker was then added to the dissolved peptide at a 1 mM final concentration (10-fold molar excess over 0.1 mM peptide solution). The reaction mixtures were incubated for 18 hours at room temperature. The maleimide-PEG$_{12}$-conjugated TCO-peptide 1 was purified by reverse phase HPLC on a Supelco C18 column (250 mm×4.6 mm; 5 μm), using a mobile phase of acetonitrile and 0.1% trifluoroacetic acid, a linear gradient of 0% to 100% acetonitrile over 30 minutes, at a flow rate of 1.0 mL/min and a column temperature of 25° C.

The identification of the maleimide-PEG$_{12}$-conjugated TCO-peptide 1 was carried out by mass spectrometry MALDI-TOF.

The synthesized maleimide-PEG$_{12}$-conjugated TCO-peptide1 had a m.w. of 4,332 daltons. As illustrated below, the maleimide-PEG$_{12}$-conjugated TCO-peptide1 is a peptide-core based linker unit carrying one TCO group and three PEG linking arms with maleimide groups.

(SEQ ID NO: 18)

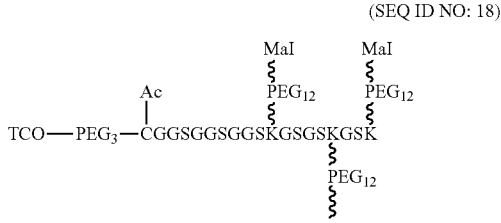

Example 4: Synthesis of a Linker Unit by Conjugating NHS-PEG$_{12}$-Mal to NH$_2$ Groups of Tetrazine-Peptide 1 as Linking Arms Three linking arms of PEG$_{12}$-maleimide were attached to the peptide core, tetrazine-peptide 1. The crosslinker, NHS-PEG$_{12}$-maleimide (succinimidyl-[(N-maleimido-propionamido)-dodecaethyleneglycol] ester, was purchased from Thermo Fisher Scientific Inc. (Waltham, USA). The conjugation procedure was performed per the manufacturer's instruction. Briefly, the peptide with lysine residues was dissolved in the conjugation buffer, phosphate buffered saline (pH 7.5) at 100 mM. NHS-PEG$_{12}$-maleimide cross-linker was then added to the dissolved peptide at a 1 mM final concentration (10-fold molar excess over 0.1 mM peptide solution). The reaction mixtures were incubated for 18 hours at room temperature. The maleimide-PEG$_{12}$-conjugated tetrazine-peptide 1 was purified by reverse phase HPLC on a Supelco C18 column (250 mm×4.6 mm; 5 μm), using a mobile phase of acetonitrile and 0.1% trifluoroacetic acid, a linear gradient of 0% to 100% acetonitrile over 30 minutes, at a flow rate of 1.0 mL/min and a column temperature of 25° C.

(SEQ ID NO: 18)

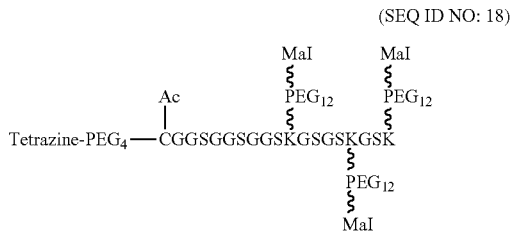

The synthesized maleimide-PEG$_{12}$-conjugated tetrazine-peptide1, as illustrated herein, was a peptide-core based linker unit carrying one tetrazine group and three PEG linking arms with maleimide groups. FIG. 2 shows the MALDI-TOF result, indicating that the construct had a m.w. of 4,461 daltons.

Example 5: Conjugation of Fingolimod and Fingolimod Phosphate Molecule with an NHS-PEG$_5$-NHS Cross-Linker Fingolimod was purchased from Biotang Inc. (Lexington, USA) and fingolimod phosphate from KM3 Scientific Corporation (New Taipei City, Taiwan). The NH$_2$ group of fingolimod molecule was reacted with a homo-bifunctional crosslinker, NHS-PEG$_5$-NHS, as shown in scheme 8. Fingolimod was dissolved in 100% DMSO at a final concentration of 10 mM; NHS-PEG$_5$-NHS was dissolved in 100% DMSO at a 250 mM final concentration. To activate the NH$_2$ group of fingolimod, 6% (v/v) of basic sodium phosphate buffer (pH12.7) was added to the fingolimod solution and then incubated for 10 minutes. NHS-PEG$_5$-NHS crosslinker was added to the dissolved fingolimod solution at a final concentration of 30 mM (3-fold molar excess over 10 mM fingolimod solution). The reaction mixture was incubated for 3 hours at room temperature.

Fingolimod phosphate was dissolved in 100% DMSO at a final concentration of 5 mM, and NHS-PEG$_5$-NHS cross-linker was dissolved in 100% DMSO at a final concentration of 250 mM. NHS-PEG$_5$-NHS crosslinker was added to the dissolved fingolimod phosphate solution at a 15 mM final concentration (3-fold molar excess over 5 mM fingolimod phosphate solution). The reaction mixture was incubated for 3 hours at room temperature, then 18% (v/v) acid sodium phosphate buffer (pH=0.88) was added to quench the reaction. The solvent was evaporated under vacuum.

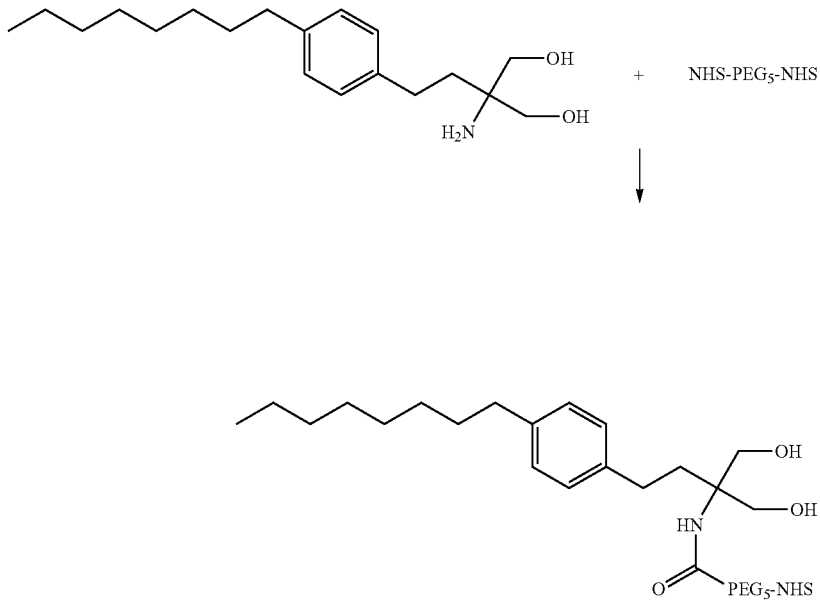

<<Scheme 8 Conjugation of fingolimod molecule with an NHS-PEG$_5$-NHS cross-linker>>

NHS-PEG$_5$-conjugated fingolimod and NHS-PEG$_5$-conjugated fingolimod phosphate were dissolved in 30% acetonitrile, and then purified using reverse phase HPLC on a Supelco C18 column (250 mm×4.6 mm; 5 μm), using a mobile phase of acetonitrile and 0.1% trifluoroacetic acid, a linear gradient of 30% to 100% acetonitrile over 30 minutes, at a flow rate of 1.0 mL/min and a column temperature of 25° C.

Figure 3:
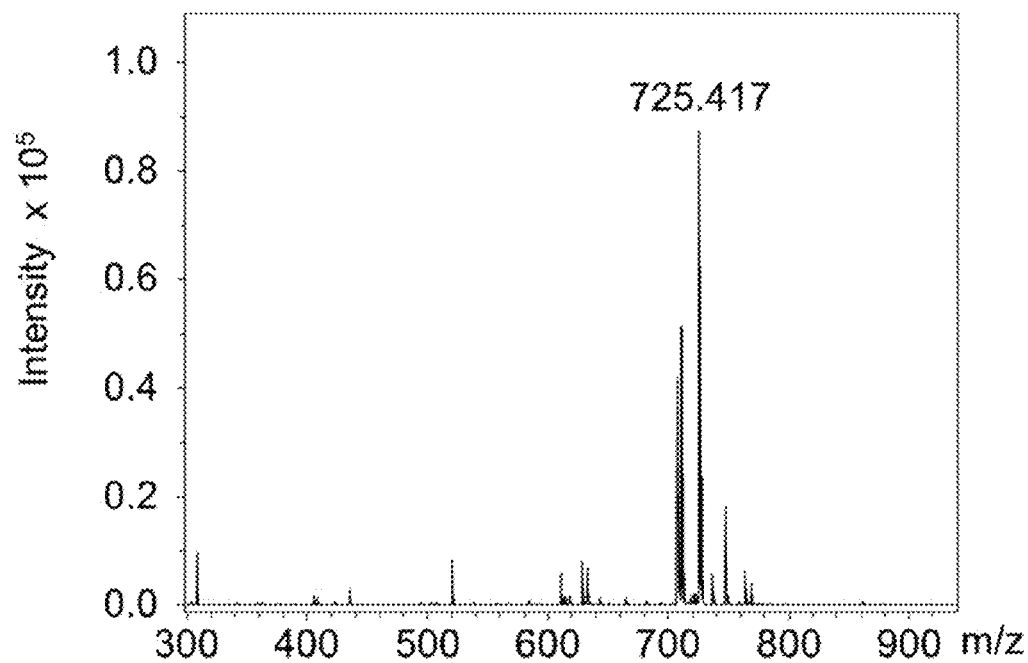
FIG. 3 shows the mass spectrometry MALDI-TOF result of NHS-PEG$_5$-conjugated fingolimod.

FIG. 3 shows that the synthesized NHS-PEG$_5$-conjugated fingolimod, as illustrated in scheme 8, had a m.w. of 725.41 daltons.

DMSO at a final concentration of 250 mM. 5 μl of NHS-PEG$_4$-DBCO crosslinker was added to 400 μl of the dissolved azido-PEG$_3$-S—S-conjugated fingolimod solution to a final molar ratio of 1/3.2 (NHS-PEG$_4$-DBCO: azido-PEG$_3$-S—S-conjugated fingolimod) in 100 mM sodium phosphate buffer at pH 7.5. The reaction mixture was incubated for 3 hours at room temperature.

The synthesized NHS-PEG$_4$-PEG$_3$-S—S-conjugated fingolimod, as illustrated below, had a m.w. of 1,278.61 daltons. The two isotopic peaks were also visible in the MS spectrum at 1,279.64 and 1,280.635, corresponding to [M+H+1] and [M+H+2].

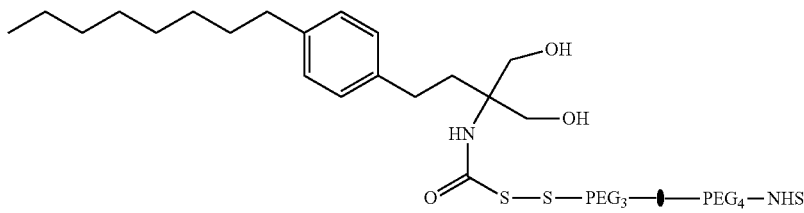

The synthesized NHS-PEG$_5$-conjugated fingolimod phosphate, as illustrated below, had a m.w. of 803.3 daltons.

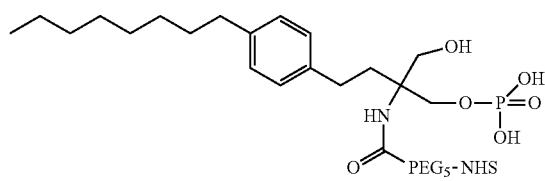

Example 6: Conjugation of Fingolimod Molecule with an NHS—S—S—PEG$_3$-Azido Linking Arm The NH$_2$ group of fingolimod molecule was reacted with a hetero-bifunctional cleavable linker, NHS—S—S—PEG$_3$-azido (Conju-probe Inc.), at a 1:3 molar ratio. The product, azido-PEG$_3$-S—S-fingolimod was purified by HPLC to remove the excess, unreacted fingolimod molecules. The procedures for conjugation and purification were similar to those described in the preceding example.

The synthesized azido-PEG$_3$-S—S-conjugated fingolimod, as illustrated below, had a m.w. of 629.33 daltons.

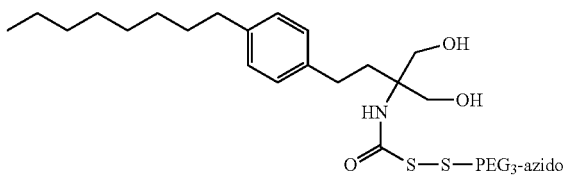

Example 7: Conjugation of Azido-PEG3-S—S-Conjugated Fingolimod Molecule with a NHS-PEG4-Dibenzylcyclooctyne (DBCO) Crosslinker Azido-PEG$_3$-S—S-conjugated fingolimod molecule was dissolved in 100% DMSO at a final concentration of 10 mM, and NHS-PEG$_4$-DBCO crosslinker was dissolved in 100%

Example 8: Conjugation of NHS-PEG$_5$-Conjugated Fingolimod Molecules to TCO-Peptide 2 and 3

Figure 4:
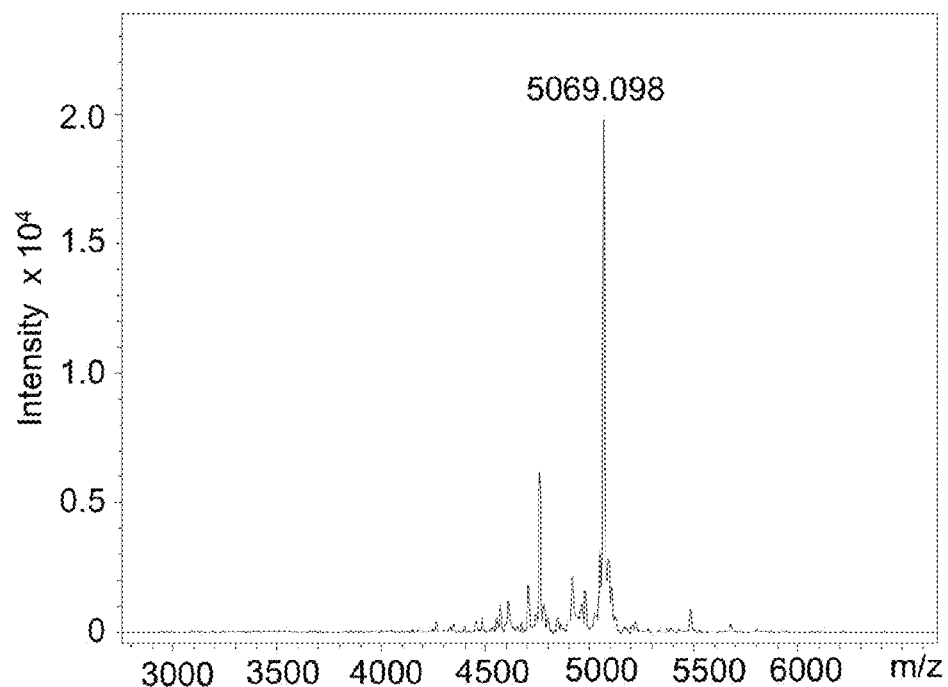
FIG. 4 shows the mass spectrometry MALDI-TOF result of a drug bundle composing of a linker unit with a free TCO functional group and a set of 5 fingolimod molecules.

TCO-peptide 2 was dissolved in 100 mM sodium phosphate buffer at pH 7.5 to a concentration of 20 mM, and NHS-PEG$_5$-conjugated fingolimod was dissolved in 100% DMSO to a concentration of 50 mM. TCO-peptide 2 and NHS-PEG$_5$-conjugated fingolimod were mixed at 1/42 molar ratio in 100% DMSO and incubated for 3 hours at room temperature. Subsequently, additional TCO-peptide 2 was added to the reaction solution to a final molar ratio of 1/13.5 (TCO-peptide 2: NHS PEG$_5$-conjugated fingolimod) in 100% DMSO. The mixture was further incubated for 3 hours at room temperature. FIG. 4 shows that the drug bundle of TCO-peptide 2 with fingolimod had a m.w. of 5,069 daltons.

Figure 5:
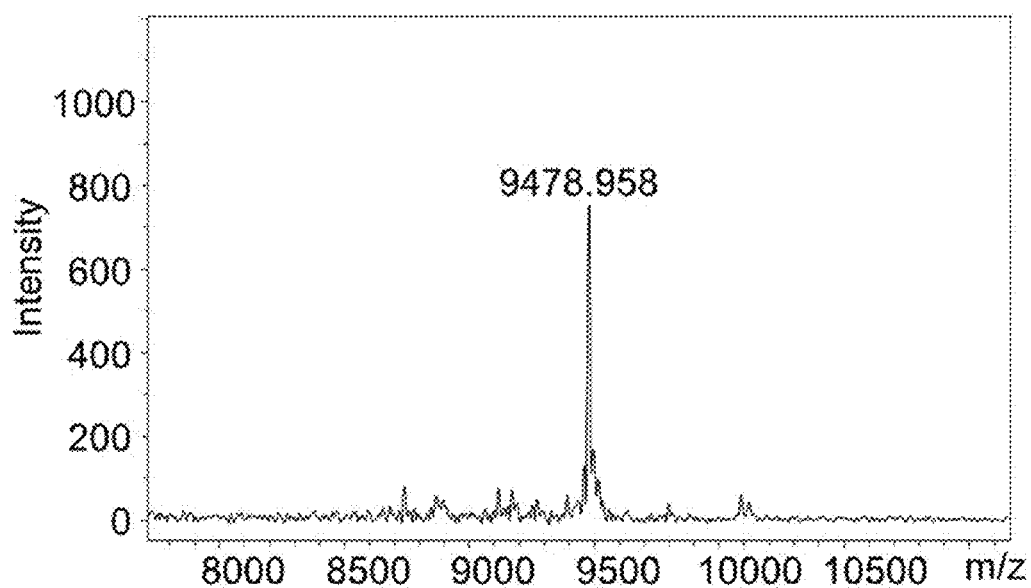
FIG. 5 shows the mass spectrometry MALDI-TOF result of a drug bundle composing of a linker unit with a free TOO functional group and a set of 10 fingolimod molecules.

TCO-peptide 3 was dissolved in 100 mM sodium phosphate buffer at pH 7.5 to a concentration of 10 mM, and NHS-PEG$_5$-conjugated fingolimod was dissolved in 100% DMSO to a concentration of 50 mM. TCO-peptide 3 and PEG$_5$-NHS-conjugated fingolimod were mixed at 1/42 molar ratio at room temperature for overnight. FIG. 5 shows that the drug bundle of TCO-peptide 3 with fingolimod had a m.w. of 9,479 daltons, indicating that ten fingolimod molecules were conjugated to the TCO-peptide 3 linker unit.

The synthesized drug bundle, as illustrated below, was composed of a linker unit with a free TCO functional group and a set of five fingolimod molecules.

(SEQ ID NO: 27)

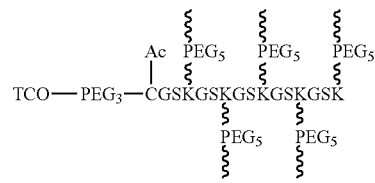

The second synthesized drug bundle, as illustrated below, was composed of a linker unit with a free TCO functional group and a set of ten fingolimod molecules.

(SEQ ID NO: 19)

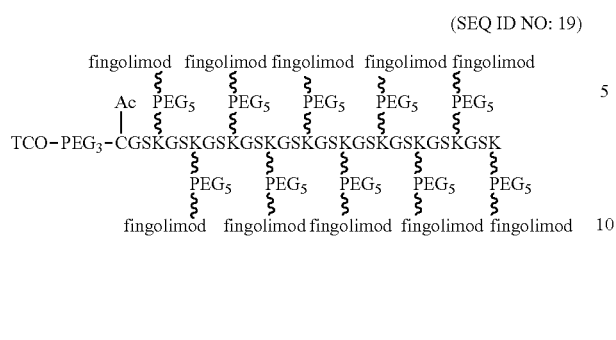

Example 9: Conjugation of NHS-PEG₅-Conjugated Fingolimod Phosphate Molecules to TCO-Peptide 2

Figure 6:
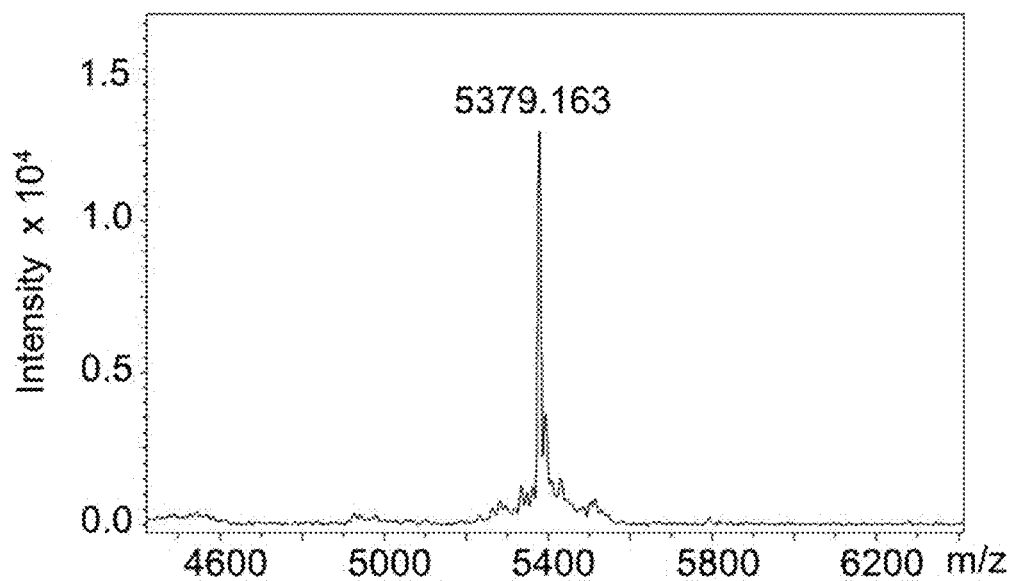
FIG. 6 shows the mass spectrometry MALDI-TOF result of a drug bundle composing of a linker unit with a free TCO functional group and a set of five fingolimod phosphate molecules.

TCO-peptide 2 and NHS-PEG₅-conjugated fingolimod phosphate were mixed at 1/42 molar ratio in 100 mM sodium phosphate buffer at pH 7.5 at room temperature for 3 hours. Mass spectrometric analysis shows that the drug bundle of TCO-peptide 2 with fingolimod phosphate had a m.w. of 5,379.16 daltons (FIG. 6).

(SEQ ID NO: 27)

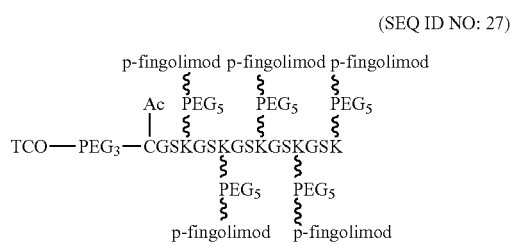

The synthesized drug bundle, as illustrated herein, was composed of a linker unit with a free TCO functional group and a set of five fingolimod phosphate molecules as effector elements.

Example 10: Conjugation of NHS-PEG₄-PEG₃-S—S-Conjugated Fingolimod Molecules to TCO-Peptide2

Five NHS-PEG₄-PEG₃-S—S-conjugated fingolimod molecules were attached to TCO-peptide 2. The conjugation of NHS-PEG₄-PEG₃-S—S-conjugated fingolimod molecules to the NH₂ groups of lysine residues of the TCO-peptide 2 was performed similarly as in the preceding example. The identification was carried out by mass spectrometry MALDI-TOF.

The synthesized drug bundle, as illustrated below, had a m.w. of 7,815 daltons; it was composed of a linker unit with a free TCO functional group and a set of five fingolimod molecules.

(SEQ ID NO: 27)

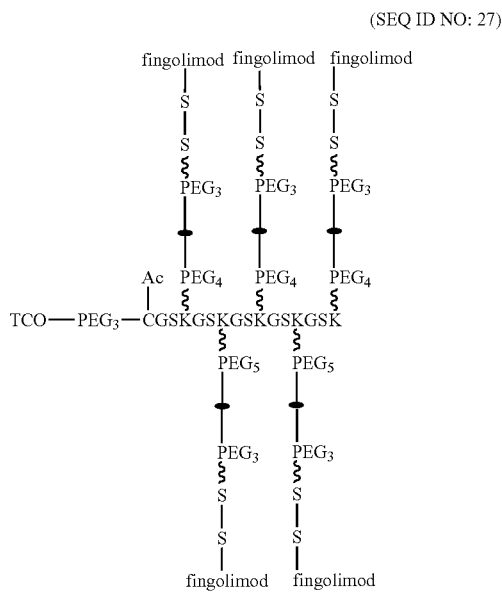

Figure 7:
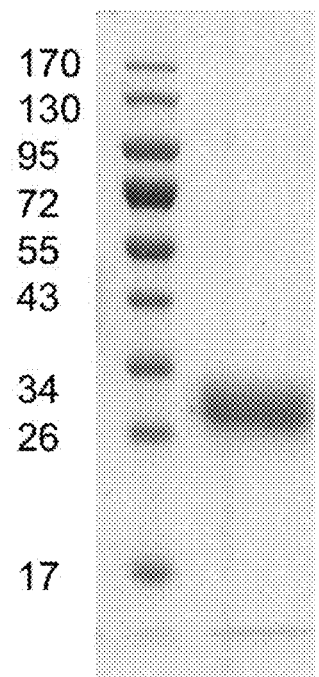

Example 11: Production of Recombinant Ectodomain of Human CD32a by HEK293F Overexpression System The gene-encoding sequence was placed in pG1K expression cassette. The amino acid sequence of the extracellular portion of human CD32a, which was expressed as a recombinant protein with a histidine-tag, is set forth in SEQ ID NO: 28. Recombinant ectodomain of human CD32a was expressed in FreeStyle 293F suspension culture cell expression system and medium (Invitrogen, Carlsbad, USA). FreeStyle 293F cells were seeded at a cell density of $1.0 \times 10^6$ viable cells/ml in 600-ml culture and maintained for 18 to 24 hours prior to transfection to ensure that the cells were actively dividing at the time of transfection. At the time of transfection, $1.0 \times 10^7$ cells in a 96-ml medium in a 2-liter Erlenmeyer shaker flask were transfected by using linear polyethylenimine with an average molecular weight of 25 kDa (Polysciences, Warrington, USA) as a transfection reagent. The transfected cells were incubated at 37° C. for 4 hours post-transfection in an orbital shaker (125 rpm), and their cell density was then adjusted to $2.5 \times 10^6$ cells/ml with a fresh medium and incubated for 4 to 5 days. Culture supernatants were harvested and protein in the media was purified using nickel affinity chromatography. FIG. 7 shows SDS-PAGE analysis of purified protein of ectodomain of human CD32a.

Figure 8:
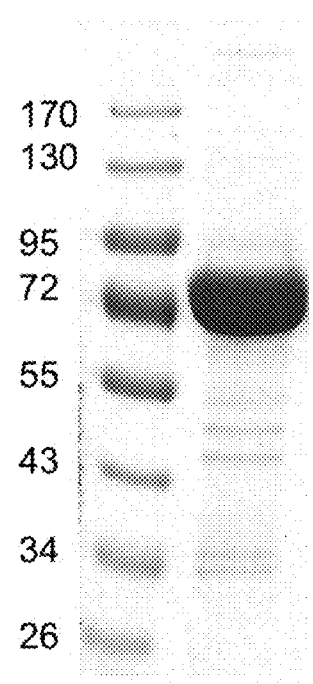
FIG. 8 shows the SDS-PAGE analysis result of the purified ectodomain of human TfR1.

Example 12: Production of Recombinant Ectodomain of Human Transferrin-1 Receptor (TfR) by HEK293F Overexpression System The gene-encoding sequence was placed in pG1K expression cassette. The amino acid sequence of the ectodomain of human TfR1, which was expressed as a recombinant protein with a histidine-tag, is set forth in SEQ ID NO: 29. Recombinant ectodomain of human TfR1 was expressed in FreeStyle 293F suspension culture cell expression system and medium (Invitrogen, Carlsbad, USA). FreeStyle 293F cells were seeded at a cell density of $1.0 \times 10^6$ viable cells/ml in 600-ml culture and maintained for 18 to 24 hours prior to transfection to ensure that the cells were actively dividing at the time of transfection. At the time of transfection, 1.0×10⁷ cells in 96-ml medium in a 2-liter Erlenmeyer shaker flask were transfected by using linear polyethylenimine with an average molecular weight of 25 kDa (Polysciences, Warrington, USA) as a transfection reagent. The transfected cells were incubated at 37° C. for 4 hours post-transfection in an orbital shaker (125 rpm), and their cell density was then adjusted to 2.5×10⁶ cells/ml with a fresh medium and incubated for 4 to 5 days. Culture supernatants were harvested and protein in the media was purified using nickel affinity chromatography. FIG. 8 shows SDS-PAGE analysis of the purified protein of ectodomain of human TfR1.

Example 13: Production of scFv of mAb Specific for Protein F of RSV, mAb Specific for Endotoxin, and mAb Specific for Ectodomain of CD32a by Expi293F Overexpression System The $V_L$ and $V_H$ of the scFv specific for Protein F of RSV were from monoclonal antibody palivizumab; the $V_L$ and $V_H$ of the scFv specific for endotoxin were from monoclonal antibody WN1 222-5 (U.S. Pat. No. 5,858,728); $V_L$ and $V_H$ of the scFv specific for ectodomain of CD32a were from MDE-8 (US Patent Application publication US2007/0253958). The scFv derived from those antibodies were designed to contain a flexible linker of GGGGSGGGGS (residues 241-250 of SEQ ID NO:33) and a terminal cysteine residue at the C-terminus. The cysteine residue provides a sulfhydryl group for conjugation with maleimide group present at the free ends of linking arms in various linker units. To produce the scFv of mAb specific for Protein F of RSV, mAb specific for endotoxin, and mAb specific for extracellular component of CD32a, the $V_L$ and $V_H$ DNA sequences of the three antibodies with further codon optimization were used. DNA sequences encoding $V_L$-GSTSGSGKPGSGEGSTKG (residues 109-126 of SEQ ID NO:33)-$V_H$-SEQ ID NO:6 (GGGGS)₂—C were synthesized. The amino acid sequences of the scFv of mAb specific for Protein F of RSV, mAb specific for endotoxin, and mAb specific for ectodomain of CD32a prepared for the experiments of the invention are set forth in SEQ ID NOs: 30 to 32, respectively.

For preparing scFv proteins using a mammalian expression system, an overexpression system based on Expi293F™ cell line were used for experimentation. The system employed ExpiFectamine™ 293 transfection kit (Life Technologies, Carlsbad, USA) consisting of the Expi293F™ cell line, the cationic lipid-based ExpiFectamine™ 293 Reagent and ExpiFectamine™ 293 transfection Enhancers 1 and 2, and the medium, which was part of the expression system (Gibco, N.Y., USA).

The scFv-encoding sequence was placed in pG1K expression cassette. Expi293F cells were seeded at a density of 2.0×10⁶ viable cells/ml in Expi293F expression medium and maintained for 18 to 24 hours prior to transfection to ensure that the cells were actively dividing at the time of transfection. At the time of transfection, 7.5×10⁸ cells in 255 ml medium in a 2-liter Erlenmeyer shaker flask were transfected by ExpiFectamine™ 293 transfection reagent. The transfected cells were incubated at 37° C. for 16 to 18 hours post-transfection in an orbital shaker (125 rpm) and the cells were added ExpiFectamine™ 293 transfection enhancer 1 and enhancer 2 to the shaker flask, and incubated for 5 to 6 days. Culture supernatants were harvested and scFv proteins in the media were purified using Protein L affinity chromatography.

Figure 9D:
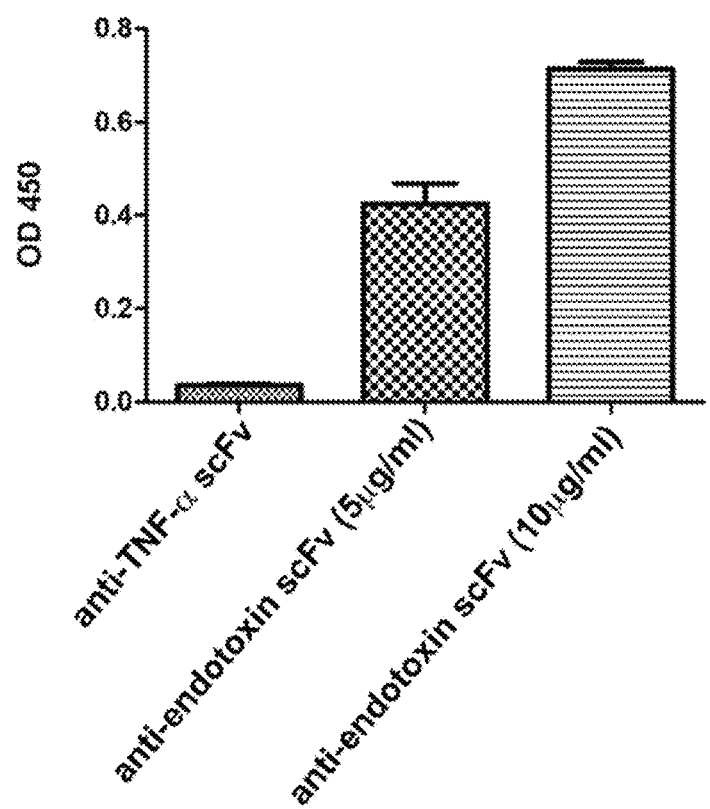
FIG. 9D shows the ELISA analysis of the purified scFv specific for endotoxin.
Figure 9E:
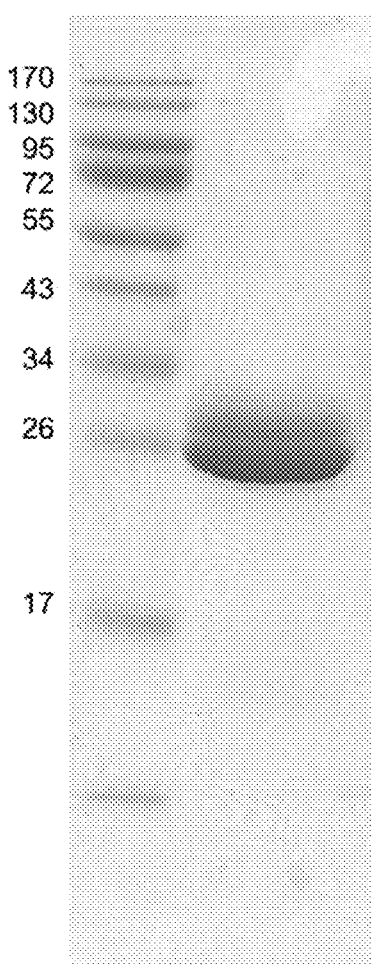
Figure 9F:
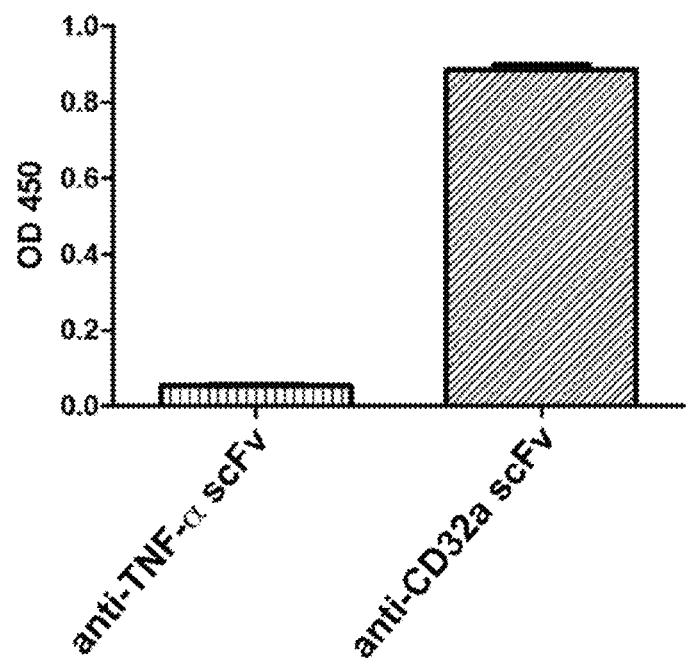

FIGS. 9A and 9B show SDS-PAGE and ELISA analyses of purified scFv of mAb specific for Protein F of RSV; FIGS. 9C and 9D show SDS-PAGE and ELISA analyses of purified scFv of mAb specific for endotoxin; FIGS. 9E and 9F show SDS-PAGE and ELISA analyses of purified scFv of mAb specific for ectodomain of CD32a. The 96-well ELISA plates (Greiner Bio-one) were coated with 5 µg/ml of Protein F of RSV, 10 µg/ml of endotoxin, and 5 µg/ml of ectodomain of CD32a, respectively. Purified scFvs were detected by HRP-conjugated protein L at a ratio of 1:5000.

The ELISA results show that each purified scFv protein bound specifically to its antigen (Protein F of RSV, endotoxin, or ectodomain of TfR1 protein), using adalizumab scFv (anti-TNF-α scFv) as a negative control.

Example 14: Production of scFv of mAb Specific for Ectodomain of TfR1 and mAb Specific for β-Amyloid by Expi293F Overexpression System The $V_L$ and $V_H$ of the scFv specific for ectodomain of TfR1 were from monoclonal antibody OX26; the $V_L$ and $V_H$ of the scFv specific for β-amyloid were from monoclonal antibody bapineuzumab. The scFv derived from those antibodies were designed to contain a flexible linker of GGGGSGGGGS and a terminal cysteine residue at the C-terminus. The cysteine residue provides a sulfhydryl group for conjugation with maleimide group present at the free ends of linking arms in various linker units. To produce the scFv of mAb specific for ectodomain of TfR1 and mAb specific for -β-amyloid, the $V_L$ and $V_H$ DNA sequences of the two antibodies with further codon optimization were used. DNA sequences encoding $V_L$-GSTSGSGKPGSGEGSTKG (residues 109-126 of SEQ ID NO:33)-$V_H$-SEQ ID NO:6 (GGGGS)₂—C were synthesized. The amino acid sequences of the scFv of mAb specific for ectodomain of TfR1 and mAb specific for β-amyloid prepared for the experiments of the invention are set forth in SEQ ID NOs: 33 and 34, respectively.

For preparing scFv proteins using mammalian expression systems, the overexpression system based on Expi293F™ cell line were used. The system employed ExpiFectamine™ 293 transfection kit (Life Technologies, Carlsbad, USA) consisting of the Expi293F™ cell line, the cationic lipid-based ExpiFectamine™ 293 Reagent and ExpiFectamine™ 293 transfection Enhancers 1 and 2, and the medium (Gibco, N.Y., USA).

Figure 10A:
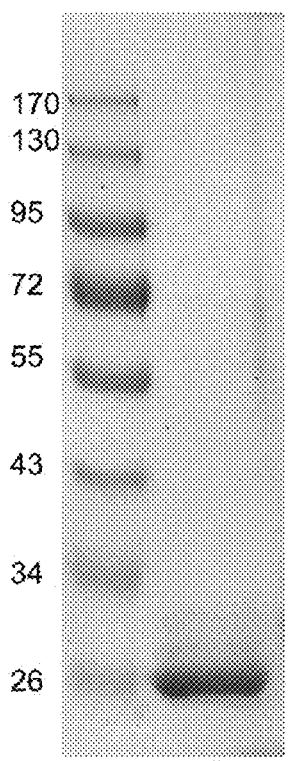
FIG. 10A shows the SDS-PAGE analysis result of the purified scFv specific for the ectodomain of rat TfR1.
Figure 10C:
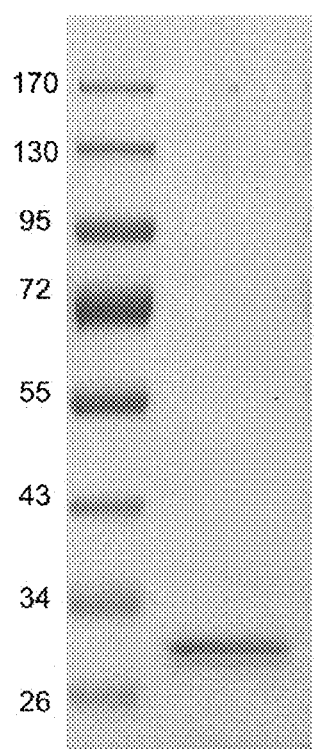
FIG. 10C shows the SDS-PAGE analysis result of the purified scFv specific for β-amyloid.
Figure 10B:
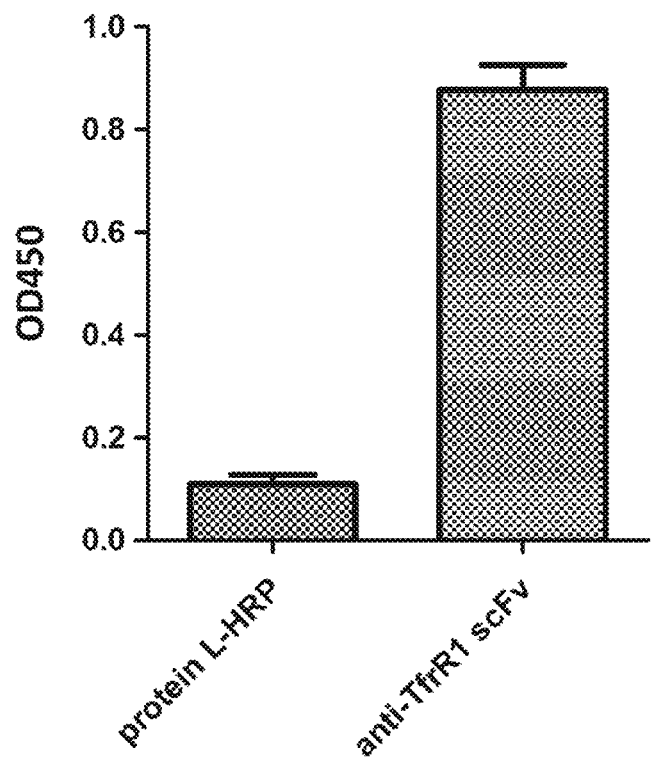
FIG. 10B shows the ELISA analysis result of the purified scFv specific for the ectodomain of rat TfR1.
Figure 10D:
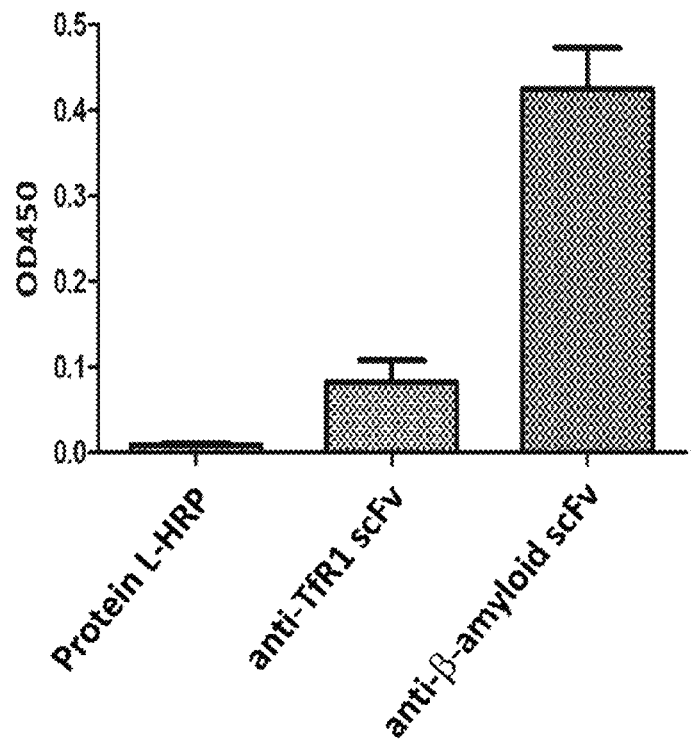
FIG. 10D shows the ELISA analysis of the purified scFv specific for β-amyloid.

The scFv-encoding sequence was placed in pG1K expression cassette. Expi293F cells were seeded at a density of 2.0×10⁶ viable cells/ml in Expi293F expression medium and maintained for 18 to 24 hours prior to transfection to ensure that the cells were actively dividing at the time of transfection. At the time of transfection, 7.5×10⁸ cells in 255 ml medium in a 2-liter Erlenmeyer shaker flask were transfected by ExpiFectamine™ 293 transfection reagent. The transfected cells were incubated at 37° C. for 16 to 18 hours post-transfection in an orbital shaker (125 rpm) and the cells were added ExpiFectamine™ 293 transfection enhancer 1 and enhancer 2 to the shaker flask, and incubated for 5 to 6 days. Culture supernatants were harvested and scFv proteins in the media were purified using Protein L affinity chromatography. FIGS. 10A and 10B respectively show SDS-PAGE and ELISA analyses of purified scFv of mAb specific for ectodomain of TfR1. FIGS. 10C and 10D respectively show SDS-PAGE and ELISA analyses of purified scFv of mAb specific for β-amyloid. The ELISA plates were coated with 5 µg/ml of ectodomain of TfR1 and 5 µg/ml of β-amyloid, respectively. Purified scFvs were detected by HRP-conjugated protein L at a ratio of 1:5000.

The ELISA results show that each purified scFv protein bound specifically to its antigen (ectodomain of TfR1 or β-amyloid), using HRP-conjugated protein L alone as a negative control.

Example 15: Construction and Selection of Phage-Displayed scFvs Specific for Ectodomain of Human CD32a The phage clones carrying the scFv specific for the ectodomain of human CD32a were obtained through a contractual arrangement with Dr. An-Suei Yang's laboratory at the Genomics Research Center, Academia Sinica, Taipei, Taiwan. The framework sequence of the GH2 scFv library was derived from G6 anti-VEGF Fab (Protein Bank Code 2FJG) and cloned into restriction sites SfiI and NotI of phagemid vector pCANTAB5E (GE Healthcare), carrying an ampicillin resistance, a lacZ promotor, a pelB leader sequence for secretion of scFv fragments into culture supernatants, a E-tag applicable for detection. The $V_H$ and $V_L$ domains of the scFv template were diversified separately based on the oligonucleotide-directed mutagenesis procedure; the three CDRs in each of the variable domains were diversified simultaneously. The scFv library of over $10^9$ clones was used for selections on ectodomain of CD32a.

Maxisorp 96-well plates (Nunc) coated with recombinant CD32a proteins (1 μg/100 μL PBS per well) were used for panning anti-CD32a antibodies. In brief, the wells were coated with human CD32a by shaking the coating solution in the wells for 2 hours at room temperature. The CD32a-coated wells were then treated with blocking buffer (5% skim milk in PBST (phosphate buffered saline with 0.1% tween-20)) for 1 hour at room temperature. Recombinant phages in the blocking buffer diluted to $8 \times 10^{11}$ CFU/ml was added to the CD32a-coated wells for 1 hour with gentle shaking; CFU stands for colony-forming unit. The wells were then washed vigorously 10 times with PBST, followed by 6 times with PBS to remove nonspecific binding phages. The bound phages were eluted using 0.1 M HCl/glycine buffer at pH 2.2, and the elution solution was neutralized immediately by 2 M Tris-base buffer at pH 9.0. E. coli strain ER2738 (OD600=~0.6) was used for phage infection at 37° C. for 30 minutes; non-infected E. coli was eliminated by treating with ampicillin for 30 minutes. After ampicillin treatment, helper phage M13KO7 carrying kanamycin resistance was added for another one-hour incubation. The selected phages rescued by helper phage in the E. coli culture were amplified with vigorously shaking overnight at 37° C. in the presence of kanamycin. The amplified phages were precipitated in PEG/NaCl, and then resuspended in PBS for the next selection-amplification cycles. A total of three consecutive panning rounds was performed on ectodomain of CD32a by repeating this selection-amplification procedure.

Figure 11A:
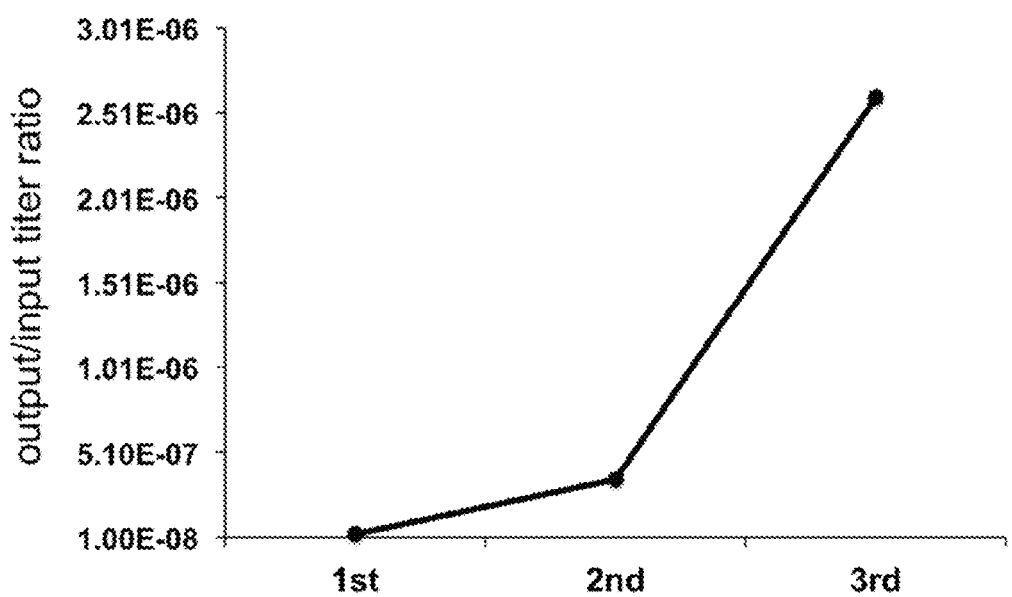

Phage-infected ER2738 colonies of plates with dilution series were counted and phage titers were calculated, yielding the output titer/ml (CFU/ml) per panning round. A 1000-fold increase in phage output title from 1.6E+04 CFU/well to 2.2E+07 CFU/well was obtained after three rounds of panning. The phage output/input titer ratios from each round are shown in FIG. 11A. For each panning round, the phage output/input titer ratios are given on the y-axis. There was clear enrichment of the positive clones over the three rounds of panning. The third panning round resulted in a 100-fold on the ratios of phage output/input titer over the first round, as the binding clones became the dominant population in the library.

In a typical selection procedure, after three rounds of antigen-panning on human CD32a-coated wells in ELISA plates, approximately 80% of the bound phage particles bound to CD32a specifically in ELISA with coated CD32a.

Example 16: Single Colony ELISA Analysis of Phage-Displayed scFvs Specific for Ectodomain of Human CD32a E. coli strain ER2738 infected with single-clonal phages each harboring a selected scFv gene in its phagemid was grown in the mid-log phase in 2YT broth (16 g/L tryptone, 10 g/L yeast extract, 5 g/L NaCl, pH 7.0) with 100 μg/ml ampicillin in deep well at 37° C. with shaking. After broth reaching an OD600 of 1.0, IPTG was added to a final concentration of 1 μg/ml. The plates were incubated at 37° C. overnight with rigorously shaking; thereafter, the plates were centrifuged at 4000 g for 15 minutes at 4° C.

For soluble scFv binding test, ELISA was carried out. In brief, Maxisorp 96-well plate (Nunc) was coated with ectodomain of CD32a (0.5 μg/100 μl PBS per well) or a negative control antigen human transferrin-1 receptor, for 18 hours with shaking at 4° C. After treated with 300 μl of blocking buffer for 1 hour, 100 μl of secreted scFv in the supernatant was mixed with 100 μl of blocking buffer and then added to the coated plate for another 1 hour. Goat anti-E-tag antibody (conjugated with HRP, 1:4000, Cat. No. AB19400, Abcam) was added to the plate for 1 hour. TMB substrate (50 μl per well) was added to the wells and the absorbance at 450 nm was measured after reactions were stopped by adding 1N HCl (50 μl per well).

Figure 11B:
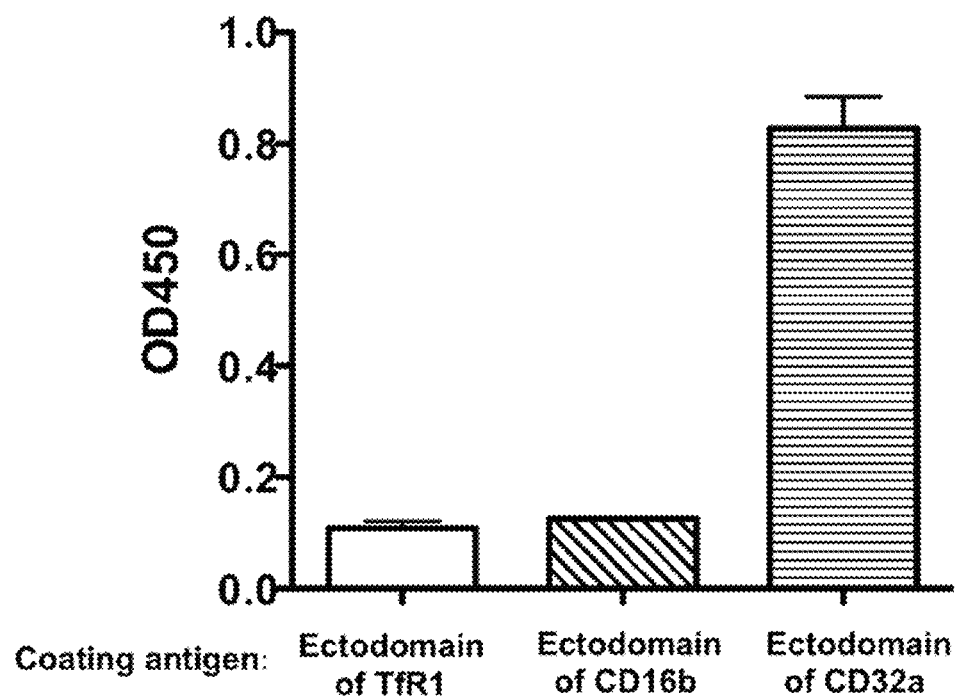

A total of 192 phage clones after the third round of panning were subjected to the present analysis. Among them, 12 scFv clones that bound to CD32a with a differential of OD450 greater than 10 were further characterized by sequencing genes encoding these scFvs. Six different DNA sequences were identified. FIG. 11B shows the ELISA result of an scFv clone 22D1. The amino acid sequence of an scFV clone 22D1, which binds to human CD32a with an OD450 of 0.8, is shown in SEQ ID NO: 35.

Example 17: Construction and Selection of Phage-Displayed scFvs Specific for Ectodomain of Human TfR1

The phage clones carrying the scFv specific for the ectodomain of human TfR1 were obtained through a contractual arrangement with Dr. An-Suei Yang's laboratory at the Genomics Research Center, Academia Sinica, Taipei, Taiwan. The framework sequence of the GH2 scFv library was derived from G6 anti-VEGF Fab (Protein Bank Code 2FJG) and cloned into restriction sites SfiI and NotI of phagemid vector pCANTAB5E (GE Healthcare), carrying an ampicillin resistance, a lacZ promotor, a pelB leader sequence for secretion of scFv fragments into culture supernatants, an E-tag applicable for detection. The $V_H$ and $V_L$ domains of the scFv template were diversified separately based on the oligonucleotide-directed mutagenesis procedure; the three CDRs in each of the variable domains were diversified simultaneously. The scFv library of over $10^9$ clones was used for selections on ectodomain of CD32a.

Maxisorp 96-well plates (Nunc) coated with recombinant ectodomain of TfR1 proteins (1 μg/100 μL PBS per well) were used for panning anti-TfR1 antibodies. In brief, the wells were coated with human TfR1 by shaking the coating solution in the wells for 2 hours at room temperature. The TfR1-coated wells were then treated with blocking buffer (5% skim milk in PBST (phosphate buffered saline with 0.1% tween-20)) for 1 hour at room temperature. Recombinant phages in the blocking buffer diluted to $8 \times 10^{11}$ CFU/ml was added to the TfR1-coated wells for 1 hour with gentle shaking; CFU stands for colony-forming unit. The wells were then washed vigorously 10 times with PBST, followed by 6 times with PBS to remove nonspecific binding phages. The bound phages were eluted using 0.1 M HCl/glycine buffer at pH 2.2, and the elution solution was neutralized immediately by 2 M Tris-base buffer at pH 9.0. E. coli strain ER2738 (OD600=~0.6) was used for phage infection at 37° C. for 30 minutes; non-infected E. coli was eliminated by treating with ampicillin for 30 minutes. After ampicillin treatment, helper phage M13KO7 carrying kanamycin resistance was added for another one-hour incubation. The selected phages rescued by helper phage in the E. coli culture were amplified with vigorously shaking overnight at 37° C. in the presence of kanamycin. The amplified phages were precipitated in PEG/NaCl, and then resuspended in PBS for the next selection-amplification cycles. A total of three consecutive panning rounds was performed on ectodomain of TfR1 by repeating this selection-amplification procedure.

Figure 12A:
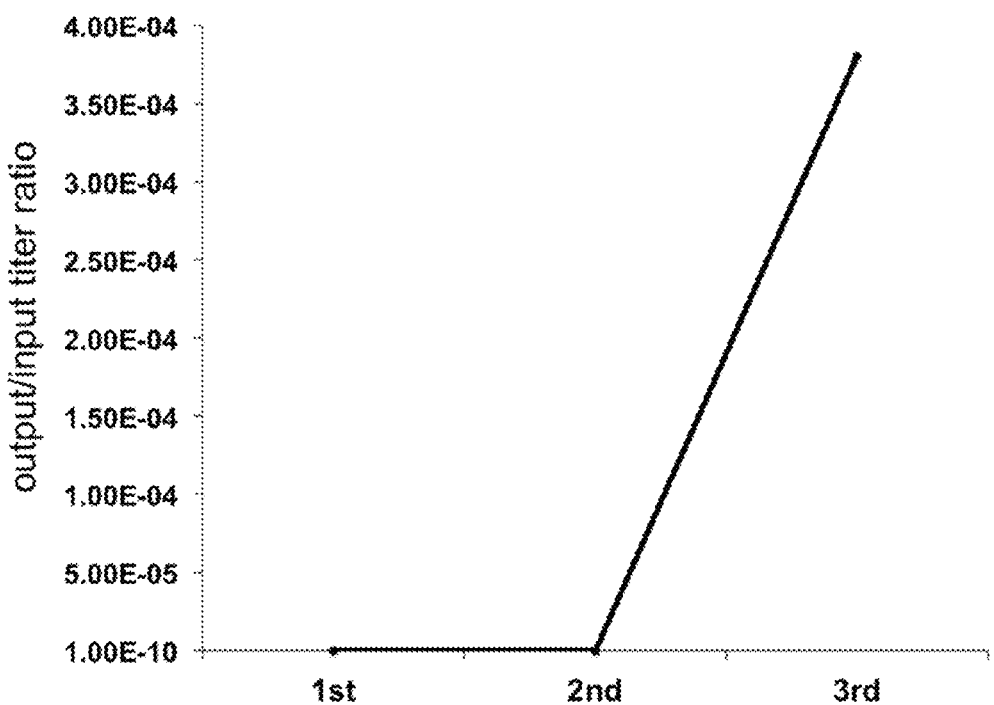
FIG. 12A shows the data of the titers of the phages bearing scFvs specific for ectodomain of human TfR1.

Phage-infected ER2738 colonies of plates with serial dilutions were counted and phage titers were calculated, yielding the output titer/ml (CFU/ml) per panning round. A $10^4$-fold increase in phage output title from 3.74E+03 CFU/well to 1.5E+08 CFU/well was obtained after three rounds of panning. The phage output/input titer ratios from each round are shown in FIG. 12A. For each panning round, the phage output/input titer ratios are given on the y-axis. There was clear enrichment of the positive clones over the three rounds of panning. The third panning round resulted in a $10^4$-fold on the ratios of phage output/input titer over the first round, as the binding clones became the dominant population in the library.

In a typical selection procedure, after three rounds of antigen-panning on human TfR1-coated wells in ELISA plates, approximately 80% of the bound phage particles bound to TfR1 specifically in ELISA with coated TfR1.

Example 18: Single Colony ELISA Analysis of Phage-Displayed scFvs Specific for Ectodomain of Human TfR1

E. coli strain ER2738 infected with single-clonal phages each harboring a selected scFv gene in its phagemid was grown in the mid-log phase in 2YT broth (16 g/L tryptone, 10 g/L yeast extract, 5 g/L NaCl, pH 7.0) with 100 µg/ml ampicillin in deep well at 37° C. with shaking. After broth reaching an OD600 of 1.0, IPTG was added to a final concentration of 1 µg/ml. The plates were incubated at 37° C. overnight with rigorously shaking; thereafter, the plates were centrifuged at 4000 g for 15 minutes at 4° C.

For soluble scFv binding test, ELISA was carried out. In brief, Maxisorp 96-well plate (Nunc) was coated with ectodomain of TfR1 (0.5 µg/100 µl PBS per well) or a negative control antigen CD16b, for 18 hours with shaking at 4° C. After treated with 300 µl of blocking buffer for 1 hour, 100 µl of secreted scFv in the supernatant was mixed with 100 µl of blocking buffer and then added to the coated plate for another one-hour. Goat anti-E-tag antibody (conjugated with HRP, 1:4000, Cat. No. AB19400, Abcam) was added to the plate for 1 hour. TMB substrate (50 µl per well) was added to the wells and the absorbance at 450 nm was measured after reactions were stopped by adding 1N HCl (50 µl per well).

Figure 12B:
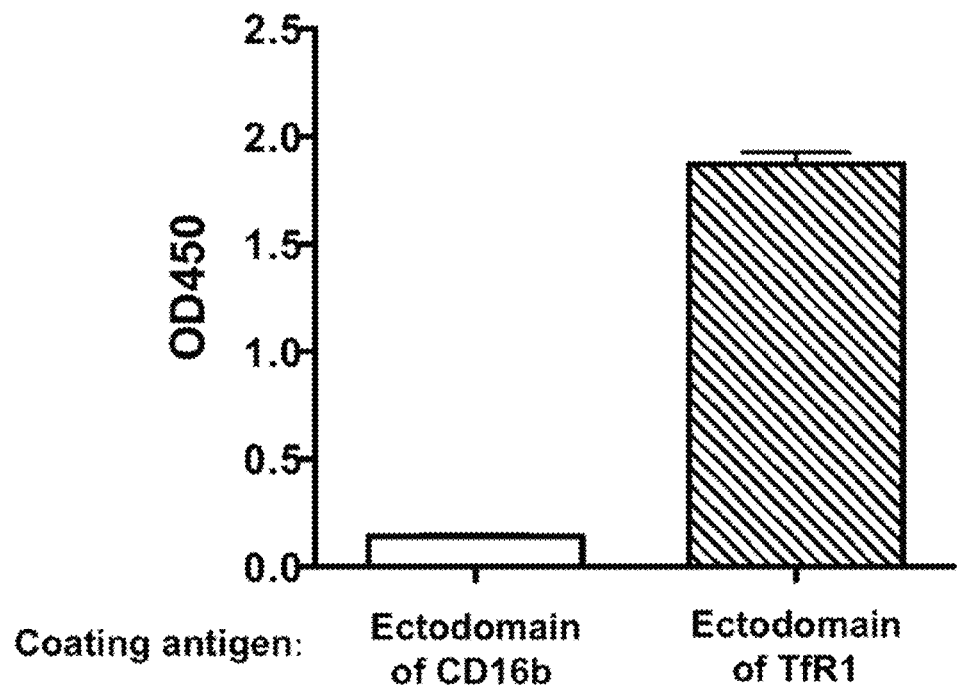
FIG. 12B shows the single colony ELISA analysis of phage-displayed scFvs specific for the ectodomain of human TfR1.

A total of 192 phage clones after the third round of panning were subjected to the present analysis. Among them, 23 scFv clones that bound to TfR1 with a differential of OD450 greater than 10 were further characterized by sequencing the genes encoding these scFvs. Sixteen different DNA sequences were identified. FIG. 12B shows the ELISA result of an scFv clone 12A1. The amino acid sequence of the scFV clone 12A1, which binds to human TfR1 with an OD450 of 1.7, is shown in SEQ ID NO: 36.

Example 19: Preparation of TCO-scFv Specific for the Ectodomain of CD32a

The DNA sequence encoding SEQ ID NO: 32 was synthesized and expressed as in the above Examples. For the conjugation with Mal-PEG$_3$-TCO (Conju-probe, Inc.), the cysteine residue at the C-terminal end of the purified scFv of anti-CD32a mAb was reduced by incubating with 5 mM dithiothreitol (DTT) at room temperature for 4 hours with gentle shaking. The buffer of reduced scFv proteins were exchanged to sodium phosphate buffer (100 mM sodium phosphate, pH7.0, 50 mM NaCl, and 5 mM EDTA) by using NAP-10 Sephadex G-25 column. After the reduction reaction and buffer exchange, conjugation was conducted overnight at room temperature in a reaction molar ratio of 10:1 ([Mal-PEG$_3$-TCO:[scFv]]. The excess crosslinker was removed by a desalting column and the TCO-conjugated scFv product was analyzed.

Figure 13A:
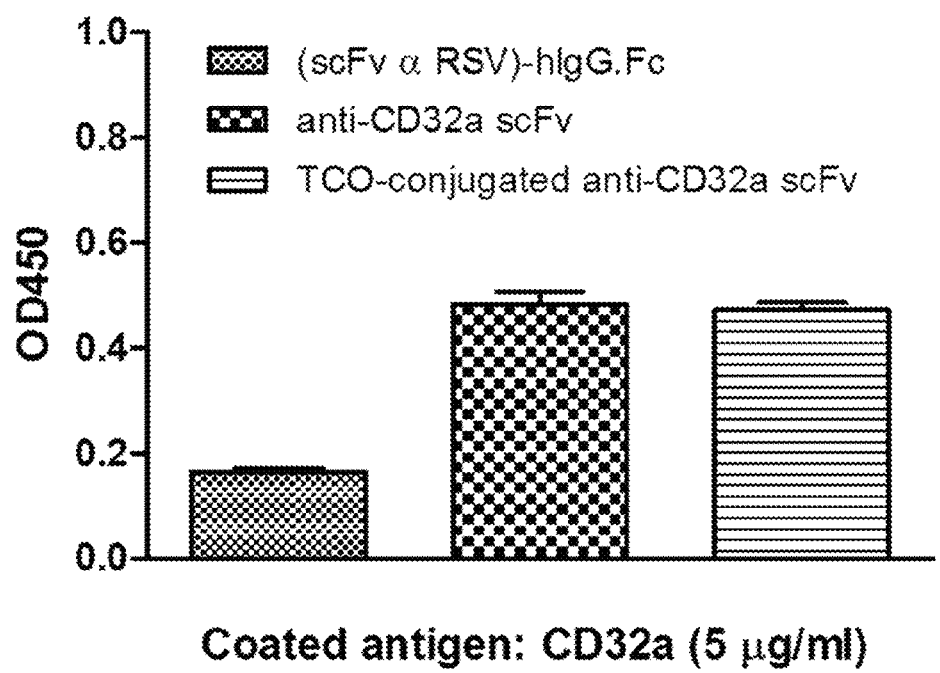
Figure 13B:
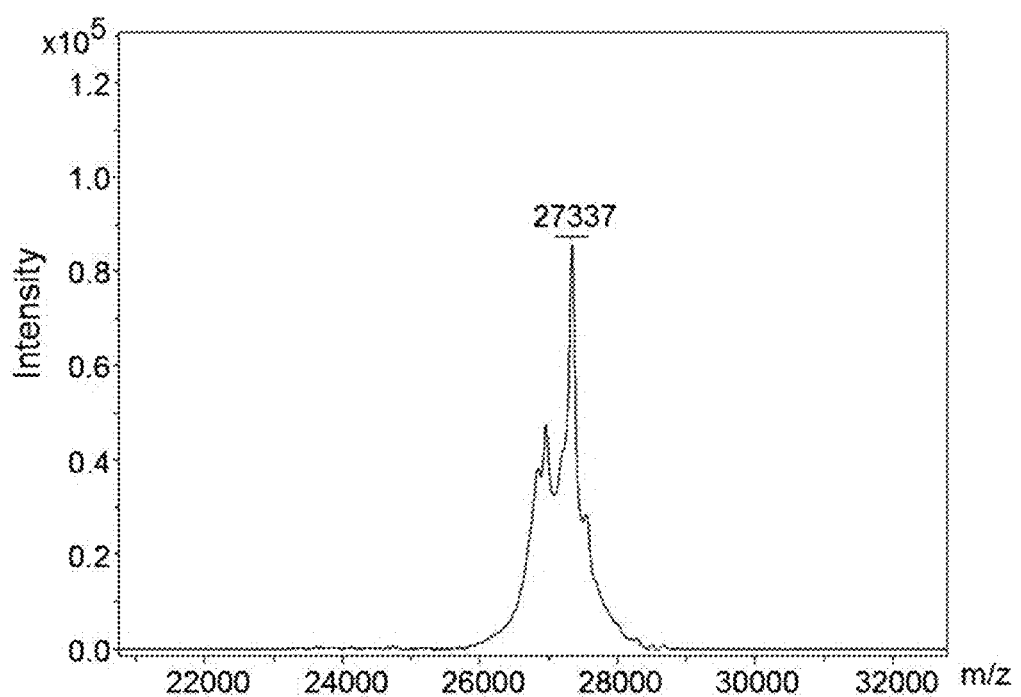

The results of mass spectroscopy MALDI-TOF analysis indicated that the sample of TCO-conjugated scFv specific for CD32a had a m.w. of 27,337 daltons. The purity of TCO-conjugated scFvs specific for CD32 was identified through Coomassie blue staining of 12% SDS-PAGE. FIG. 13A and FIG. 13B show, respectively, the ELISA and Mass spectrometric analysis of TCO-conjugated scFv specific for CD32a, in which unmodified scFv specific for CD32a was used as a positive control. According to the ELISA results, TCO-conjugated scFv specific for CD32a bound to recombinant ectodomain of human CD32a.

Example 20: Preparation of Tetrazine-scFv Specific for the Ectodomain of TfR1

The DNA sequence encoding SEQ ID NO: 33 was synthesized and expressed as in the above Examples. For the conjugation with Mal-PEG$_4$-tetrazine (Conju-probe, Inc.), the cysteine residue at the C-terminal end of the purified scFv of mAb specific for TfR1 was reduced by incubating with 5 mM DTT at room temperature for 4 hours with gentle shaking. The buffer of reduced scFv proteins were exchanged to sodium phosphate buffer (100 mM sodium phosphate, pH 7.0, 50 mM NaCl, and 5 mM EDTA) by using NAP-10 Sephadex G-25 column. After the reduction reaction and buffer exchange, conjugation was conducted overnight at 4° C. in a reaction molar ratio of 10:1 ([Mal-PEG$_4$-tetrazine:[scFv]]. The excess crosslinker was removed by a desalting column and the tetrazine-conjugated scFv product was analyzed.

Figure 14A:
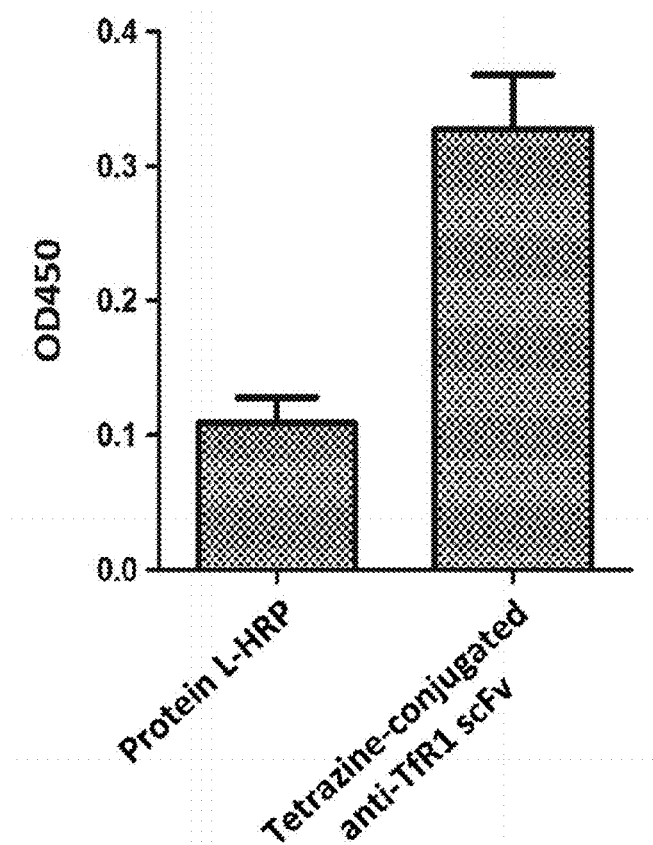
FIG. 14A and FIG. 14B respectively show the results of ELISA analysis and mass spectrometric analysis of tetrazine-conjugated scFv specific for TfR1.
Figure 14B:
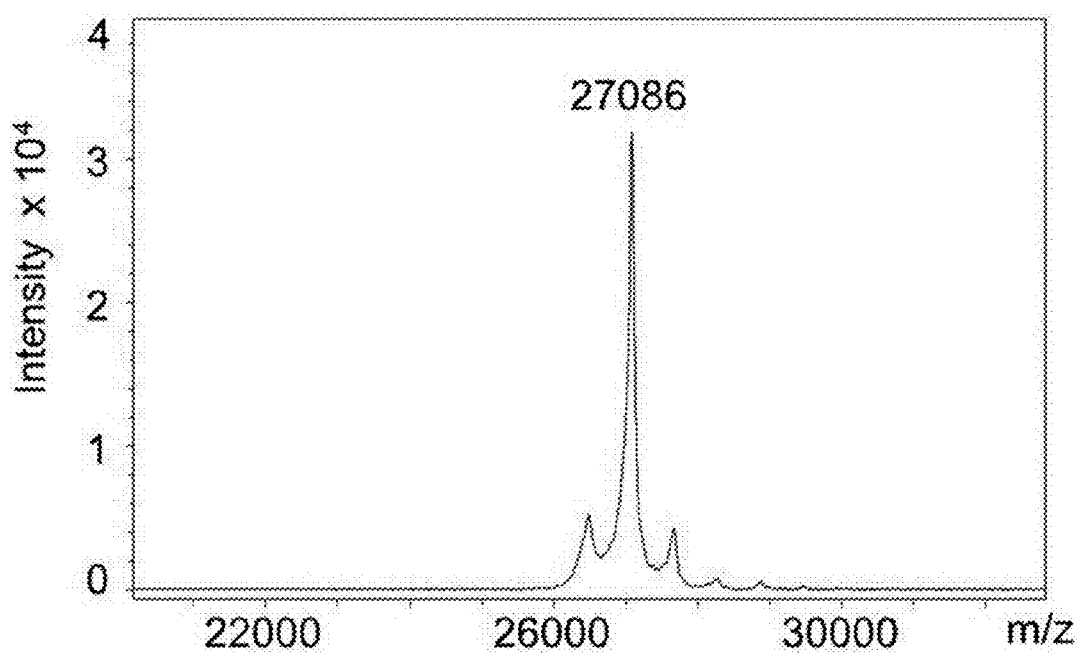

The results of mass spectroscopy MALDI-TOF analysis indicated that the sample of tetrazine-conjugated scFv specific for TfR1 had a m.w. of 27,086 daltons. The purity of tetrazine-conjugated scFv specific for TfR1 was identified through Coomassie blue staining of 12% SDS-PAGE. FIG. 14A and FIG. 14B show, respectively, the ELISA and Mass spectrometric analysis of tetrazine-conjugated scFv specific for TfR1, in which unmodified scFv specific for TfR1 was used as a positive control. According to the ELISA results, tetrazine-conjugated scFv specific for TfR1 bound to recombinant ectodomain of TfR1.

Example 21: Conjugation of Three scFvs Specific for Endotoxin to the Three Maleimide-PEG$_{12}$ Linking Arms Based on Tetrazine-Peptide 1

This example demonstrates that three scFvs can be conjugated to the three PEG$_{12}$-maleimide linking arms based on tetrazine-peptide 1. Prior to conjugation with the tetrazine-peptide 1 that had three PEG$_{12}$-maleimide linking arms, scFv specific for endotoxin was incubated with DTT at a molar ratio of 2:1 ([DTT]:[scFv]) at 25° C. for 4 hours with gentle shaking to keep its C-terminal cysteine in a reduced form. Subsequently, the buffer of reduced scFv specific endotoxin was exchanged to maleimide-SH coupling reaction buffer (100 mM sodium phosphate, pH 7.0, 50 mM NaCl and 5 mM EDTA) by using an NAP-10 Sephadex G-25 column (GE Healthcare). After the reduction and buffer exchange, the conjugation to the tetrazine-peptide 1 having three maleimide-PEG$_{12}$ linking arms was conducted overnight at 4° C. at a molar ratio of 1:4 ([linker]:[Protein]).

The PEG$_{12}$-maleimide-conjugated tetrazine-peptide 1 conjugated with three scFvs specific for endotoxin was separated from the free scFv, free PEG$_{12}$-maleimide-conjugated tetrazine-peptide 1 and the PEG$_{12}$-maleimide-conjugated tetrazine-peptide 1 conjugated with one and two scFvs specific for endotoxin by size exclusion chromatography column S75.

Figure 15A:
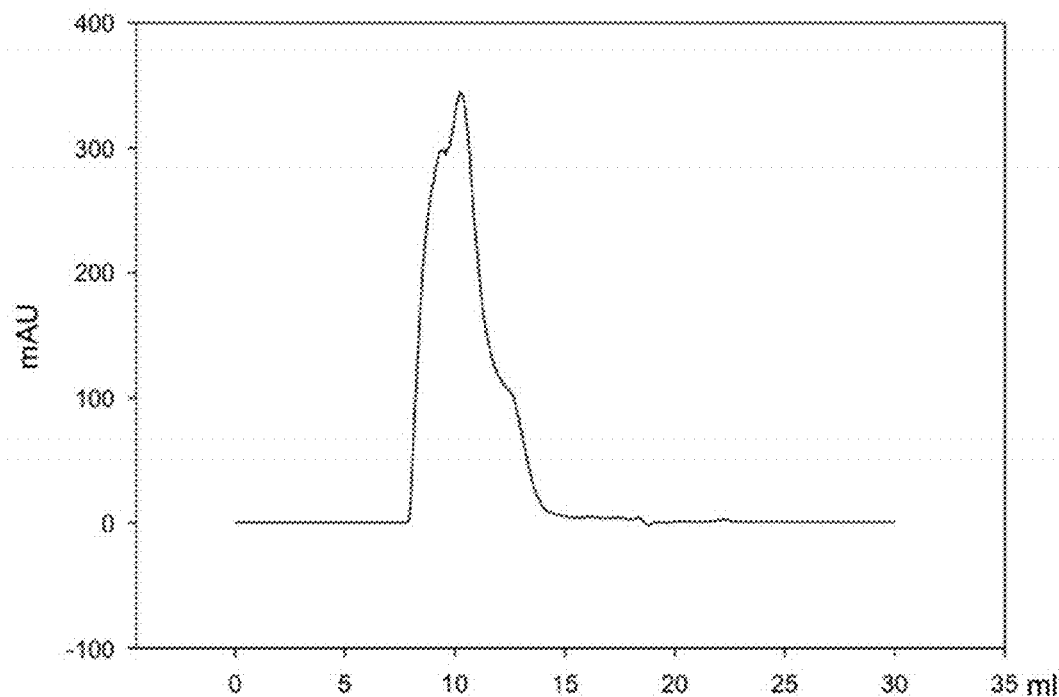
FIG. 15A shows the FPLC elution profile of size-exclusion column S75 on the synthesized targeting linker unit composed of a linker unit with a free tetrazine functional group and a set of three scFvs specific for endotoxin as targeting elements.
Figure 15B:
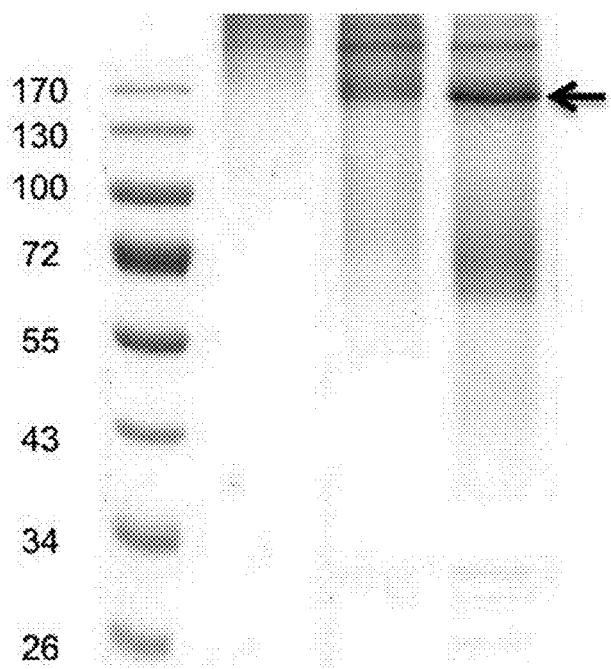
FIG. 15B and FIG. 15C respectively show the results of the SDS-PAGE analysis result and the ELISA result of the synthesized targeting linker unit of FIG. 15A.

FIG. 15A is the FPLC elution profile on a synthesized targeting linker unit composed of a linker unit with a free tetrazine functional group and a set of three scFvs specific for endotoxin as targeting elements with retention volume of 9.5 ml. The product (i.e., the PEG$_{12}$-maleimide-conjugated tetrazine-peptide 1 having a free tetrazine functional group and being conjugated with a set of three scFvs specific for endotoxin) was purified in the elution fraction and shown in lane 4 (indicated by arrow) of the 10% SDS-PAGE analysis shown in FIG. 15B.

Figure 15C:
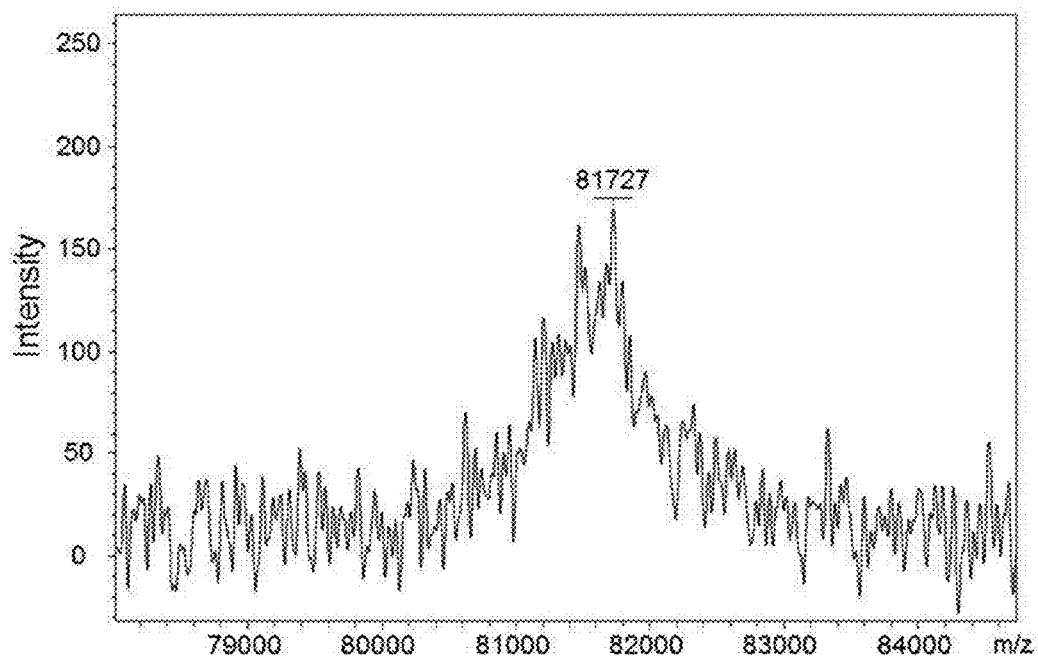

Example 22: Analysis of a Targeting Linker Unit Containing Three scFvs Specific for Endotoxin Linked to the Three Maleimide-PEG$_{12}$ Linking Arms Based on Tetrazine-Peptide 1 by MALDI-TOF The sample of the targeting linker unit with three scFvs specific for endotoxin linked to the three maleimide-PEG$_{12}$ linking arms based on tetrazine-peptide 1 was analyzed by MALDI-TOF. The median of the experimental molecular weight was consistent with the median of theoretical molecular weight of three scFvs specific for endotoxin conjugated to tetrazine-peptide 1 with three maleimide-PEG$_{12}$ linking arms. According to the mass spectrometric profile in FIG. 15C, the present targeting linker unit had a median molecular weight of 81,727 daltons.

Illustrated below is the synthesized targeting linker unit that was composed of a linker unit with a free tetrazine functional group and a set of three scFvs specific for endotoxin as targeting elements.

scFv α endotoxin
scFv α endotoxin —( C )— Tetrazine
scFv α endotoxin

Example 23: Preparation of a Targeting Linker Unit Based on Tetrazine-Peptide 1 with Three scFvs Specific for Protein F of RSV The conjugation of scFv to the linker unit and the purification and analysis of the product were the same as in the preceding Examples.

Figure 16:
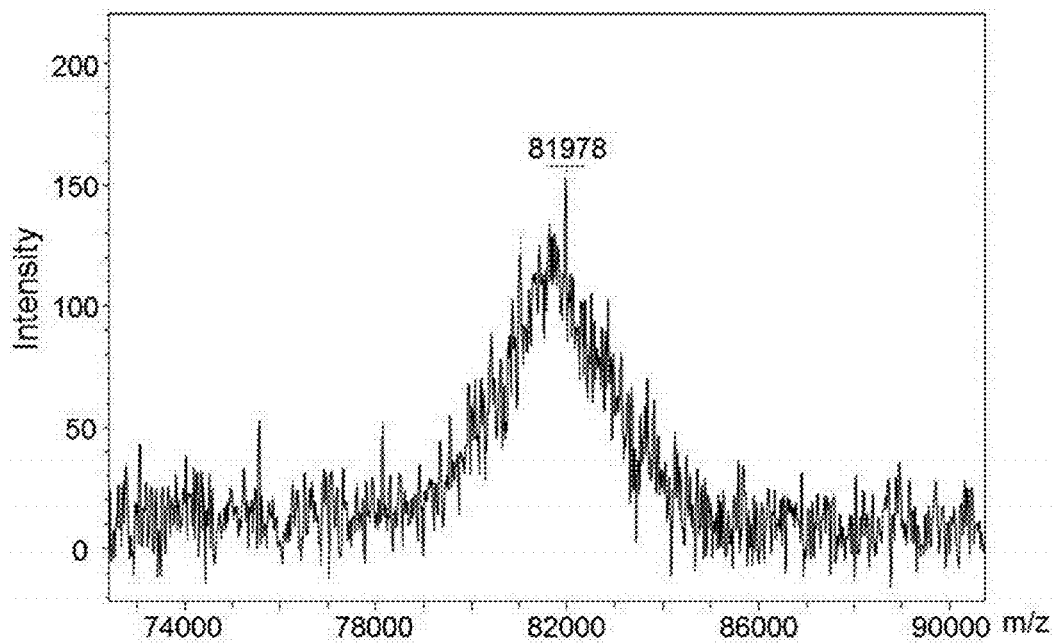
FIG. 16 shows the mass spectrometric analysis result of the synthesized targeting linker unit that was composed of a linker unit with a free tetrazine functional group and a set of three scFv specific for Protein F of RSV as targeting elements.

Shown in FIG. 16 is the mass spectrometric analysis of the synthesized targeting linker unit that was composed of a linker unit with a free tetrazine functional group and a set of three scFv specific for Protein F of RSV as targeting elements (illustrated below). As indicated in FIG. 16, this effector linker unit had a molecular weight of 81,978 daltons.

scFv α RSV
scFv α RSV —( C )— Tetrazine
scFv α RSV

Example 24: Conjugation of Three scFvs Specific for β-Amyloid to Three Maleimide-PEG$_{12}$ Linking Arms Based on TCO-Peptide 1

This example was performed to demonstrate that three scFvs could be conjugated to the three maleimide-PEG$_{12}$ linking arms based on TCO-peptide 1. Prior to conjugation with the TCO-peptide 1 that had three maleimide-PEG$_{12}$ linking arms, scFv specific for β-amyloid was incubated with DTT at a molar ratio of 2:1 ([DTT]:[scFv]) at room temperature for 4 hours with gentle shaking to keep its C-terminal cysteine in a reduced form. Subsequently, the buffer of reduced scFv specific for β-amyloid was exchanged to maleimide-SH coupling reaction buffer (100 mM sodium phosphate, pH 7.0, 50 mM NaCl and 5 mM EDTA) by using an NAP-10 Sephadex G-25 column (GE Healthcare). After the reduction and buffer exchange, the conjugation to the TCO-peptide 1 having three maleimide-PEG$_{12}$ linking arms was conducted overnight at room temperature at a molar ratio of 1:4 ([linker]:[Protein]).

The reaction mixture of the preceding examples was adjusted to pH 5.0 and then applied to pre-equilibrated (5 mM EDTA, and 50 mM sodium acetate at pH 5.0) cation exchange column SP Sepharose FF (GE Healthcare). The maleimide-PEG$_{12}$-conjugated TCO-peptide 1 conjugated with three scFvs specific for β-amyloid was eluted using a linear gradient of 0-500 mM sodium chloride in a flow rate of 0.5 ml/min for 100 minutes. The maleimide-PEG$_{12}$-conjugated TCO-peptide 1 conjugated with three scFvs specific for β-amyloid was separated from the free scFv, free maleimide-PEG$_{12}$-conjugated TCO-peptide 1 and the maleimide-PEG$_{12}$-conjugated TCO-peptide 1 conjugated with one and two scFvs specific for β-amyloid by cation exchange column SP Sepharose FF. The purified product, maleimide-PEG$_{12}$-conjugated TCO-peptide 1 conjugated with three scFvs specific for β-amyloid, was concentrated and buffer-exchange into click reaction buffer, 100 mM potassium phosphate at pH 7.0.

Figure 17A:
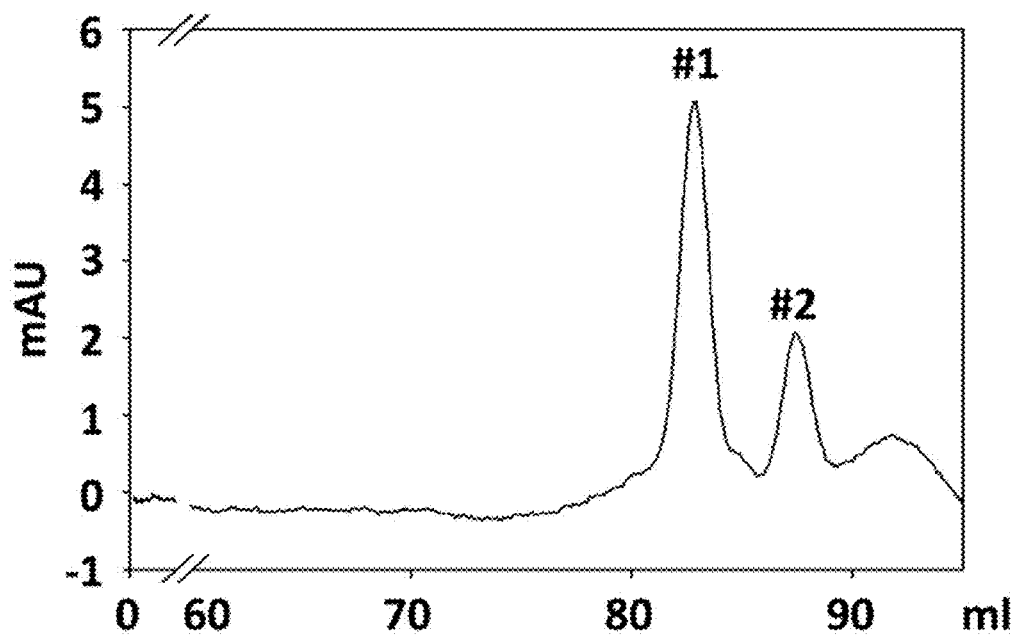
FIG. 17A shows the FPLC elution profile of cation ion exchange column on a synthesized targeting linker unit composed of a linker unit with a free TCO functional group and a set of three scFvs specific for β-amyloid as targeting elements.
Figure 17B:
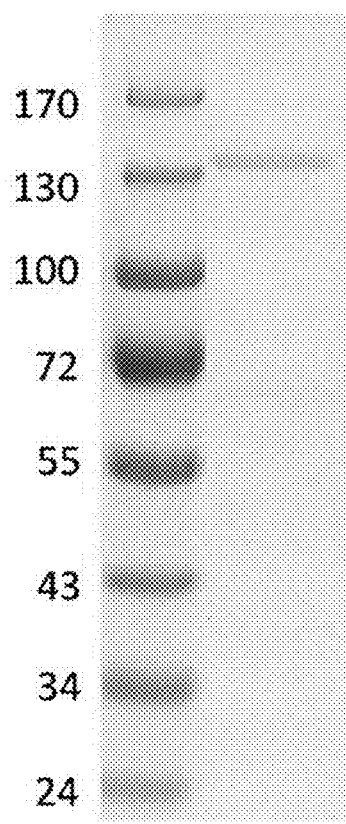
FIG. 17B and FIG. 17O respectively show the results of the SDS-PAGE analysis result and the ELISA result of the synthesized targeting linker unit of FIG. 17A.

FIG. 17A is the FPLC elution profile of cation exchange column SP Sepharose FF on a synthesized effector linker unit composed of a linker unit with a free TCO functional group and a set of three scFvs specific for β-amyloid as effector elements. Symbol #1 and #2 respectively represented the eluted peaks of maleimide-PEG$_{12}$-conjugated TCO-peptide 1 conjugated with two scFvs and three scFvs specific for β-amyloid. The product, the maleimide-PEG$_{12}$-conjugated TCO-peptide 1 bearing a free TCO functional group and three scFvs specific for β-amyloid was purified and revealed in lane 2 of the 8% SDS-PAGE analysis shown in FIG. 17B.

Figure 17C:
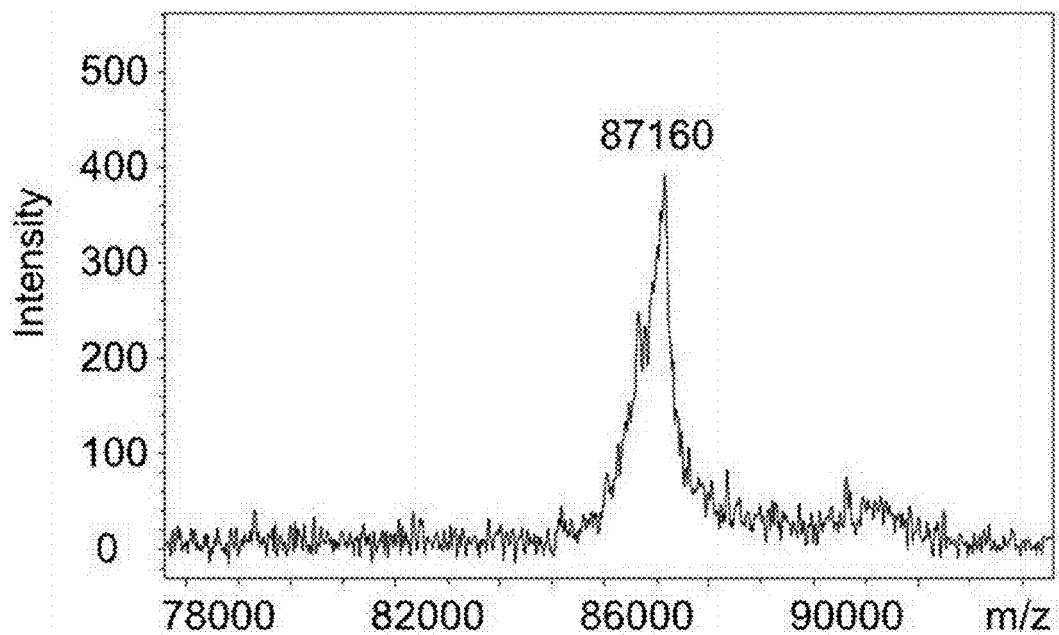

Example 25: Analysis of an Effector Linker Unit Containing Three scFvs Specific for β-Amyloid Linked to the Three Maleimide-PEG$_{12}$ Linking Arms Based on TCO-Peptide 1 by MALDI-TOF The sample of the targeting linker unit of three scFvs specific for β-amyloid linked to the three maleimide-PEG$_{12}$ linking arms based on TCO-peptide 1 was analyzed by MALDI-TOF. The median of the experimental molecular weight was consistent with the median of theoretical molecular weight of three scFvs specific for 3-amyloid conjugated to TCO-peptide 1 with three maleimide-PEG$_{12}$ linking arms. According to the mass spectrometric profile in FIG. 17C, the synthesized targeting linker unit had the median molecular weight of 87,160 daltons.

Illustrated herein is the synthesized targeting linker unit that was composed of a linker unit with a free TCO functional group and a set of three scFvs specific for β-amyloid as targeting elements.

Example 26: Preparation of Molecular Construct with Three scFvs Specific for Protein F of RSV as Targeting Elements and One scFv Specific for Ectodomain of CD32a as an Effector Element In this example, the targeting linker unit of the preceding examples and a TCO-scFv specific for extodomain of CD32a were coupled via a tetrazine-TCO iEDDA reaction. Specifically, the targeting linker unit had three scFv specific for Protein F of RSV and one free tetrazine group.

Figure 18A:
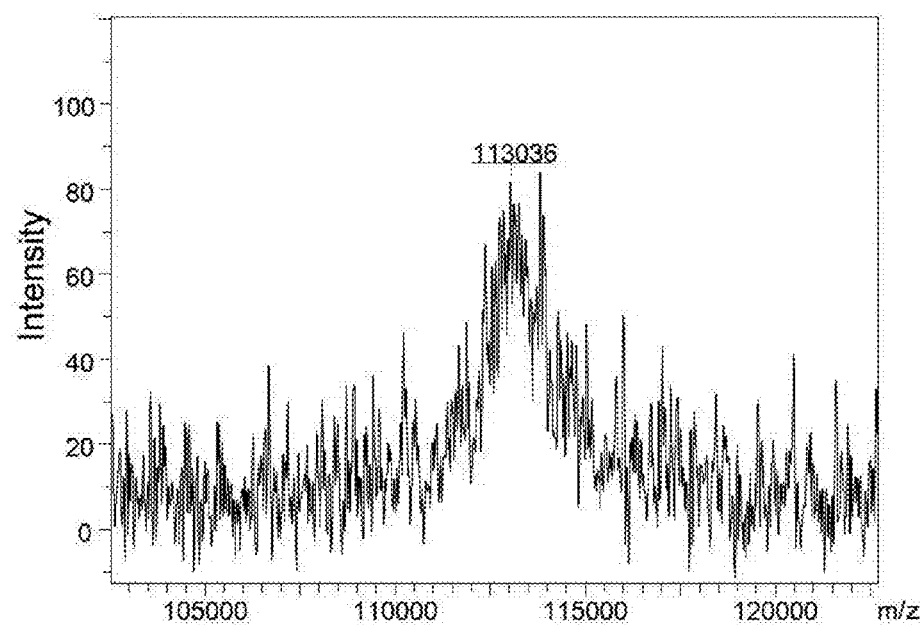
FIG. 18A shows the mass spectrometric analysis result of a single linker unit molecular construct with three scFvs specific for endotoxin as targeting elements and one scFv specific for ectodomain of CD32a as an effector element.

The procedure for tetrazine-TCO ligation was performed per the manufacturer's instructions (Jena Bioscience GmbH, Jena, Germany). Briefly, 100 μl of the targeting linker unit (0.3 mg/ml) was added to the solution containing the effector element at a molar ratio of 1:1.2 ([tetrazine]:[TCO]). The reaction mixture was incubated for 1 hour at room temperature. The product was subjected to mass spectrometric analysis, and the result indicated a molecular weight of 113,036 daltons (FIG. 18A).

The product, a single linker unit molecular construct with three scFvs specific for Protein F of RSV as targeting elements and one scFv specific for ectodomain of CD32a as an effector element, is illustrated herein.

Example 27: Preparation of Molecular Construct with Three scFvs Specific for Endotoxin as Targeting Elements and One scFv Specific for Ectodomain of CD32a as an Effector Element The targeting linker unit prepared in an earlier Example and the TCO-scFv specific for ectodomain of CD32a were coupled via a tetrazine-TCO iEDDA reaction.

Figure 18B:
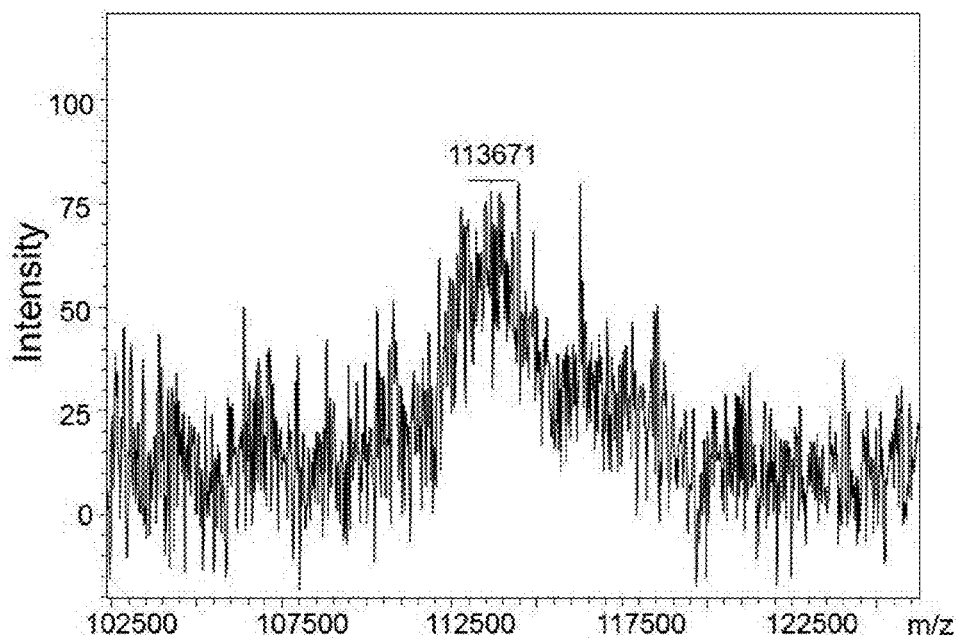
FIG. 18B shows the mass spectrometric analysis result of a single linker unit molecular construct with three scFvs specific for endotoxin as targeting elements and one scFv specific for ectodomain of CD32a as an effector element.

The procedure for tetrazine-TCO ligation was performed as described in the previous Example. The product, as illustrated below, was a single linker unit molecular construct with three scFvs specific for endotoxin as targeting elements and one scFv specific for ectodomain of CD32a as an effector element. The mass spectrometric analysis shown in FIG. 18B indicated that this molecular construct had a molecular weight of 113,761 daltons.

Example 28: Preparation of Molecular Construct with One scFv Specific for Ectodomain of TfR1 as a Targeting Element and Three scFvs Specific for β-Amyloid as Effector Elements The targeting linker unit prepared in an earlier Example and the tetrazine-scFv specific for ectodomain of TfR1 were coupled via a tetrazine-TCO iEDDA reaction.

Figure 18C:
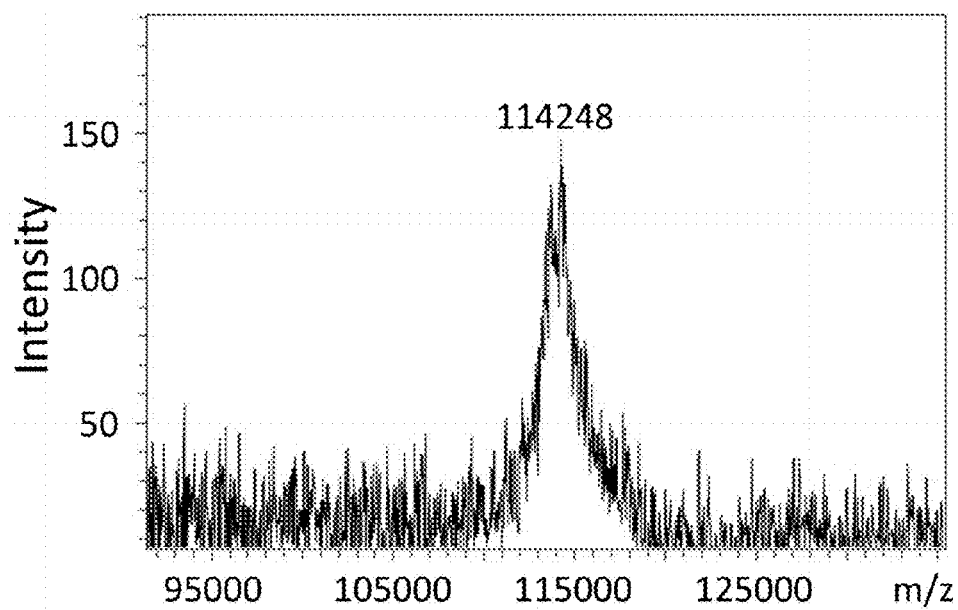
FIG. 18C shows the mass spectrometric analysis result of a single linker unit molecular construct with one scFv specific for ectodomain of TfR1 as a targeting element and three scFvs specific for β-amyloid as effector elements.

The procedure for tetrazine-TCO ligation was performed per the manufacturer's instructions (Jena Bioscience GmbH, Jena, Germany). Briefly, 12.6 μl of the targeting element (5.65 mg/ml) was added to the solution containing the linker unit with effector elements at a molar ratio of 10:1 ([tetrazine]:[TCO]). The reaction mixture was incubated for 3 hours at room temperature. The product was subjected to mass spectrometric analysis, and the result indicated a molecular weight of 114,248 daltons (FIG. 18C).

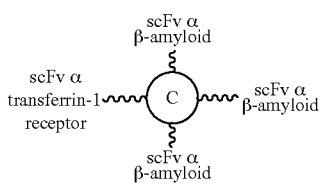
The product, as illustrated herein, was a single linker unit molecular construct with one scFv specific for ectodomain of TfR1 as a targeting element and three scFvs specific for β-amyloid as effector elements.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A linker unit comprising, a center core that comprises, (1) a first polypeptide comprising a plurality of lysine (K) residues, wherein each K residue and its next K residue are separated by a filler sequence comprising glycine (G) and serine (S) residues, and the number of K residues ranges from 2 to 15; or (2) a second polypeptide comprising the sequence of $(X_{aa}—K)_n$, where $X_{aa}$ is a PEGylated amino acid having 2 to 12 repeats of ethylene glycol (EG) unit, and n is an integral from 2 to 15; wherein at least one of the N- and C-terminal amino acid residues of the center core is an amino acid having an azide or an alkyne group or is a cysteine residue, wherein when one of the N- and C-terminal amino acid residues is the cysteine residue, the linker unit further comprises, optionally, a coupling arm that is linked to the cysteine residue via the thiol group of the cysteine residue and has the azide, the alkyne, a tetrazine, a cyclooctene, or a cyclooctyne group at the free terminus thereof, a plurality of linking arms respectively linked to the K residues of the center core;

optionally, a plurality of connecting arms respectively linked to the plurality of the linking arms via CuAAC reaction, SPAAC reaction, or iEDDA reaction; and a plurality of first elements that are respectively linked to the plurality of linking arms via forming an amide bound therebetween, or via thiol-maleimide reaction, CuAAC reaction, SPAAC reaction, or iEDDA reaction; or respectively linked to the plurality of connecting arms via forming an amide bound therebetween, or via thiol-maleimide reaction, wherein, each of the first elements is a single-chain variable fragment (scFv) specific for F protein of respiratory syncytia virus (RSV), gp120 protein of human deficiency virus type 1 (HIV-1), hepatitis B surface antigen of HBV, hemagglutinin A (HA) protein of influenza A virus, glycoprotein of cytomegalovirus, glycoprotein of rabies virus, surface antigen of *Clostridium difficile, Pseudomonas aeruginosa* serotype IATS O11, clumping factor A of *Staphylococcus aureus*, endotoxin of Gram-negative bacteria, lipoteichoic acid of *staphylococcus* areus, anthrax toxin, or Shiga-like toxin type I or II of *Escherichia coli*; and when the plurality of linking arms are linked to the plurality of connecting arms or the plurality of first elements via CuAAC reaction or SPAAC reaction, then the amino acid residue at the N- or C-terminus of the center core is a cysteine residue, and the free terminus of the coupling arm is the tetrazine or the cyclooctene group; or when the plurality of linking arms are linked to the plurality of connecting arms or the plurality of first elements via iEDDA reaction, then the amino acid residue at the N- or C-terminus of the center core has the azide or the alkyne group, or the amino acid residue at the N- or C-terminus of the center core is a cysteine residue, and the free terminus of the coupling arm is the azide, the alkyne, or the cyclooctyne group.

2. The linker unit of claim 1, wherein the filler sequence has the sequence of GS, GGS, GSG, or SEQ ID NOs: 1-16.

3. The linker unit of claim 1, wherein the first polypeptide comprises 2-15 units of the sequence of G1-5SK.

4. The linker unit of claim 3, wherein the first polypeptide comprises the sequence of (GSK)2-15.

5. The linker unit of claim 1, wherein each of the linking arms is a PEG chain having 2-20 repeats of EG units.

6. The linker unit of claim 1, wherein each of the linking arms is a PEG chain having 2-20 repeats of EG units with a disulfide linkage at the free terminus thereof.

7. The linker unit of claim 1, wherein the coupling arm is a PEG chain having 2-12 repeats of EG units.

8. The linker unit of claim 1, wherein the amino acid residue having the azide group is L-azidohomoalanine (AHA), 4-azido-L-phenylalanine, 4-azido-D-phenylalanine, 3-azido-L-alanine, 3-azido-D-alanine, 4-azido-L-homoalanine, 4-azido-D-homoalanine, 5-azido-L-ornithine, 5-azido-d-ornithine, 6-azido-L-lysine, or 6-azido-D-lysine.

9. The linker unit of claim 1, wherein the amino acid residue having the alkyne group is L-homopropargylglycine (L-HPG), D-homopropargylglycine (D-HPG), or beta-homopropargylglycine (β-HPG).

10. The linker unit of claim 1, wherein the cyclooctene group is trans-cyclooctene (TCO); and the cyclooctyne group is dibenzocyclooctyne (DBCO), difluorinated cyclooctyne(DIFO), bicyclononyne (BCN), or dibenzocyclooctyne (DICO).

11. The linker unit of claim 1, wherein the tetrazine group is 1,2,3,4-tetrazine, 1,2,3,5-tetrazine or 1,2,4,5-tetrazine, or derivatives thereof.

12. The linker unit of claim 1, wherein each of the first elements is the scFv specific for the F protein of RSV, the gp120 protein of HIV-1, the HA protein of influenza A virus, or the glycoprotein of cytomegalovirus.

13. The linker unit of claim 1, further comprising a second element that is linked to the center core via any of the following reactions:

CuAAC reaction occurred between the azide or alkyne group and the second element;

SPAAC reaction occurred between the azide or cyclooctyne group and the second element; and iEDDA reaction occurred between the cyclooctene or tetrazine group and the second element.

14. The linker unit of claim 13, wherein the second element is an scFv specific for CD32 or CD16b.

15. The linker unit of claim 14, wherein, the plurality of first elements that are respectively linked to the plurality of linking arms via forming the amide bound therebetween or via thiol-maleimide reaction, and the second element is linked to the azide or alkyne group of the N- or C-terminal amino acid residues of the center core via CuAAC reaction.

16. The linker unit of claim 15, further comprising a third element that is linked to the coupling arm via iEDDA reaction.

17. The linker unit of claim 14, wherein,
the plurality of first elements that are respectively linked to the plurality of linking arms via forming the amide bound therebetween or via thiol-maleimide reaction, and
the second element is linked to the azide group of the N- or C-terminal amino acid residues of the center core via SPAAC reaction.

18. The linker unit of claim 17, further comprising a third element that is linked to the coupling arm via iEDDA reaction.

* * * * *

SEQUENCE LISTING

```
<160> NUMBER OF SEQ ID NOS: 36

<210> SEQ ID NO 1
<211> LENGTH: 4
<212> TYPE: PRT
<213> ORGANISM: Artificial Sequence
<220> FEATURE:
<223> OTHER INFORMATION: filler sequence-1

<400> SEQUENCE: 1

Gly Gly Gly Ser
1

<210> SEQ ID NO 2
<211> LENGTH: 4
<212> TYPE: PRT
<213> ORGANISM: Artificial Sequence
<220> FEATURE:
<223> OTHER INFORMATION: filler sequence-2

<400> SEQUENCE: 2

Gly Ser Gly Ser
1

<210> SEQ ID NO 3
<211> LENGTH: 4
<212> TYPE: PRT
<213> ORGANISM: Artificial Sequence
<220> FEATURE:
<223> OTHER INFORMATION: filler sequence-3

<400> SEQUENCE: 3

Gly Gly Ser Gly
1

<210> SEQ ID NO 4
<211> LENGTH: 5
<212> TYPE: PRT
<213> ORGANISM: Artificial Sequence
<220> FEATURE:
<223> OTHER INFORMATION: filler sequence-4

<400> SEQUENCE: 4

Gly Ser Gly Gly Ser
1               5

<210> SEQ ID NO 5
<211> LENGTH: 5
<212> TYPE: PRT
<213> ORGANISM: Artificial Sequence
<220> FEATURE:
<223> OTHER INFORMATION: filler sequence-5
```

```
<400> SEQUENCE: 5

Ser Gly Gly Ser Gly
1               5

<210> SEQ ID NO 6
<211> LENGTH: 5
<212> TYPE: PRT
<213> ORGANISM: Artificial Sequence
<220> FEATURE:
<223> OTHER INFORMATION: filler sequence-6

<400> SEQUENCE: 6

Gly Gly Gly Gly Ser
1               5

<210> SEQ ID NO 7
<211> LENGTH: 6
<212> TYPE: PRT
<213> ORGANISM: Artificial Sequence
<220> FEATURE:
<223> OTHER INFORMATION: filler sequence-7

<400> SEQUENCE: 7

Gly Gly Ser Gly Gly Ser
1               5

<210> SEQ ID NO 8
<211> LENGTH: 7
<212> TYPE: PRT
<213> ORGANISM: Artificial Sequence
<220> FEATURE:
<223> OTHER INFORMATION: filler sequence-8

<400> SEQUENCE: 8

Gly Gly Ser Gly Gly Ser Gly
1               5

<210> SEQ ID NO 9
<211> LENGTH: 8
<212> TYPE: PRT
<213> ORGANISM: Artificial Sequence
<220> FEATURE:
<223> OTHER INFORMATION: filler sequence-9

<400> SEQUENCE: 9

Ser Gly Ser Gly Gly Ser Gly Ser
1               5

<210> SEQ ID NO 10
<211> LENGTH: 9
<212> TYPE: PRT
<213> ORGANISM: Artificial Sequence
<220> FEATURE:
<223> OTHER INFORMATION: filler sequence-10

<400> SEQUENCE: 10

Gly Ser Gly Gly Ser Gly Ser Gly Ser
1               5

<210> SEQ ID NO 11
<211> LENGTH: 10
<212> TYPE: PRT
<213> ORGANISM: Artificial Sequence
<220> FEATURE:
<223> OTHER INFORMATION: filler sequence-11

<400> SEQUENCE: 11
```

```
Ser Gly Gly Ser Gly Gly Ser Gly Ser Gly
1               5                   10

<210> SEQ ID NO 12
<211> LENGTH: 11
<212> TYPE: PRT
<213> ORGANISM: Artificial Sequence
<220> FEATURE:
<223> OTHER INFORMATION: filler sequence-12

<400> SEQUENCE: 12

Gly Gly Ser Gly Gly Ser Gly Gly Ser Gly Ser
1               5                   10

<210> SEQ ID NO 13
<211> LENGTH: 12
<212> TYPE: PRT
<213> ORGANISM: Artificial Sequence
<220> FEATURE:
<223> OTHER INFORMATION: filler sequence-13

<400> SEQUENCE: 13

Ser Gly Gly Ser Gly Gly Ser Gly Ser Gly Gly Ser
1               5                   10

<210> SEQ ID NO 14
<211> LENGTH: 13
<212> TYPE: PRT
<213> ORGANISM: Artificial Sequence
<220> FEATURE:
<223> OTHER INFORMATION: filler sequence-14

<400> SEQUENCE: 14

Gly Gly Gly Gly Ser Gly Gly Ser Gly Gly Gly Gly Ser
1               5                   10

<210> SEQ ID NO 15
<211> LENGTH: 14
<212> TYPE: PRT
<213> ORGANISM: Artificial Sequence
<220> FEATURE:
<223> OTHER INFORMATION: filler sequence-15

<400> SEQUENCE: 15

Gly Gly Gly Ser Gly Ser Gly Ser Gly Ser Gly Gly Gly Ser
1               5                   10

<210> SEQ ID NO 16
<211> LENGTH: 15
<212> TYPE: PRT
<213> ORGANISM: Artificial Sequence
<220> FEATURE:
<223> OTHER INFORMATION: filler sequence-16

<400> SEQUENCE: 16

Ser Gly Ser Gly Gly Gly Gly Gly Ser Gly Gly Ser Gly Ser Gly
1               5                   10                  15

<210> SEQ ID NO 17
<211> LENGTH: 16
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
```

```
<223> OTHER INFORMATION: polypeptide core-1

<400> SEQUENCE: 17

Cys Gly Gly Ser Gly Gly Ser Gly Gly Ser Lys Gly Ser Gly Ser Lys
1               5                   10                  15

<210> SEQ ID NO 18
<211> LENGTH: 19
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptitde core-2

<400> SEQUENCE: 18

Cys Gly Gly Ser Gly Gly Ser Gly Gly Ser Lys Gly Ser Gly Ser Lys
1               5                   10                  15

Gly Ser Lys

<210> SEQ ID NO 19
<211> LENGTH: 31
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide-3

<400> SEQUENCE: 19

Cys Gly Ser Lys Gly Ser Lys Gly Ser Lys Gly Ser Lys Gly Ser Lys
1               5                   10                  15

Gly Ser Lys Gly Ser Lys Gly Ser Lys Gly Ser Lys Gly Ser Lys
                20                  25                  30

<210> SEQ ID NO 20
<211> LENGTH: 8
<212> TYPE: PRT
<213> ORGANISM: Artificial Sequence
<220> FEATURE:
<223> OTHER INFORMATION: hapten

<400> SEQUENCE: 20

Trp Ala Asp Trp Pro Gly Pro Pro
1               5

<210> SEQ ID NO 21
<211> LENGTH: 16
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa is homopropargylglycine
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core-4

<400> SEQUENCE: 21

Xaa Gly Gly Ser Gly Gly Ser Gly Gly Ser Lys Gly Ser Gly Ser Lys
1               5                   10                  15
```

```
<210> SEQ ID NO 22
<211> LENGTH: 19
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa is homopropargylglycine
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core-5

<400> SEQUENCE: 22

Xaa Gly Gly Ser Gly Gly Ser Gly Gly Ser Lys Gly Ser Gly Ser Lys
1               5                   10                  15

Gly Ser Lys

<210> SEQ ID NO 23
<211> LENGTH: 19
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa is L-azidohomoalanine
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core-6

<400> SEQUENCE: 23

Xaa Gly Gly Ser Gly Gly Ser Gly Gly Ser Lys Gly Ser Gly Ser Lys
1               5                   10                  15

Gly Ser Lys

<210> SEQ ID NO 24
<211> LENGTH: 21
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa is homopropargylglycine
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core-7

<400> SEQUENCE: 24

Xaa Gly Gly Ser Gly Gly Ser Gly Gly Ser Lys Gly Ser Gly Ser Lys
1               5                   10                  15

Gly Ser Gly Ser Cys
            20

<210> SEQ ID NO 25
<211> LENGTH: 7
<212> TYPE: PRT
<213> ORGANISM: Artificial Sequence
<220> FEATURE:
<221> NAME/KEY: MOD_RES
<222> LOCATION: 1
```

```
<223> OTHER INFORMATION: ACETYLATION
<220> FEATURE:
<223> OTHER INFORMATION: polypeptide core-8
<220> FEATURE:
<221> NAME/KEY: MOD_RES
<222> LOCATION: 2,4,6
<223> OTHER INFORMATION: Xaa is PEGylated amino acid with two EG units

<400> SEQUENCE: 25

Cys Xaa Lys Xaa Lys Xaa Lys
1               5

<210> SEQ ID NO 26
<211> LENGTH: 11
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core-9
<220> FEATURE:
<221> NAME/KEY: MOD_RES
<222> LOCATION: 2,4,6,8,10
<223> OTHER INFORMATION: Xaa is PEGylated amino acid with six EG units

<400> SEQUENCE: 26

Cys Xaa Lys Xaa Lys Xaa Lys Xaa Lys Xaa Lys
1               5                   10

<210> SEQ ID NO 27
<211> LENGTH: 16
<212> TYPE: PRT
<213> ORGANISM: Artificial Sequence
<220> FEATURE:
<223> OTHER INFORMATION: 5xdrug

<400> SEQUENCE: 27

Cys Gly Ser Lys Gly Ser Lys Gly Ser Lys Gly Ser Lys Gly Ser Lys
1               5                   10                  15

<210> SEQ ID NO 28
<211> LENGTH: 666
<212> TYPE: PRT
<213> ORGANISM: Artificial Sequence
<220> FEATURE:
<223> OTHER INFORMATION: human transferrin-1 receptor

<400> SEQUENCE: 28

Leu Ala Gly Thr Glu Ser Pro Val Arg Glu Glu Pro Gly Glu Asp Phe
1               5                   10                  15

Pro Ala Ala Arg Arg Leu Tyr Trp Asp Asp Leu Lys Arg Lys Leu Ser
            20                  25                  30

Glu Lys Leu Asp Ser Thr Asp Phe Thr Ser Thr Ile Lys Leu Leu Asn
        35                  40                  45

Glu Asn Ser Tyr Val Pro Arg Glu Ala Gly Ser Gln Lys Asp Glu Asn
    50                  55                  60

Leu Ala Leu Tyr Val Glu Asn Gln Phe Arg Glu Phe Lys Leu Ser Lys
65                  70                  75                  80

Val Trp Arg Asp Gln His Phe Val Lys Ile Gln Val Lys Asp Ser Ala
                85                  90                  95

Gln Asn Ser Val Ile Ile Val Asp Lys Asn Gly Arg Leu Val Tyr Leu
            100                 105                 110

Val Glu Asn Pro Gly Gly Tyr Val Ala Tyr Ser Lys Ala Ala Thr Val
```

-continued

```
                115                 120                 125
Thr Gly Lys Leu Val His Ala Asn Phe Gly Thr Lys Lys Asp Phe Glu
            130                 135                 140

Asp Leu Tyr Thr Pro Val Asn Gly Ser Ile Val Ile Val Arg Ala Gly
145                 150                 155                 160

Lys Ile Thr Phe Ala Glu Lys Val Ala Asn Ala Glu Ser Leu Asn Ala
                165                 170                 175

Ile Gly Val Leu Ile Tyr Met Asp Gln Thr Lys Phe Pro Ile Val Asn
                180                 185                 190

Ala Glu Leu Ser Phe Phe Gly His Ala His Leu Gly Thr Gly Asp Pro
            195                 200                 205

Tyr Thr Pro Gly Phe Pro Ser Phe Asn His Thr Gln Phe Pro Pro Ser
    210                 215                 220

Arg Ser Ser Gly Leu Pro Asn Ile Pro Val Gln Thr Ile Ser Arg Ala
225                 230                 235                 240

Ala Ala Glu Lys Leu Phe Gly Asn Met Glu Gly Asp Cys Pro Ser Asp
                245                 250                 255

Trp Lys Thr Asp Ser Thr Cys Arg Met Val Thr Ser Glu Ser Lys Asn
            260                 265                 270

Val Lys Leu Thr Val Ser Asn Val Leu Lys Glu Ile Lys Ile Leu Asn
        275                 280                 285

Ile Phe Gly Val Ile Lys Gly Phe Val Glu Pro Asp His Tyr Val Val
290                 295                 300

Val Gly Ala Gln Arg Asp Ala Trp Gly Pro Gly Ala Ala Lys Ser Gly
305                 310                 315                 320

Val Gly Thr Ala Leu Leu Leu Lys Leu Ala Gln Met Phe Ser Asp Met
                325                 330                 335

Val Leu Lys Asp Gly Phe Gln Pro Ser Arg Ser Ile Ile Phe Ala Ser
            340                 345                 350

Trp Ser Ala Gly Asp Phe Gly Ser Val Gly Ala Thr Glu Trp Leu Glu
        355                 360                 365

Gly Tyr Leu Ser Ser Leu His Leu Lys Ala Phe Thr Tyr Ile Asn Leu
    370                 375                 380

Asp Lys Ala Val Leu Gly Thr Ser Asn Phe Lys Val Ser Ala Ser Pro
385                 390                 395                 400

Leu Leu Tyr Thr Leu Ile Glu Lys Thr Met Gln Asn Val Lys His Pro
                405                 410                 415

Val Thr Gly Gln Phe Leu Tyr Gln Asp Ser Asn Trp Ala Ser Lys Val
            420                 425                 430

Glu Lys Leu Thr Leu Asp Asn Ala Ala Phe Pro Phe Leu Ala Tyr Ser
        435                 440                 445

Gly Ile Pro Ala Val Ser Phe Cys Phe Cys Glu Asp Thr Asp Tyr Pro
    450                 455                 460

Tyr Leu Gly Thr Thr Met Asp Thr Tyr Lys Glu Leu Ile Glu Arg Ile
465                 470                 475                 480

Pro Glu Leu Asn Lys Val Ala Arg Ala Ala Glu Val Ala Gly Gln
                485                 490                 495

Phe Val Ile Lys Leu Thr His Asp Val Glu Leu Asn Leu Asp Tyr Glu
            500                 505                 510

Arg Tyr Asn Ser Gln Leu Leu Ser Phe Val Arg Asp Leu Asn Gln Tyr
        515                 520                 525

Arg Ala Asp Ile Lys Glu Met Gly Leu Ser Leu Gln Trp Leu Tyr Ser
    530                 535                 540
```

```
Ala Arg Gly Asp Phe Phe Arg Ala Thr Ser Arg Leu Thr Thr Asp Phe
545                 550                 555                 560

Gly Asn Ala Glu Lys Thr Asp Arg Phe Val Met Lys Lys Leu Asn Asp
                565                 570                 575

Arg Val Met Arg Val Glu Tyr His Phe Leu Ser Pro Tyr Val Ser Pro
            580                 585                 590

Lys Glu Ser Pro Phe Arg His Val Phe Trp Gly Ser Gly Ser His Thr
        595                 600                 605

Leu Pro Ala Leu Leu Glu Asn Leu Lys Leu Arg Lys Gln Asn Asn Gly
    610                 615                 620

Ala Phe Asn Glu Thr Leu Phe Arg Asn Gln Leu Ala Leu Ala Thr Trp
625                 630                 635                 640

Thr Ile Gln Gly Ala Ala Asn Ala Leu Ser Gly Asp Val Trp Asp Ile
                645                 650                 655

Asp Asn Glu Phe His His His His His His
                660                 665

<210> SEQ ID NO 29
<211> LENGTH: 192
<212> TYPE: PRT
<213> ORGANISM: Artificial Sequence
<220> FEATURE:
<223> OTHER INFORMATION: human CD32

<400> SEQUENCE: 29

Gln Ala Ala Pro Pro Lys Ala Val Leu Lys Leu Glu Pro Pro Trp
1               5                   10                  15

Ile Asn Val Leu Gln Glu Asp Ser Val Thr Leu Thr Cys Gln Gly Ala
                20                  25                  30

Arg Ser Pro Glu Ser Asp Ser Ile Gln Trp Phe His Asn Gly Asn Leu
            35                  40                  45

Ile Pro Thr His Thr Gln Pro Ser Tyr Arg Phe Lys Ala Asn Asn Asn
        50                  55                  60

Asp Ser Gly Glu Tyr Thr Cys Gln Thr Gly Gln Thr Ser Leu Ser Asp
65                  70                  75                  80

Pro Val His Leu Thr Val Leu Ser Glu Trp Leu Val Leu Gln Thr Pro
                85                  90                  95

His Leu Glu Phe Gln Glu Gly Glu Thr Ile Met Leu Arg Cys His Ser
            100                 105                 110

Trp Lys Asp Lys Pro Leu Val Lys Val Thr Phe Phe Gln Asn Gly Lys
        115                 120                 125

Ser Gln Lys Phe Ser Arg Leu Asp Pro Thr Phe Ser Ile Pro Gln Ala
    130                 135                 140

Asn His Ser His Ser Gly Asp Tyr His Cys Thr Gly Asn Ile Gly Tyr
145                 150                 155                 160

Thr Leu Phe Ser Ser Lys Pro Val Thr Ile Thr Val Gln Val Pro Ser
                165                 170                 175

Met Gly Ser Ser Ser Pro Met Gly Ile Ile His His His His His His
            180                 185                 190

<210> SEQ ID NO 30
<211> LENGTH: 256
<212> TYPE: PRT
<213> ORGANISM: Artificial Sequence
<220> FEATURE:
<223> OTHER INFORMATION: scFv of anti-RSV mAb
```

<400> SEQUENCE: 30

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Arg Gly Ser Thr Ser Gly
            100                 105                 110

Ser Gly Lys Pro Gly Ser Gly Glu Gly Ser Thr Lys Gly Gln Val Thr
        115                 120                 125

Leu Arg Glu Ser Gly Pro Ala Leu Val Lys Pro Thr Gln Thr Leu Thr
    130                 135                 140

Leu Thr Cys Thr Phe Ser Gly Phe Ser Leu Ser Thr Ser Gly Met Ser
145                 150                 155                 160

Val Gly Trp Ile Arg Gln Pro Pro Gly Lys Ala Leu Glu Trp Leu Ala
                165                 170                 175

Asp Ile Trp Trp Asp Asp Lys Lys Asp Tyr Asn Pro Ser Leu Lys Ser
            180                 185                 190

Arg Leu Thr Ile Ser Lys Asp Thr Ser Lys Asn Gln Val Val Leu Lys
        195                 200                 205

Val Thr Asn Met Asp Pro Ala Asp Thr Ala Thr Tyr Tyr Cys Ala Arg
    210                 215                 220

Ser Met Ile Thr Asn Trp Tyr Phe Asp Val Trp Gly Ala Gly Thr Thr
225                 230                 235                 240

Val Thr Val Ser Ser Gly Gly Gly Gly Ser Gly Gly Gly Gly Ser Cys
                245                 250                 255

<210> SEQ ID NO 31
<211> LENGTH: 257
<212> TYPE: PRT
<213> ORGANISM: Artificial Sequence
<220> FEATURE:
<223> OTHER INFORMATION: scFv of anti-endotoxin mAb

<400> SEQUENCE: 31

Asp Ile Gln Met Asn Gln Ser Pro Ser Ser Leu Ser Ala Ser Leu Gly
1               5                   10                  15

Asp Thr Ile Ser Ile Thr Cys Arg Ala Ser Gln Asn Ile Asn Ile Trp
            20                  25                  30

Leu Ser Trp Tyr Gln Gln Lys Pro Gly Asn Val Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Ile Ile Ser Ser Leu Gln Pro
65                  70                  75                  80

Glu Asp Ile Ala Thr Tyr Tyr Cys Leu Gln Gly Gln Ser Tyr Pro Arg
                85                  90                  95

Thr Phe Gly Gly Gly Thr Lys Leu Glu Ile Lys Arg Gly Ser Thr Ser

```
              100                 105                 110
Gly Ser Gly Lys Pro Gly Ser Gly Glu Gly Ser Thr Lys Gly Glu Val
            115                 120                 125
Lys Leu Val Glu Ser Gly Gly Gly Leu Val Gln Pro Gly Gly Ser Leu
            130                 135                 140
Ser Leu Ser Cys Ala Ala Ser Gly Phe Thr Phe Ser Asp Tyr Tyr Met
145                 150                 155                 160
Thr Trp Val Arg Gln Ala Pro Gly Lys Ala Pro Glu Trp Leu Ala Leu
                165                 170                 175
Ile Arg Asn Lys Arg Asn Gly Asp Thr Ala Glu Tyr Ser Ala Ser Val
                180                 185                 190
Lys Gly Arg Phe Thr Ile Ser Arg Asp Tyr Ser Arg Ser Ile Leu His
            195                 200                 205
Leu Gln Met Asn Ala Leu Arg Thr Glu Asp Ser Ala Thr Tyr Tyr Cys
            210                 215                 220
Val Arg Gln Gly Arg Gly Tyr Thr Leu Asp Tyr Trp Gly Gln Gly Thr
225                 230                 235                 240
Ser Val Thr Val Ser Ser Gly Gly Gly Ser Gly Gly Gly Gly Ser
                245                 250                 255
Cys
```

<210> SEQ ID NO 32
<211> LENGTH: 255
<212> TYPE: PRT
<213> ORGANISM: Artificial Sequence
<220> FEATURE:
<223> OTHER INFORMATION: scFv of anti-CD32a mAb

<400> SEQUENCE: 32

```
Ala Ile Gln Leu Thr Gln Ser Pro Ser Ser Leu Ser Ala Ser Val Gly
1               5                   10                  15
Asp Arg Val Thr Ile Thr Cys Arg Ala Ser Gln Gly Ile Asn Ser Ala
                20                  25                  30
Leu Ala Trp Tyr Gln Gln Lys Pro Gly Lys Ala Pro Lys Leu Leu Ile
            35                  40                  45
Tyr Asp Ala Ser Ser Leu Glu Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Phe Asn Ser Tyr Pro His
                85                  90                  95
Thr Phe Gly Gln Gly Thr Lys Leu Glu Ile Lys Arg Gly Ser Thr Ser
            100                 105                 110
Gly Ser Gly Lys Pro Gly Ser Gly Glu Gly Ser Thr Lys Gly Gln Val
            115                 120                 125
His Leu Val Glu Ser Gly Gly Gly Val Val Gln Pro Gly Arg Ser Leu
            130                 135                 140
Arg Leu Ser Cys Ala Ala Ser Gly Phe Thr Phe Ser Ser Tyr Gly Met
145                 150                 155                 160
His Trp Val Arg Gln Ala Pro Gly Lys Gly Leu Glu Trp Val Ala Val
                165                 170                 175
Ile Trp Tyr Asp Gly Ser Asn Tyr Tyr Tyr Thr Asp Ser Val Lys Gly
            180                 185                 190
Arg Phe Thr Ile Ser Arg Asp Asn Ser Lys Asn Thr Leu Tyr Leu Gln
            195                 200                 205
```

```
Met Asn Ser Leu Arg Ala Glu Asp Thr Ala Val Tyr Tyr Cys Ala Arg
        210                 215                 220

Asp Leu Gly Ala Ala Ala Ser Asp Tyr Trp Gly Gln Gly Thr Leu Val
225                 230                 235                 240

Thr Val Ser Ser Gly Gly Gly Gly Ser Gly Gly Gly Gly Ser Cys
                245                 250                 255

<210> SEQ ID NO 33
<211> LENGTH: 251
<212> TYPE: PRT
<213> ORGANISM: Artificial Sequence
<220> FEATURE:
<223> OTHER INFORMATION: scFv of anti-transferrin-1 receptor mAb

<400> SEQUENCE: 33

Asp Ile Val Ile Thr Gln Ser Pro Ser Ser Leu Ser Ala Ser Leu Gly
1               5                   10                  15

Asp Thr Ile Leu Ile Thr Cys His Ala Ser Gln Asn Ile Asn Val Trp
            20                  25                  30

Leu Ser Trp Phe Gln Gln Lys Pro Gly Asn Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Trp
                85                  90                  95

Thr Phe Gly Gly Gly Thr Lys Leu Glu Ile Lys Arg Gly Ser Thr Ser
            100                 105                 110

Gly Ser Gly Lys Pro Gly Ser Gly Glu Gly Ser Thr Lys Gly Gln Val
        115                 120                 125

Gln Leu Gln Gln Pro Gly Ala Ala Leu Val Arg Pro Gly Ala Ser Met
    130                 135                 140

Arg Leu Ser Cys Lys Ala Ser Gly Tyr Ser Phe Thr Thr Tyr Trp Met
145                 150                 155                 160

Asn Trp Val Lys Gln Arg Pro Gly Gln Gly Leu Glu Leu Ile Gly Met
                165                 170                 175

Ile His Pro Ser Asp Ser Glu Val Arg Leu Asn Gln Lys Phe Lys Asp
            180                 185                 190

Lys Ala Thr Leu Thr Val Asp Thr Ser Ser Ser Thr Ala Tyr Met Gln
        195                 200                 205

Leu Asn Ser Pro Thr Ser Glu Asp Ser Ala Val Tyr Tyr Cys Ala Arg
    210                 215                 220

Phe Gly Leu Asp Tyr Trp Gly Gln Gly Thr Thr Leu Thr Val Ser Ser
225                 230                 235                 240

Gly Gly Gly Gly Ser Gly Gly Gly Gly Ser Cys
                245                 250

<210> SEQ ID NO 34
<211> LENGTH: 262
<212> TYPE: PRT
<213> ORGANISM: Artificial Sequence
<220> FEATURE:
<223> OTHER INFORMATION: scFv of anti-beta-amyloid Bapineuzumab mAb

<400> SEQUENCE: 34

Asp Val Val Met Thr Gln Ser Pro Leu Ser Leu Pro Val Thr Pro Gly
```

```
1               5                   10                  15
Glu Pro Ala Ser Ile Ser Cys Lys Ser Ser Gln Ser Leu Leu Asp Ser
                20                  25                  30

Asp Gly Lys Thr Tyr Leu Asn Trp Leu Leu Gln Lys Pro Gly Gln Ser
            35                  40                  45

Pro Gln Arg Leu Ile Tyr Leu Val Ser Lys Leu Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gln Gly Thr Lys Val Glu Ile Lys
            100                 105                 110

Arg Gly Ser Thr Gly Ser Gly Lys Pro Gly Ser Gly Glu Gly Ser
        115                 120                 125

Thr Lys Gly Glu Val Gln Leu Leu Glu Ser Gly Gly Gly Leu Val Gln
    130                 135                 140

Pro Gly Gly Ser Leu Arg Leu Ser Cys Ala Ala Ser Gly Phe Thr Phe
145                 150                 155                 160

Ser Asn Tyr Gly Met Ser Trp Val Arg Gln Ala Pro Gly Lys Gly Leu
                165                 170                 175

Glu Trp Val Ala Ser Ile Arg Ser Gly Gly Gly Arg Thr Tyr Tyr Ser
            180                 185                 190

Asp Asn Val Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
    210                 215                 220

Tyr Tyr Cys Val Arg Tyr Asp His Tyr Ser Gly Ser Ser Asp Tyr Trp
225                 230                 235                 240

Gly Gln Gly Thr Leu Val Thr Val Ser Ser Ala Gly Gly Gly Ser
                245                 250                 255

Gly Gly Gly Gly Ser Cys
            260

<210> SEQ ID NO 35
<211> LENGTH: 239
<212> TYPE: PRT
<213> ORGANISM: Artificial Sequence
<220> FEATURE:
<223> OTHER INFORMATION: B6 scFv of anti-human TfR derived from phage
      display

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Ser Asp
                20                  25                  30

Val Ala Trp Tyr Gln Gln Lys Pro Gly Lys Ala Pro Lys Leu Leu Ile
            35                  40                  45

Ser Tyr Ser Gly Tyr Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Gly Phe Pro Leu
                85                  90                  95
```

Thr Phe Gly Gln Gly Thr Lys Val Glu Ile Lys Arg Gly Gly Gly
                100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
    130                 135                 140

Cys Ala Ala Ser Gly Phe Thr Ile Gly Asn Ser Ser Ile His Trp Val
145                 150                 155                 160

Arg Gln Ala Pro Gly Lys Gly Leu Glu Trp Val Ala Ser Ile Trp Pro
                165                 170                 175

Phe Gly Gly Ser Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Trp Ser Tyr
    210                 215                 220

Gly Phe Asp Tyr Trp Gly Gln Gly Thr Leu Val Thr Val Ser Ser
225                 230                 235

<210> SEQ ID NO 36
<211> LENGTH: 243
<212> TYPE: PRT
<213> ORGANISM: Artificial Sequence
<220> FEATURE:
<223> OTHER INFORMATION: scFv of anti-human CD32 derived from phage
      display

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asn Gly
            20                  25                  30

Val Ala Trp Tyr Gln Gln Lys Pro Gly Lys Ala Pro Lys Leu Leu Ile
        35                  40                  45

Phe Gly Thr Ser Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Phe Gly Gly Pro Met
                85                  90                  95

Thr Phe Gly Gln Gly Thr Lys Val Glu Ile Lys Arg Gly Gly Ser Ser
            100                 105                 110

Arg Ser Ser Ser Gly Gly Gly Ser Gly Gly Gly Glu Val
    115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Asn Asn Gly Gly Ile
145                 150                 155                 160

His Trp Val Arg Gln Ala Pro Gly Lys Gly Leu Glu Trp Val Ala Gly
                165                 170                 175

Ile Trp Pro Phe Gly Gly Phe Thr Ser Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

-continued

```
Ser Trp Phe Ser Trp Ser Asp Tyr Trp Gly Gln Gly Thr Leu Val Thr
225                 230                 235                 240
Val Ser Ser
```